US012806383B2

(12) United States Patent
Agah et al.

(10) Patent No.: US 12,806,383 B2
(45) Date of Patent: Nov. 24, 2026

(54) DUAL OCCLUSION CATHETER SYSTEM

(71) Applicant: RenovoRx, Inc., Mountain View, CA (US)

(72) Inventors: Ramtin Agah, Menlo Park, CA (US); Joseph F. Paraschac, Campbell, CA (US)

(73) Assignee: RenovoRx, Inc., Mountain View, CA (US)

( * ) Notice: Subject to any disclaimer, the term of this patent is extended or adjusted under 35 U.S.C. 154(b) by 756 days.

(21) Appl. No.: 18/184,620

(22) Filed: Mar. 15, 2023

(65) Prior Publication Data

US 2023/0302262 A1 Sep. 28, 2023

Related U.S. Application Data

(60) Provisional application No. 63/320,211, filed on Mar. 15, 2022.

(51) Int. Cl.
*A61M 25/10* (2013.01)
*A61M 25/09* (2006.01)

(52) U.S. Cl.
CPC ........ *A61M 25/1011* (2013.01); *A61M 25/09* (2013.01); *A61M 2025/091* (2013.01); *A61M 2025/1015* (2013.01); *A61M 2025/1052* (2013.01); *A61M 2025/1079* (2013.01)

(58) Field of Classification Search
CPC ................................................ A61M 25/1011
See application file for complete search history.

(56) References Cited

U.S. PATENT DOCUMENTS

| | | | | |
|---|---|---|---|---|
| 4,020,829 | A * | 5/1977 | Willson | A61M 25/09 604/95.01 |
| 4,328,811 | A | 5/1982 | Fogarty | |
| 4,445,892 | A | 5/1984 | Hussein et al. | |
| 4,630,609 | A | 12/1986 | Chin | |
| 4,655,746 | A | 4/1987 | Daniels et al. | |
| 4,696,304 | A | 9/1987 | Chin | |
| 4,714,460 | A | 12/1987 | Calderon | |
| 4,830,003 | A | 5/1989 | Wolff et al. | |
| 4,883,459 | A | 11/1989 | Calderon | |
| 5,281,200 | A | 1/1994 | Corso et al. | |
| 5,318,535 | A | 6/1994 | Miraki | |

(Continued)

FOREIGN PATENT DOCUMENTS

| | | | |
|---|---|---|---|
| EP | 0402467 | A1 | 12/1990 |
| JP | 2013500067 | A | 1/2013 |

(Continued)

OTHER PUBLICATIONS

US 7,316,661 B2, 01/2008, Azizi (withdrawn)

(Continued)

*Primary Examiner* — David P. Olynick
(74) *Attorney, Agent, or Firm* — Shay Glenn LLP

(57) ABSTRACT

Systems and methods for delivery of therapeutic materials for the treatment of cancer are disclosed. Some systems include a plurality of expandable occlusion members that can form seals with the inner walls of various vessels thereby isolating a section or region of the associated vessels. In some variations, the system may include one or more catheters that are in fluid communication and can transfer fluid around the isolated sections or region.

12 Claims, 32 Drawing Sheets

(56) References Cited

U.S. PATENT DOCUMENTS 5,338,301 A 8/1994 Diaz
5,397,307 A 3/1995 Goodin
5,411,479 A 5/1995 Bodden
5,415,636 A 5/1995 Forman
5,419,763 A 5/1995 Hildebrand
5,462,529 A 10/1995 Simpson et al.
5,478,309 A 12/1995 Sweezer et al.
5,484,412 A 1/1996 Pierpont
5,514,092 A 5/1996 Forman et al.
5,575,815 A 11/1996 Slepian et al.
5,810,757 A 9/1998 Sweezer et al.
5,833,644 A 11/1998 Azizi et al.
5,833,650 A 11/1998 Imran
5,833,672 A 11/1998 Kawata et al.
5,836,905 A 11/1998 Lemelson et al.
5,836,967 A 11/1998 Schneider
5,840,066 A 11/1998 Matsuda et al.
5,843,050 A 12/1998 Jones et al.
5,888,530 A 3/1999 Netti et al.
5,916,193 A 6/1999 Stevens et al.
5,919,135 A 7/1999 Lemelson
5,919,163 A 7/1999 Glickman
5,925,016 A 7/1999 Chomenky et al.
5,961,536 A 10/1999 Mickley et al.
5,968,012 A 10/1999 Ren et al.
6,030,362 A 2/2000 Boussignac et al.
6,051,014 A 4/2000 Jang
6,056,721 A 5/2000 Shulze
6,083,198 A 7/2000 Afzal
6,156,053 A 12/2000 Gandhi et al.
6,165,152 A 12/2000 Becker et al.
6,176,844 B1 1/2001 Lee
6,287,290 B1 9/2001 Perkins et al.
6,299,598 B1 10/2001 Bander
6,346,098 B1 2/2002 Yock et al.
6,351,663 B1 2/2002 Flower et al.
6,375,634 B1 4/2002 Carroll
6,440,097 B1 8/2002 Kupiecki
6,461,327 B1 10/2002 Addis et al.
6,482,172 B1 11/2002 Thramann
6,485,500 B1 11/2002 Kokish et al.
6,488,672 B1 12/2002 Dance et al.
6,508,777 B1 1/2003 Macoviak et al.
6,520,183 B2 2/2003 Amar
6,569,146 B1 5/2003 Werner et al.
6,569,148 B2 5/2003 Bagaoisan et al.
6,575,932 B1 6/2003 O'Brien et al.
6,589,264 B1 7/2003 Barbut et al.
6,592,546 B1 7/2003 Barbut et al.
6,682,499 B2 1/2004 Lenker
6,685,672 B1 2/2004 Forman
6,692,458 B2 2/2004 Forman et al.
6,699,231 B1 3/2004 Sterman et al.
6,702,781 B1 3/2004 Reifart et al.
6,706,013 B1 3/2004 Bhat et al.
6,706,062 B2 * 3/2004 Vardi ........................ A61F 2/91
623/1.35
6,723,070 B1 4/2004 Arai et al.
6,743,196 B2 6/2004 Barbut et al.
6,929,633 B2 8/2005 Evans et al.
6,939,320 B2 9/2005 Lennox
6,986,788 B2 1/2006 Paul et al.
7,150,736 B2 12/2006 Barbut et al.
7,179,251 B2 2/2007 Palasis
7,297,475 B2 11/2007 Koiwai et al.
7,452,532 B2 11/2008 Alt
7,503,904 B2 3/2009 Choi
7,537,562 B2 5/2009 Takano
7,645,259 B2 1/2010 Goldman
7,704,220 B2 4/2010 Solar et al.
7,708,715 B2 5/2010 Gellman
7,780,628 B1 8/2010 Keren et al.
7,815,624 B2 10/2010 Larson
7,887,661 B2 2/2011 Chiu et al.
8,043,257 B2 10/2011 Nguyen et al.
8,088,103 B2 1/2012 Teeslink et al.
8,162,879 B2 4/2012 Hattangadi et al.
8,172,792 B2 5/2012 Wang et al.
8,177,829 B2 5/2012 Benson et al.
8,182,446 B2 5/2012 Schaeffer et al.
8,182,463 B2 5/2012 Chiu et al.
8,187,229 B2 5/2012 Weitzner et al.
8,251,948 B2 8/2012 Goldman
8,414,473 B2 4/2013 Jenkins et al.
8,702,678 B2 4/2014 Comerota et al.
8,821,476 B2 9/2014 Agah et al.
8,870,849 B2 10/2014 Steinmetz et al.
9,254,210 B2 2/2016 Bourang
9,457,171 B2 10/2016 Agah et al.
9,463,304 B2 10/2016 Agah et al.
10,099,040 B2 10/2018 Agah et al.
10,286,191 B2 5/2019 Wang et al.
10,512,761 B2 12/2019 Agah et al.
10,695,543 B2 6/2020 Agah et al.
11,052,224 B2 7/2021 Agah et al.
11,541,211 B2 1/2023 Agah et al.
2001/0041862 A1 11/2001 Glickman
2002/0016565 A1 2/2002 Zadno-Azizi et al.
2002/0072706 A1 6/2002 Hiblar et al.
2002/0082548 A1 6/2002 Sanchez et al.
2002/0107471 A1 8/2002 Thompson et al.
2002/0115982 A1 8/2002 Barbut et al.
2003/0147862 A1 8/2003 Buschmann et al.
2003/0149997 A1 8/2003 Hageman
2005/0059930 A1 3/2005 Garrison et al.
2005/0059931 A1 3/2005 Garrison et al.
2005/0149112 A1 7/2005 Barbut
2005/0149159 A1 7/2005 Andreas et al.
2006/0009798 A1 1/2006 Callister et al.
2006/0149218 A1 7/2006 Slater et al.
2006/0149393 A1 7/2006 Calderon
2006/0173440 A1 8/2006 Lamson et al.
2006/0188442 A1 8/2006 Hallahan
2006/0200075 A1 9/2006 Azizi
2006/0253079 A1 11/2006 McDonough et al.
2007/0010782 A1 1/2007 Doty et al.
2007/0055132 A1 3/2007 Camus et al.
2008/0051660 A1 2/2008 Kakadaris et al.
2008/0058759 A1 3/2008 Makower et al.
2008/0082046 A1 * 4/2008 Kato ................. A61M 25/0043
604/96.01
2008/0269718 A1 10/2008 Wiener et al.
2009/0018526 A1 1/2009 Power et al.
2009/0043194 A1 2/2009 Barbut
2009/0048577 A1 2/2009 Gillies et al.
2009/0088676 A1 4/2009 Murata
2009/0131866 A1 5/2009 Zhang et al.
2009/0143760 A1 6/2009 Van Dam et al.
2009/0198093 A1 8/2009 Meissner et al.
2009/0198216 A1 8/2009 Muni et al.
2009/0209631 A1 8/2009 Zsebo
2009/0264734 A1 10/2009 Degani et al.
2009/0264819 A1 10/2009 Diethrich et al.
2009/0275918 A1 11/2009 Crocker
2010/0016836 A1 1/2010 Makower et al.
2010/0106181 A1 4/2010 Gross et al.
2010/0331815 A1 12/2010 Alt
2011/0093000 A1 4/2011 Ogle et al.
2011/0152683 A1 6/2011 Gerrans et al.
2011/0218494 A1 9/2011 Gerrans et al.
2011/0257577 A1 10/2011 Lane et al.
2011/0282195 A1 11/2011 Solar et al.
2012/0259215 A1 10/2012 Gerrans et al.
2013/0281971 A1 10/2013 Looper et al.
2014/0214002 A1 * 7/2014 Lieber ................ A61M 25/1011
604/509
2014/0364835 A1 12/2014 Allen et al.
2015/0018762 A1 1/2015 Fierens et al.
2015/0191546 A1 7/2015 Molldrem et al.
2016/0082178 A1 3/2016 Agah et al.
2017/0157370 A1 * 6/2017 Agah ................ A61M 25/0097
2018/0169067 A1 6/2018 Bascomb et al.
2020/0206481 A1 7/2020 Agah et al.

(56) References Cited

U.S. PATENT DOCUMENTS

| | | | |
|---|---|---|---|
| 2021/0268107 A1 | 9/2021 | Agah et al. |
| 2021/0338977 A1 | 11/2021 | Agah et al. |
| 2025/0332253 A1 | 10/2025 | Agah et al. |

FOREIGN PATENT DOCUMENTS

| | | | |
|---|---|---|---|
| JP | 2016168085 A | 9/2016 |
| JP | 2017500144 A | 1/2017 |
| JP | 2021529588 A | 11/2021 |
| WO | WO02/074178 A2 | 9/2002 |
| WO | WO2014/197362 A1 | 12/2014 |
| WO | WO2015/074045 A2 | 5/2015 |
| WO | WO2016/011328 A1 | 1/2016 |
| WO | WO2022/218991 A1 | 10/2022 |
| WO | WO2024/102497 A2 | 5/2024 |

OTHER PUBLICATIONS

America Cancer Society; Cancer facts and figures, American Cancer Society; 72 pages; retrieved from the internet (https://www.cancer.org/research/cancer-facts-statistics/all-cancer-facts-figures/cancer-facts-figures-2016.html); 2016 (the year of publication is sufficiently earlier than the effective U.S. filing date and any foreign priority date so that the particular month of publication is not in issue).

Burkhardt et al; Intra-arterial chemotherapy for malignant gliomas: a critical analysis; Interventional Neuroradiology; 17(3); pp. 286-295; Sep. 2011.

cancer.net; Colorectal cancer: stages; 12 pages; retrieved from the internet (https://www.cancer.net/cancer-types/colorectal-cancer/stages) on Jan. 14, 2020.

cancer.net; Liver cancer: statistics; 2 pages; retrieved from the internet (https://www.cancer.net/cancer-types/liver-cancer/statistics) on Jan. 14, 2020.

cancer.net; Uterine cancer: Statistics; 2 pages; retrieved from the internet (https://www.cancer.net/cancer-types/uterine-cancer/statistics) on Jan. 14, 2020.

Chauffert et al.; Phase III trial comparing intensive induction chemoradiotherapy (60 Gy, infusional 5-FU and intermittent cisplatin) followed by maintenance gemcitabine with gemcitabine alone for locally advanced unresectable pancreatic cancer. Definitive results of the 2000-01 FFCD?SFRO study; Annals of Oncology; 19(9); pp. 1592-1599; Sep. 2008.

Kawaguchi et al; Comparison of neoadjuvant intraaterial chemotherapy versus concurrent chemoradiotherapy in patients with stage IIB uterine cervical cancer; World Journal of Oncology; 4(6); pp. 221-229; Dec. 2013.

Lewandowski et al.; Transcatheter intraarterial therapies: rationale and overview; Radiology; 259(3); pp. 641-657; Jun. 2011.

Mahadevan et al.; Sterotactic body radiotherapy and gemcitabine for locally advanced pancreatic cancer; International Journal of Radiation Oncology*Biology*Physics; 78(3); pp. 735-742; Nov. 2010.

Medgadget; Renovocath for targeted fluid delivery into peripheral vasculature cleared in europe; 3 pages; retrieved from the internet (https://www.medgadget.com/2015/10/renovocath-targeted-fluid-delivery-peripheral-vasculature-cleared-europe.html); Oct. 23, 2015.

Moghanaki; Further evidence of effective adjuvant combined radiation and chemotherapy following curative resection of pancreatic cancer; Gastrointestinal Tumor Study Group; Cancer; 59(12); pp. 2006-2010; 1987 (the year of publication is sufficiently earlier than the effective U.S. filing date and any foreign priority date so that the particular month of publication is not in issue).

Multhoff et al.; Radiation-induced changes in microcirculation and interstitial fluid pressure affecting delivery of macromolecules and nanotherapeutics to tumors. Frontiers in Oncology, 2012; 2(165); pp. 1-6, Nov. 2012.

National Cancer Institute; About cancer; 3 pages; retrieved from the internet (https://www.cancer.gov/about-cancer) on Jan. 14, 2020.

Neoptolemos et al; Adjuvant chemoradiotherapy and chemotherapy in resectable pancreatic cancer: a randomised controlled trial; The Lancet; 358(9293); pp. 1576-1585; Nov. 2001.

RENOVORX; RenovoCath Animation, delivering what matters; Dec. 17, 2014 (Dec. 17, 2014), Retrieved from the internet: 1 page; URL:https//www.youtube.com/watch?v=?v=LFZ7tvCU2a4&feature=youtube on Jan. 13, 2020.

RENOVORX; RenovoCath } RC120 Receives FDA 510(k) Clearance; 3 pages; retrieved from the internet (https://renovorx.com/renovocath-rc120-receives-fda-clearance/); Oct. 30, 2014.

RENOVORX; Researchers report survival benefits with use of renovocath TM in patients with locally advanced pancreatic tumors, 2 pages; retrieved from the internet (https://renovorx.com/researchers-report-survival-benefits-use-renovocath-patients-locally-advanced-pancreatic-tumors/); Apr. 19, 2017.

RENOVORX; Wayback Machine: RenovoCath } RC120—RenovoRx; 7 pages; retrieved from the internet (https://web.archive.org/web/20230000000000*/renovorx.com/wp-content/uploads/2016/07/MTK-5001.pdf); Apr. 25, 2017.

Sante; Lungcancer prognosis; 3 pages; retrieved from the internet (https://translate.google.com/translate?hl=en&sl=fr&u=http://www.lungcancer-prognosis.com/&prev=search) on Jan. 14, 2020.

Suryadevra et al; Immunotherapy for malignant glioma; Surgical Neurology International; 6(Suppl 1); S68-S77; Feb. 2015.

Vogl et al.; Regional chemotherapy of the lung: transpulmonary chemoembolization in malignant lung tumors; Seminars in Interventional Radiology; 30(2); pp. 176-184; Jun. 2013.

WASAN; The Emerging Synergy between Radioembolization, Systemic Chemotherapy, and Liver Surgery in Metastatic Colorectal Cancer; European Oncological Disease: 1(1); pp. 52-58; 2007 (the year of publication is sufficiently earlier than the effective U.S. filing date and any foreign priority date so that the particular month of publication is not in issue).

Agah et al.; U.S. Appl. No. 18/149,649 entitled "Methods for delivery of therapeutic materials to treat cancer," filed Jan. 3, 2023.

Goodman et al.; Static and dynamic vascular impact of large artery irradiation; International Journal of Radiation Oncology* Biology* Physics; 26(2); pp. 305-310; May 20, 1993.

Agah et al.; U.S. Appl. No. 19/129,277 entitled "Methods and apparatuses for delivering an agent through the vasa vasorum," filed May 12, 2025.

Jain; Delivery of molecular and cellular medicine to solid tumors; Advanced Drug Delivery Reviews; vol. 64; pp. 353-365; Dec. 1, 2012.

Park et al.; Radiation-induced vascular damage in tumors: implications of vascular damage in ablative hypofractionated radiotherapy (SBRT and SRS). Radiation research; 177(3); pp. 311-327; Mar. 1, 2012.

* cited by examiner

DUAL OCCLUSION CATHETER SYSTEM

PRIORITY CLAIM

This patent application claims priority to U.S. Provisional Patent Application No. 63/320,211, titled "METHODS FOR DELIVERY OF THERAPEUTIC MATERIALS FOR THE TREATMENT OF CANCER" and filed on Mar. 15, 2022, herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This disclosure relates to delivering therapeutic materials, and devices and methods of using them.

BACKGROUND

The embodiments described herein relate generally to methods for delivering a therapeutic material to treat a patient. In some cases the treatment is for treatment of cancer, such as, but not limited to pancreatic cancer.

Pancreatic cancer is considered an almost chemoresistant tumor. The ineffective result of systemic chemotherapy is at least in part due to an insufficient drug concentration within the tumor because of dose-limited toxicity in bone marrow and epithelial tissue. Since systemic chemotherapy is limited its effectiveness, localized therapy can be desirable for advanced pancreatic cancer patients. For example, one such treatment can include local intra-arterial delivery of chemotherapy. Intra-arterial infusion allows higher drug concentration to reach the tumor, overcoming the problem of poor blood flow to tumor mass in comparison to healthy tissue. Furthermore, intra-arterial chemotherapy can also take advantage of the first pass effect of chemotherapeutics, generating higher-level drug concentrations at the tumor cell membrane and therefore, enhancing cellular drug uptake as compared to intravenous infusion. Lastly, local delivery can reduce systemic side effects.

Such a chemotherapy treatment is usually administered through catheters placed in the celiac/hepatic artery or portal vein, however, a best mode of catheter placement has yet to be established. The tumor response rates of pancreatic arterial infusion chemotherapy can range widely, for example, from 7% to 65%, at least in part due to efficacy of drug delivery where anticancer drugs were administered via the celiac artery without assessment of drug distribution. Thus, a need exists for improved methods for delivering a treatment such as a biologic agent and/or drug formation to target tissue of the pancreas, as well as hepatic tumors and cholangiocarinoma.

SUMMARY OF THE DISCLOSURE

Disclosed is a localized method for treatment of cancer, comprising the steps of: providing a drug delivery catheter; navigating the catheter to the bile duct; delivering a therapeutic agent into the bile duct.

According to one aspect of the aforementioned method, wherein the drug delivery catheter is a multi-occlusion balloon catheter. The multi-occlusion balloon catheter may comprise at least two balloons. The multi-occlusion balloon catheter may optionally include a pressure transducer between the balloons to optimize delivery technique.

According to one aspect of the aforementioned method, the therapeutic agent is selected from the group (5-fluorouracil (5-FU), Aldesleukin, Axitinib, Bleomycin, Carboplatin, Cetuximab, Cisplatin, Cyclophosphamide, Dacarbazine, Doxorubicin Hydrochloride, doxorubicin liposomal non-pegylated (un-coated), doxorubicin liposomal pegylated (PEGcoated), Floxuridine, Gemcitabine Hydrochloride, Irinotecan Hydrochloride Liposome, Lanreotide Acetate, leucovorin (antidote to folic acid antagonist used with 5FU), Methotrexate, Mitomycin, Mitoxantrone, Nivolumab, Olaparib, Oxaliplatin, Sorafenib Tosylate, Temsirolimus, Thiotepa, Topotecan Hydrochloride, Vinblastine Sulfate, vincristine sulfate).

According to one aspect of the aforementioned method, the navigating step includes navigating the catheter using ERCP.

According to one aspect of the aforementioned method, the navigating step includes navigating the catheter to the bile duct percutaneously.

According to one aspect of the aforementioned method, the localized method is used to treat pancreatic cancer.

According to one aspect of the aforementioned method, the localized method is used to treat at least one of hepatic tumors and cholangiocarinoma.

One innovative aspect of the subject matter described in this disclosure can be implemented as a dual occlusion catheter system. The system may include a first lumen having a proximal end and a distal end, the first lumen configured to be inserted into a first vessel, a first port disposed through the first lumen and a second port disposed through the first lumen. The system may further include a first expandable occlusion member disposed distally with respect to the first port and the second port and a second expandable occlusion member disposed between the first port and the second port, where the first expandable occlusion member and the second expandable occlusion member are configured to expand and form a seal with an inner surface of the first vessel.

The first port of the system may be in fluid communication with the second port. Further, the first expandable occlusion member and the second expandable occlusion member may be coupled to the first lumen.

In some variations, the system may further include a perfusion port disposed through the first lumen between the first expandable occlusion member and the second expandable occlusion member and a fluid delivery lumen coupled to the perfusion port and disposed within the first lumen, where the perfusion port and the fluid delivery lumen are configured to deliver a fluid to the first vessel.

The system may include a second lumen configured to extend through the first port into a second vessel, where the second vessel branches from the first vessel. Furthermore, the system may include a first guidewire configured to guide the first lumen within the first vessel. In some cases, the first guidewire may be further configured to guide the second lumen into the second vessel. A distal end of the first guidewire is configured to extend through the first port.

The system may include a second guidewire configured to guide the second lumen into the second vessel. Furthermore, the second lumen may be further configured to create a fluid communication path between the first vessel proximal to the first expandable occlusion member and the second vessel. In some instances, the system may include a third expandable occlusion member coupled to the second lumen and configured to expand and form a seal with an inner surface of the second vessel.

In some embodiments, the system may further include a first radiopaque mark disposed on the first lumen and a second radiopaque mark disposed on the second lumen, where the first radiopaque mark and the second radiopaque mark are configured to identify and distinguish the first lumen and the second lumen. The second lumen may be slidably coupled to the first lumen. In some cases, the first lumen may include a groove configured to receive a protrusion from the second lumen. In some other cases, may include a non-circular cross-section configured to prevent rotation within the first lumen.

In some variations, the system may include a first inflation lumen configured to expand the first expandable occlusion member and a second inflation lumen configured to expand the second expandable occlusion member. Furthermore, the first inflation lumen and the second inflation lumen may be disposed within the first lumen.

Another innovative aspect of the subject matter described in this disclosure may be implemented as another dual occlusion catheter system. The system may include a first lumen having a proximal end and a distal end, the first lumen configured to be inserted into a first vessel, a first port disposed through the first lumen, a second port disposed through the first lumen, a second lumen configured to extend through the first port into a second vessel, where the second vessel branches from the first vessel, a first guidewire configured to guide the first lumen within the first vessel, and a second guidewire configured to guide the second lumen into the second vessel.

The system may further include a first expandable occlusion member disposed distally with respect to the first port and the second port and a second expandable occlusion member disposed between the first port and the second port, where the first expandable occlusion member and the second expandable occlusion member are configured to expand and from a seal with an inner surface of the first vessel.

The system may further include a third expandable occlusion member coupled to the second lumen and configured to expand and form a seal with an inner surface of the second vessel. In some cases, the first port of the system may be in fluid communication with the second port. Furthermore, fluid may be transferred between the first lumen and the second lumen of the system.

In some variations, the system may include a perfusion port disposed through the first lumen between the first port and the second port and a fluid delivery lumen coupled to the perfusion port and disposed within the first lumen, where the perfusion port and the fluid delivery lumen are configured to deliver a fluid to the first vessel.

Another innovative aspect of the subject matter described in this disclosure may be implemented as an adjustable catheter system. The system may include a primary lumen configured to be inserted into a first vessel. The primary lumen may include a first lumen and a second lumen, slidably coupled to the first lumen, where the first lumen is disposed within the second lumen, and the first lumen is configured to extend distally from a distal end of the second lumen. The system may further include a first port disposed through the primary lumen, a second port disposed through the primary lumen, where the first port is distal with respect to the second port, a first expandable occlusion member disposed on the first lumen, and a second expandable occlusion member disposed between the second lumen, where the first lumen is configured to move relative to the second lumen and determine a distance between the first expandable occlusion member and the second expandable occlusion member.

The first port of the system may be in fluid communication with the second port. In some variations, the system may include an ancillary lumen configured to extend through the first port into a second vessel. The ancillary lumen and the primary lumen may be configured to conduct fluid between the first vessel and the second vessel. In some variations, the system may include a third expandable occlusion member disposed on the ancillary lumen and configured to expand and form a seal with an inner surface of the second vessel.

The adjustable catheter system may include a perfusion port disposed through the primary lumen configured to deliver a fluid to the first vessel. In some cases, the first port is disposed through the first lumen and is absent from the second lumen.

Another innovative aspect of the subject matter described in this disclosure may be implemented as a catheter for use in a biliary tree. The catheter may include a lumen having a distal end and a proximal end, where the lumen is configured to be inserted into a vessel and an expandable occlusion member coupled to the lumen and configured to expand and form a seal with an inner surface of the vessel, where the lumen is configured to deliver a liquid to the vessel distally with respect to the expandable occlusion member and where the expandable occlusion member is configured to prevent the liquid from flowing proximally within the vessel.

The vessel, in some cases, may be a common bile duct. In some cases, the liquid may include gemcitabine. Furthermore, the liquid, which may include gemcitabine, may be delivered through the catheter to a patient's liver. Although gemcitabine is mentioned, the liquid may include any therapeutic or chemotherapy agent.

In some variations, the lumen of the catheter may be configured to be positioned in the vessel through a duodenum. In some other variations, the lumen of the catheter may be configured to be positioned in the vessel percutaneously through a gall bladder. In some embodiments, the expandable occlusion member is configured to be positioned distally from a cystic duct thereby preventing the delivered liquid from entering the cystic duct.

Another innovative aspect of the subject matter described in this disclosure may be implemented as method of delivering a liquid to a vessel. The method may include positioning a first lumen within a first vessel, where a first port of the first lumen is proximate to an opening of a second vessel branching off of the first vessel, expanding a first expandable occlusion member coupled to the first lumen, where the first expandable occlusion member is positioned distally with respect to the opening of the second vessel, expanding a second expandable occlusion member coupled to the first lumen, where the second expandable occlusion member is positioned proximally with respect to the opening of the second vessel, extending a second lumen into the second vessel from the first lumen, and transferring fluid between the first vessel and the second vessel through the first lumen and the second lumen.

In some variations, the first expandable occlusion member and the second expandable occlusion member is configured to form a seal with an inner surface of the first lumen. The method may further include delivering a liquid to the first vessel through a perfusion port disposed through the first lumen, where the liquid is a therapeutic liquid.

In some cases, the first lumen may be positioned via a first guidewire. In some other cases, the second lumen may be positioned by the first guidewire. In still other cases, the second lumen may be positioned by a second guidewire different from the first guidewire.

In some variations, the first expandable member may be expanded through a first inflation lumen and the second expandable member is expanded through the second inflation lumen. The first inflation lumen and the second inflation lumen are disposed within the first lumen. Further, the method may include expanding a third expandable occlusion member coupled to the second lumen, where the third expandable occlusion member is configured to form a seal with an inner surface of the second lumen.

This application may be related to, and may be used in conjunction with any of the embodiments described in U.S. patent application Ser. No. 18/149,649, titled "METHODS FOR DELIVERY OF THERAPEUTIC MATERIALS TO TREAT CANCER," filed on Jan. 3, 2023, which is a continuation of U.S. patent application Ser. No. 17/558,577, filed on Dec. 21, 2021, now U.S. Pat. No. 11,541,211, which is a continuation of U.S. patent application Ser. No. 16/685,950, filed Nov. 15, 2019, now U.S. Patent Application Publication No. 2020/0206481, which is a continuation of U.S. patent application Ser. No. 15/351,922, filed Nov. 15, 2016, now U.S. Pat. No. 10,512,761, which is a continuation-in-part of U.S. patent application Ser. No. 14/958,415, filed Dec. 3, 2015, now abandoned, which is a continuation-in-part of U.S. patent application Ser. No. 14/870,833, filed Sep. 30, 2015, now U.S. Pat. No. 9,463,304, which is a continuation of U.S. patent application Ser. No. 14/293,603, filed Jun. 2, 2014, now U.S. Pat. No. 9,457,171, which claims priority to and the benefit of U.S. Provisional Patent Application No. 61/830,218, filed Jun. 3, 2013. U.S. patent application Ser. No. 14/293,603 is also a continuation-in-part of U.S. patent application Ser. No. 12/958,711, filed Dec. 2, 2010, now U.S. Pat. No. 8,821,476, which claims priority to and the benefit of U.S. Provisional Patent Application No. 61/265,845, filed Dec. 2, 2009, each of the disclosures of which is incorporated herein by reference in its entirety.

All of the methods and apparatuses described herein, in any combination, are herein contemplated and can be used to achieve the benefits as described herein.

BRIEF DESCRIPTION OF THE DRAWINGS

Novel features of embodiments described herein are set forth with particularity in the appended claims. A better understanding of the features and advantages of the embodiments may be obtained by reference to the following detailed description that sets forth illustrative embodiments and the accompanying drawings.

DETAILED DESCRIPTION

Figure 1:
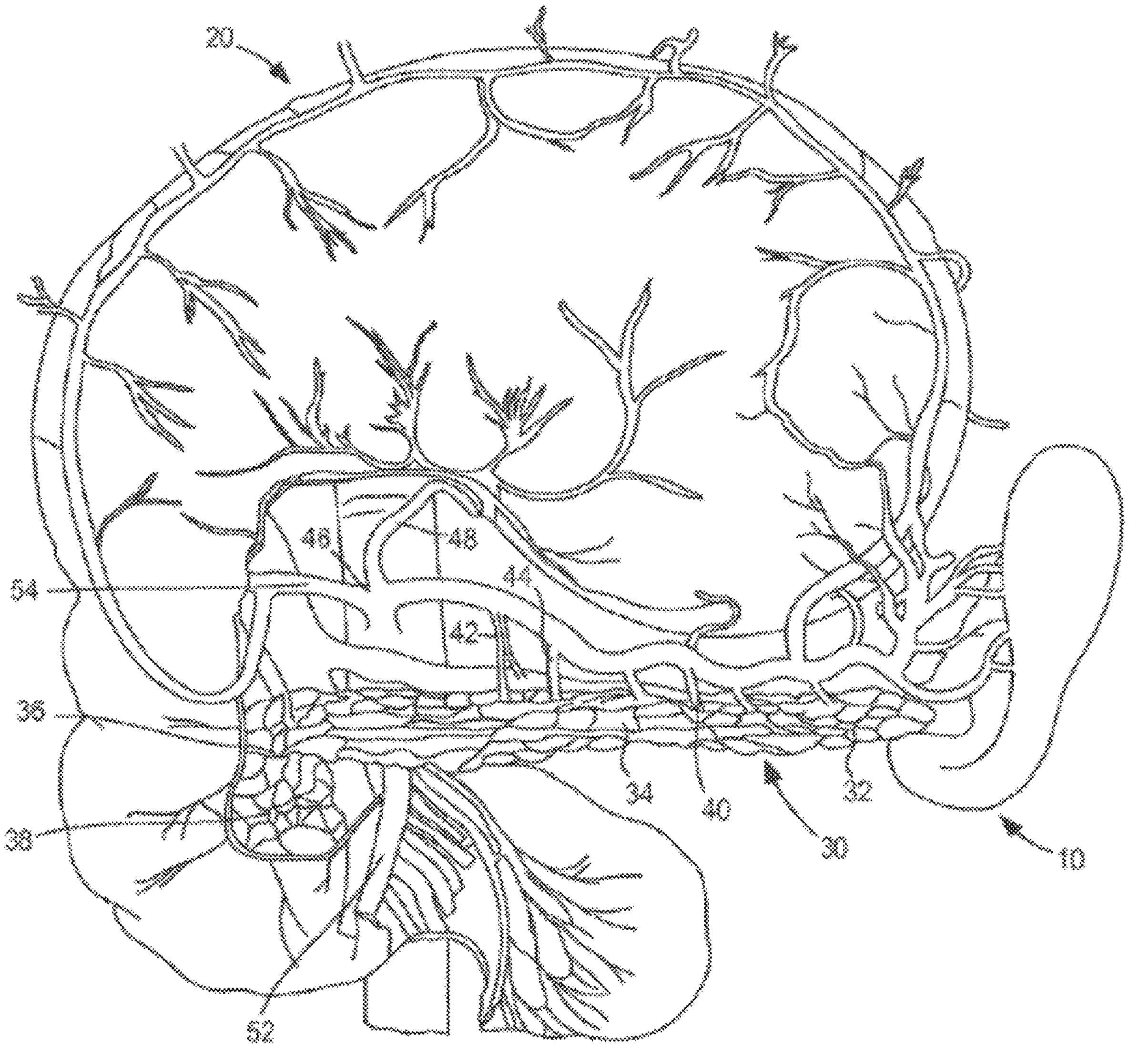
FIG. 1 is an illustration of a pancreas and related structure in a human.

Methods described herein can be used, for example, for the insertion and manipulation of a multi-occlusion catheter device to deliver a therapeutic agents to the bile duct for treatment of pancreatic cancer or other localized cancer. Tumors localized around the bile duct (cancer of the pancreatic head, primary and secondary liver tumors, and cholangiocarcinoma) may benefit from localized delivery through the bile duct itself The bile duct can be exogenously accessed through an endoscopic retrograde cholangiopancreatogram (ERCP) catheter, one can envision delivery of a double balloon catheter into the bile duct using established ERCP technique. After localizing the double balloon catheter to the area of bile duct involved/adjacent to the tumor, that area of bile duct is isolated by inflating the two balloon elements. Chemotherapeutic elements are then infused between the two balloons. By increasing the pressure between two balloon elements to exceed the interstitial tissue pressure, in a diffusion dependent manner, the chemotherapeutic agent will then diffuse out the wall of the bile duct and into the tissue.

By monitoring and/or adjusting the pressure between the balloons, one can change the penetration depth of the chemotherapy into the tissue.

According to some embodiments, a therapeutic material for treatment of pancreatic cancer or other localized cancer is delivered into the bile duct using the multi-occlusion catheter. The gall bladder is connected to the pancreas via the common bile duct. Localized delivery to the site of the tumor has advantages for both maximizing local drug concentration at the tumor site, and decreasing systemic side effects/toxicity. Thus the approach disclosed herein may avoid some of the toxicity related side effects of delivering chemotherapy drugs directly to the pancreas and may enable the use of more concentrated dosage of chemotherapy drugs. It should be understood that therapeutic particles may be substituted for or used in conjunction with chemotherapy drugs. Moreover, it should be understood that in some cases it may be useful to place a stent to open the bile duct prior to delivering the chemotherapy and/or therapeutic agent.

By way of example, such a use can include navigating a catheter such as a multi-occlusion catheter to the target anatomy using conventional percutaneous approaches or the same approach used for endoscopic retrograde cholangiopancreatogram (ERCP), isolating the bile duct, and then exogenously introducing therapeutic cells/agents/biologics into the isolated area, via an infusion port of the catheter. In such fashion, the cells/agents biologics can be delivered to the bile duct with high efficiency. In some embodiment, a device with two sliding balloon catheters can be used to isolate bile duct. The isolated area can then be perfused with cells/therapeutic agents via an infusion port disposed between the two balloon catheters. In some embodiments, the devices described herein can be arranged such that a user can manipulate a portion of the device substantially single handedly, to allow for accurate delivery of a biological agent and/or drug formulation to an isolated segment or portion of an organ.

This application incorporates by reference to U.S. application Ser. No. 14/958,415 filed on Dec. 3, 2015.

In some embodiments, an apparatus includes a handle, an inner catheter, an outer catheter, an actuator, a first occlusion element, and a second occlusion element. The inner catheter is coupled to the handle and the first occlusion element is coupled to the inner catheter. The inner catheter defines an inner catheter lumen that is configured to receive a guidewire. The outer catheter is coupled to the housing and the second occlusion element is coupled to the outer catheter. The outer catheter defines a first lumen that is in fluid communication with a distal opening and is configured to introduce a therapeutic agent through the distal opening into the bile duct. The outer catheter defines a second lumen that is configured to receive at least a portion of the inner catheter.

The actuator is coupled to the handle and is configured to move the outer catheter relative to the handle. The second occlusion element is disposed proximal to the first occlusion element and a distance therebetween is adjustable when the outer catheter is moved relative to the handle by the actuator.

In some embodiments, an apparatus includes a handle, an inner catheter, an outer catheter, a first occlusion element, a second occlusion element, and an actuator. The inner catheter is coupled to the handle and the first occlusion element is coupled to the inner catheter. The outer catheter is coupled to the housing and the second occlusion member is coupled to the outer catheter. The outer catheter defines a first lumen that is in fluid communication with a distal opening and that is configured to introduce a therapeutic agent therethrough and into the bile duct. The outer catheter defines a second lumen that is configured to receive at least a portion of the inner catheter. The second occlusion element is disposed proximal of the first occlusion element. The actuator is coupled to the handle and is configured to move the outer catheter relative to the handle between a first position in which the second occlusion element is at a first distance from the first occlusion element and a second position in which the second occlusion element is at a second distance from the first occlusion element, with the second distance being greater than the first distance.

In some embodiments, a system and/or device(s) is provided for endovascular introduction of therapeutic materials selectively to the bile duct for the treatment of pancreatic cancer. In some embodiments, a device and/or system can include, for example, an inner catheter having a distal retractable occlusion element and an inner catheter lumen adapted and configured to introduce a guidewire, and an outer catheter having a distal retractable occlusion element, an infusion lumen adapted and configured to introduce therapeutic materials to the bile duct, and a lumen for slidably receiving the inner catheter. In such an embodiment, the distal retractable occlusion element of the outer catheter can be positioned proximal to the distal retractable occlusion element of the inner catheter; and a sealing element can be included that is configured to selectively isolate or seal an end of the outer catheter to prevent therapeutic materials from entering into the lumen of the outer catheter in which the inner catheter is slidably disposed.

In some embodiments, a selective sealing element can include, for example, a ring, a membrane, or any other suitable element configured to prevent loss of therapeutic material into the lumen of the outer catheter in which the inner catheter is disposed. The lumen provided in the inner catheter can be configured to perfuse a distal organ beyond the targeted isolation region of the artery.

In some embodiments, a distance between the proximal retractable occlusion element and the selective sealing element can be configured for external adjustment, thus allowing a user to customize the isolated area (between the two occlusion elements) to better target the bile duct during delivery of biologics. The proximal retractable occlusion element and the selective sealing element can have a cross-sectional diameter, for example, between 2-12 mm.

In some embodiments, the devices and methods described herein can be used for isolating the perfusion area of the gall bladder for introduction of chemotherapy for treatment of pancreatic cancer, hepatic tumors and cholangiocarinoma or other therapeutic agents targeted to the pancreas.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the term "set" can refer to multiple features or a singular feature with multiple parts. For example, when referring to a set of ports, the set of ports can refer to a single port or to multiple ports.

As used herein, the words "proximal" and "distal" refer to a direction closer to and away from, respectively, an operator of, for example, a medical device. Thus, for example, the end of the medical device closest to the patient's body (e.g., contacting the patient's body or disposed within the patient's body) would be the distal end of the medical device, while the end opposite the distal end and closest to, for example, the user of the medical device, would be the proximal end of the medical device. Said another way, the distal end portion is the end that is located furthest from a point of reference, such as an origin or a point of attachment. For example, the distal end portion would be the end farthest away from a user's hand. The proximal end portion, thus, would be the position nearer to a point of reference such as an origin, i.e., the user's hand.

Table 1 is a list of chemotherapy drugs which may be delivered to the bile duct according to the method of the present invention.

TABLE 1

| # | Drug | Trade Name(s) | Common Indication(s) | Solvents/ Diluents |
|---|---|---|---|---|
| 1 | 5-fluorouracil (5-FU) | 5FU, Flourouracil, Adrucil | Breast, Liver, Pancreatic, Stomach | water |
| 2 | Aldesleukin | Proleukin | Kidney | water |
| 3 | Axitinib | Inlyta | Kidney | water |
| 4 | Bleomycin | Blenoxane | Cervical, Testicular | water |
| 5 | Carboplatin | Paraplatin | Ovarian | water |
| 6 | Cetuximab | Erbitux | Colorectal, Head, Neck | water |
| 7 | Cisplatin | Platinol-AQ | Bladder, Liver, Ovarian, Pancreatic, Testicular | water |
| 8 | Cyclo-phosphamide | Cytoxan | Breast, Ovarian, Pancreatic | water |
| 9 | Dacarbazine | DTIC-Dome | Pancreatic | water |
| 10 | Doxorubicin Hydrochloride | Adriamycin, Rubex, Caelyx | Breast, Liver, Ovarian, Pancreatic, Stomach | water (pH = 3) |
| 11 | doxorubicin liposomal, non-pegylated (un-coated) | Myocet | Breast, Liver, Ovarian, Pancreatic, Stomach | water (pH = 3) |
| 12 | doxorubicin liposomal, pegylated (PEG coated) | Doxil | Breast, Liver, Ovarian, Pancreatic, Stomach | water (pH = 3) |

TABLE 1-continued

| # | Drug | Trade Name(s) | Common Indication(s) | Solvents/ Diluents |
|---|---|---|---|---|
| 13 | Floxuridine | FUDR | Liver, Pancreatic | water |
| 14 | Gemcitabine Hydrochloride | Hospira, Gemcitab, Gemzar | Breast, Ovarian, Pancreatic | water (pH = 3) |
| 15 | Irinotecan Hydrochloride Liposome | Onivyde, Camptosar | Pancreatic | water (pH = 3) |
| 16 | Lanreotide Acetate | Somatuline Depot | Pancreatic | water |
| 17 | leucovorin (antidote to folic acid antagonist used with 5FU) | | Pancreatic | water or oral |
| 18 | Methotrexate | Otrexup, Rheumatrex, Trexall | Breast, Pancreatic | water |
| 19 | Mitomycin | Mutamycin, MMC, Mitomycin C, Mitozytrex | Liver, Pancreatic, Stomach | water |
| 20 | Mitoxantrone | Novantrone | Pancreatic | water |
| 21 | Nivolumab | Opdivo | Kidney | water |
| 22 | Olaparib | Lynparza | Ovarian | water |
| 23 | Oxaliplatin | Elotaxin | Pancreatic | water |
| 24 | Sorafenib Tosylate | Nexavar | Kidney | water |
| 25 | Temsirolimus | Torisel | Kidney | water |
| 26 | Thiotepa | | Bladder, Ovarian | water |
| 27 | Topotecan Hydrochloride | Hycamtin | Cervical, Ovarian | water (pH = 3) or oral |
| 28 | Vinblastine Sulfate | Velban, Velsar | Breast, Pancreatic, Testicular | water |
| 29 | vincristine sulfate | Alcrist, Biocristin, Oncocristin-AQ, VCR | Pancreatic | water |

FIG. 1 illustrates the liver 10, the gall bladder 20, and the pancreas 30 situated within an abdominal cavity (not shown) of a mammal (e.g., a human). The pancreas 30 is a gland organ which is part of the digestive and endocrine system of vertebrates. The pancreas 30 is both an endocrine gland producing hormones, including insulin, glucagon, and somatostatin, as well as an exocrine gland, secreting pancreatic juice containing digestive enzymes that pass to the small intestine. These enzymes help in the further breakdown of the carbohydrates, protein, and fat in the chyme.

As shown, the common bile duct leads from the gall bladder to the pancreas 30.

Figure 2:
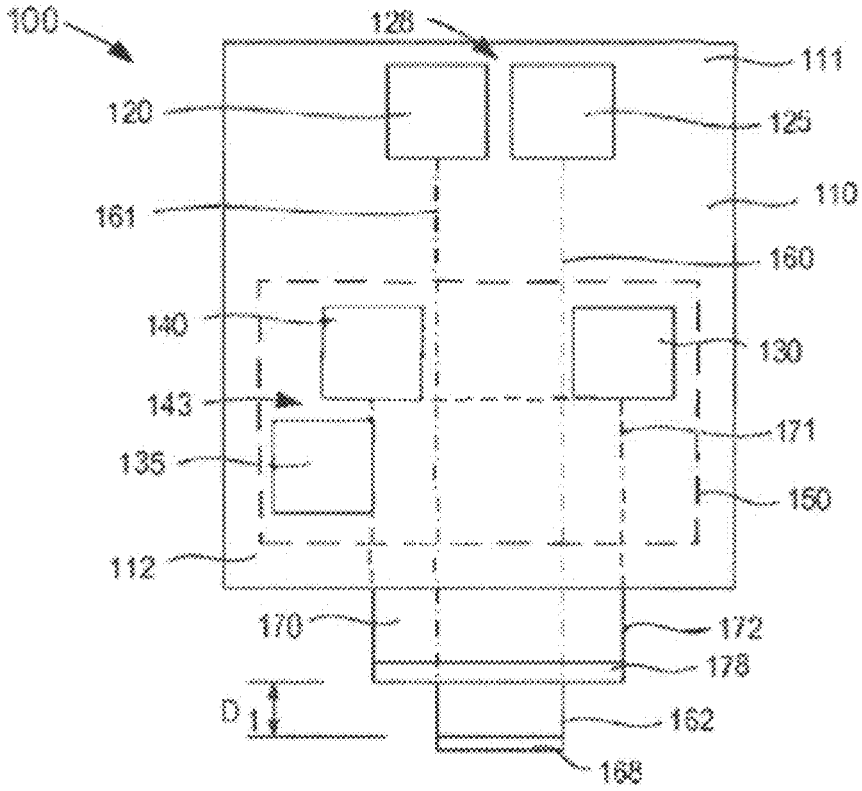
FIGS. 2 and 3 are schematic illustrations of a multi-occlusion catheter insertion device according to an embodiment, in a first configuration and a second configuration, respectively.
Figure 3:
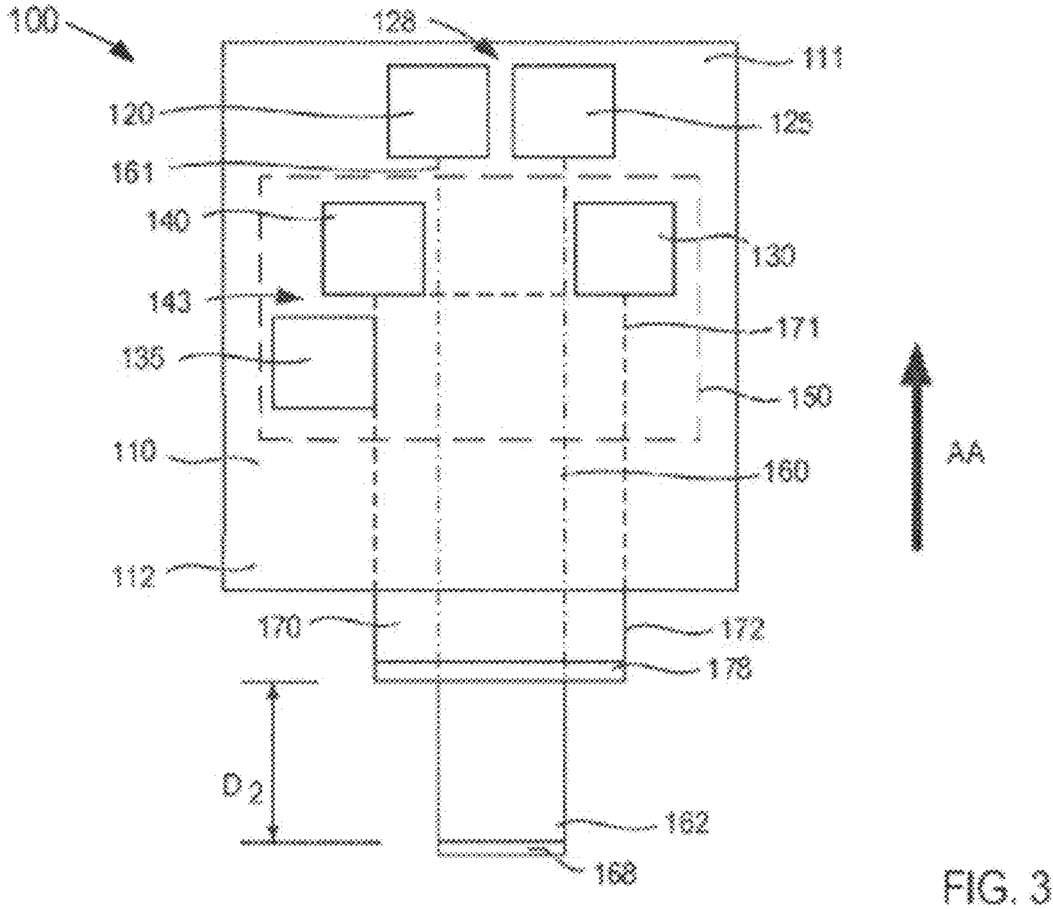

FIGS. 2 and 3 are schematic illustrations of a multi-occlusion catheter insertion device 100 useful for delivering therapeutic agents to the bile duct for treatment of pancreatic cancer. The multi-occlusion catheter insertion device 100 (also referred to herein as "device") can be arranged to allow for substantially single handed use to, for example, isolate a segment of a bodily lumen such as the buke duct, thereby allowing a procedure to be performed within the isolated segment and/or allowing a targeted delivery of a biological or therapeutic agent. The device 100 includes a handle 110, an actuator 150, a first catheter 160, and a second catheter 170. The handle 110 can be any suitable shape, size, or configuration. For example, in some embodiments, the handle 110 can have a shape and size that are configured to enhance the ergonomics of the device 100. As described in further detail herein, the handle 110 can be grasped by a user to insert a portion of the first catheter 160 and a portion of the second catheter 170 into a bodily lumen of a patient and can be manipulated to move, inflate, deflate, adjust, and/or otherwise reconfigure the portion of the first catheter 160 and the portion of the second catheter 170 within the bodily lumen. For example, the second catheter 170 can be moved relative to the first catheter 160, or vice-versa, to adjust a distance between a first occlusion element 168 coupled to a distal end portion of the first catheter 160 and a second occlusion element 178 coupled to a distal end portion of the second catheter 170. The device 100 can be used to isolate a segment of the bile duct within the space defined between the first occlusion element 168 and the second occlusion element 178. Thus, a procedure can then be performed within the isolated segment such as for example, delivering a therapeutic agent to the isolated segment.

The handle 110 has a proximal end portion 111 and a distal end portion 112. As described in further detail herein, the handle 110 can be arranged to enclose, house, and/or be disposed about a portion of the first catheter 160 and the second catheter 170. For example, the first catheter 160 and the second catheter 170 can each be coupled to the handle 110. A first port 120 and a second port 125 (collectively referred to herein as a first set of ports 128) are each disposed at the proximal end portion 111 of the handle 110. The first port 120 and the second port 125 can each define a lumen (not shown in FIGS. 2 and 3). In some embodiments, the first port 120 and the second port 125 can be formed monolithically or integrally with the first catheter 160. The first port 120 and the second port 125 can be any suitable size, shape, or configuration. For example, in some embodiments, the first port 120 and the second port 125 can extend from the proximal end portion 111 of the housing 110 such that at least a portion of the first port 120 and the second port 125 is accessible outside of the handle 110. Although not shown in FIGS. 2 and 3, the first port 120 and the second port 125 can each be physically and fluidically coupled to a device, mechanism, and/or the like, such as, for example, a source of an inflation medium as described in more detail below. For example, in some embodiments, the first port 120 and the second port 125 can each include a Luer-Lok® or the like that can physically and fluidically couple the first port 120 and/or the second port 125 to such a device. As described in further detail herein, the first set of ports 128 can be in fluid communication with at least a portion of the first catheter 160 to place at least the portion of the first catheter 160 in fluid communication with a device (e.g., a source of an inflation medium) coupled to the handle 110 via the first port 120 and/or the second port 125. For example, the lumen of the first port 120 can be in fluid communication with a first lumen defined by the first catheter 160 and the lumen of the second port 125 can be in fluid communication with a second lumen defined by the first catheter 160.

The distal end portion 112 of the handle 110 includes a third port 130, a fourth port 135, and a fifth port 140 (collectively referred to herein as a second set of ports 143). The second set of ports 143 can be any suitable arrangement such as, for example, described above with reference to the first set of ports 128. For example, the third port 130, the fourth port 135, and the fifth port 140 can each define a lumen (not shown in FIGS. 2 and 3) and can each include a Luer-Lok® or the like that can physically and fluidically couple the third port 130, the fourth port 135, and/or the fifth port 140 to any suitable attachment, device, mechanism, and/or the like. For example, the third port 130, the fourth port 135, and/or the fifth port 140 can each be coupled to an external device such as a device supplying a therapeutic agent, a device supplying an inflation medium or a device supplying an irrigation solution as described in more detail below with reference to, for example, device 400. In some embodiments, the second set of ports 143 includes the fifth port 140 and only one of the third port 130 and the second port 135.

As described in further detail herein, the second set of ports 143 can be in fluid communication with at least a portion of the second catheter 170 to place at least the portion of the second catheter 170 in fluid communication with such external devices coupled to the handle 110 via the third port 130, the fourth port 135, and/or the fifth port 140. For example, the third port 130 and/or the fourth port 135 can be coupled to and in fluid communication with a first lumen defined by the second catheter 170, and the fifth port 140 can be coupled to and in fluid communication with a second lumen defined by the second catheter 170. In some embodiments, the third port 130, the fourth port 135, and/or the fifth port 140 can be monolithically or integrally formed with the second catheter 170. Moreover, the second set of ports 143 can be coupled to or operably coupled to the actuator 150 as described in more detail herein.

The first catheter 160 (also referred to herein as "inner catheter") and the second catheter 170 (also referred to herein as "outer catheter") can be any suitable catheter device. For example, in some embodiments, the first catheter 160 and the second catheter 170 are multi-lumen catheters. As shown in FIG. 2, the first catheter 160 has a proximal end portion 161 and a distal end portion 162. The proximal end portion 161 of the first catheter 160 is disposed within a portion of the handle 110. More specifically, the proximal end portion 161 of the first catheter 160 can be fixedly disposed within the portion of the handle 110 to place the first catheter 160 in fluid communication with one or more of the ports 120 and 125 of the first set of ports 128. In some embodiments, the first catheter 160 can define a first lumen that can be physically and fluidically coupled to the first port 120 and a second lumen that can be physically and fluidically coupled to the second port 125. In other embodiments, a first catheter can be coupled to the handle and can be operably coupled to a first port and a second port (e.g., ports 120, 125) via an intervening structure such as, for example, flexible tubing or the like. In this manner, the first port 120 can be placed in fluid communication with a first lumen (not shown in FIGS. 2 and 3) defined by the first catheter 160, as described in further detail herein. Similarly, the second port 125 can be placed in fluid communication with a second lumen (not shown in FIGS. 2 and 3) defined by the first catheter 160. In some embodiments, the second port 125 and the second lumen of the first catheter 160 can receive a guidewire or the like, as described in further detail herein.

The distal end portion 162 of the first catheter 160 extends beyond a distal end portion of the handle 110 and includes the occlusion member 168. The occlusion member 168 can be any suitable device or mechanism that is configured to selectively limit, block, obstruct, or otherwise occlude a bodily lumen in which the occlusion member 168 is disposed. For example, in some embodiments, the occlusion member 168 can be an inflatable balloon or the like that can be transitioned between a collapsed (e.g., deflated) configuration and an expanded (e.g., inflated) configuration. In some embodiments, the arrangement of the first catheter 160 and the handle 110 can be such that the first port 120 is in fluid communication with the occlusion member 168. Thus, in use, the first port 120 can be fluidically coupled to a device that can supply a pressurized fluid (e.g., air, inert gas, or liquid) to the occlusion member 168 to transition the occlusion member 168 between a collapsed configuration and an expanded configuration, as described in further detail herein.

The second catheter 170 of the device 100 has a proximal end portion 171 and a distal end portion 172. As shown in FIGS. 2 and 3, the second catheter 170 is movably disposed about a portion of the first catheter 160. More specifically, the second catheter 170 can be, for example, a multi-lumen catheter and can be arranged such that the first catheter 160 is movably disposed within a first lumen (not shown in FIGS. 2 and 3) defined by the second catheter 170. The proximal end portion 171 can be movably disposed within the handle 110 such that a portion of the second catheter 170 is in fluid communication with the second set of ports 143. In some embodiments, the second catheter 170 can be physically and fluidically coupled to the third port 130 and the fourth port 135, and/or the fifth port 140. In other embodiments, the second catheter can be disposed within a handle and can be operably coupled to one or more ports via an intervening structure such as, for example, flexible tubing or the like. In this manner, the third port 130 and/or the fourth port 135 can be placed in fluid communication with the second lumen (not shown in FIGS. 2 and 3) defined by the second catheter 170, as described in further detail herein; the fifth port 140 can be placed in fluid communication with a third lumen (not shown in FIGS. 2 and 3) defined by the second catheter 170, as described in further detail herein.

The distal end portion 172 of the first catheter 170 extends beyond a distal end portion of the handle 110 and includes an occlusion member 178. The occlusion member 178 can be any suitable device or mechanism that is configured to selectively limit, block, obstruct, or otherwise occlude a lumen in which the occlusion member 178 is disposed. For example, in some embodiments, the occlusion member 178 can be substantially similar to the occlusion member 168 of the first catheter 160. In some embodiments, the arrangement of the second catheter 170 and the handle 110 can be such that the third port 130 and/or the fourth port 135 is in fluid communication with the occlusion member 178. Thus, in use, the third port 130 and/or the fourth port 135 can be fluidically coupled to a device that can supply a pressurized fluid (e.g., air, inert gas, or liquid) to the occlusion member 178 to transition the occlusion member 178 between a collapsed configuration and an expanded configuration, as described in further detail herein. In some embodiments, at least a portion of the occlusion member 178 can be selectively permeable to allow a biological agent to pass therethrough. Although not shown in FIGS. 2 and 3, in some embodiments, the distal end portion 172 of the second catheter 170 can define one or more openings. In such embodiments, the fifth port 140 can be fluidically coupled to a device that can supply irrigation, therapeutic material or agents, biological agents, and/or the like to a volume or region disposed between the occlusion member 168 of the first catheter 160 and the occlusion member 178 of the second catheter 170.

As described above, the actuator 150 of the device 100 can be operably coupled to the second set of ports 143. For example, in some embodiments, the actuator 150 is included in and/or coupled to the handle 110 and arranged relative to the second set of ports 143 to be operably coupled thereto. The actuator 150 can be any suitable device, mechanism, assembly, etc. that is movable between a first position relative to the handle 110, associated with the device 100 in the first configuration (FIG. 2), and a second position relative to the handle 110, associated with the device 100 in the second configuration (FIG. 3). Furthermore, with the actuator 150 operably coupled to the second set of ports 143, the actuator 150 can be operable in moving the second set of ports 143 between a first position relative to the handle 110 (e.g., the distal position) and a second position relative to the handle 110 (e.g., the proximal position), as indicated by the arrow AA in FIG. 3. Thus, when the second catheter 170 is coupled to the second set of ports 143, the actuator 150 can also move the second catheter 170 relative to the handle 110 and/or relative to the first catheter 160 as described in more detail below.

In some embodiments, the actuator 150 can be a push or pull slide that can move within a track (not shown in FIGS. 2 and 3) defined by the handle 110. In other embodiments, the actuator 150 can be coupled to an energy storage device (e.g., a spring, compressed gas, etc.) that is configured to move the actuator 150. For example, the actuator 150 can include a push button that allows a spring to transition from a compressed configuration towards an uncompressed configuration to move the actuator 150 relative to the handle 110. In other embodiments, a portion of the actuator 150 can be rotated to move the actuator 150 between its first position and its second position relative to the handle 110. With the second catheter 170 physically and fluidically coupled to the second set of ports 143 (as described above), the movement of the actuator 150 can move the second catheter 170 relative to the handle 110. More specifically, the proximal end portion 171 of the second catheter 170 can be movably disposed within the handle 110 (as described above) such that when the actuator 150 is moved from its first position to its second position, the proximal end portion 171 of the second catheter 170 is moved from a first position relative to the handle 110 (e.g., FIG. 2) to a second position relative to the handle 110 (e.g., FIG. 3).

With the second catheter 170 movably disposed about the first catheter 160, the movement of the actuator 150 moves the second catheter 170 relative to the first catheter 160. For example, when the device 100 is in the first configuration, a first distance D1 is defined between the occlusion member 168 of the first catheter 160 and the occlusion member 178 of the second catheter 170. Therefore, with the first catheter 160 fixedly disposed within the handle 110, the movement of the second catheter 170 in the proximal direction (e.g., the AA direction) increases the distance between the occlusion member 168 of the first catheter 160 and the occlusion member 178 of the second catheter 170 to a second distance D2, as shown in FIG. 3.

In use, a guidewire (not shown) can be inserted into the second port 125 and through a lumen defined by the first catheter 160. In this manner, the guidewire can be advanced through a bodily lumen and the device 100 can be manipulated to advance the first catheter 160 along the guidewire to place the distal end portion 162 of the first catheter 160 and the distal end portion 172 of the second catheter 170 at a target location within the bodily lumen. Once at the target location, the actuator 150 can be moved in the AA direction (e.g., the proximal direction) to define a desired distance between the occlusion member 168 of the first catheter 160 and the occlusion member 178 of the second catheter 170, thereby placing the device 100 in the second configuration (FIG. 3). As described above, an inflation source can be coupled to the second port 125 of the first catheter 160 and the same inflation source or a second inflation source can be coupled to the third port 130 and/or the fourth port 135 of the second catheter 170. With the desired distance defined between the occlusion members 168 and 178, the inflation source(s) can be used to inflate the occlusion members 168 and 178. Thus, the occlusion members 168 and 178 can be transitioned from the collapsed (e.g., deflated) configuration to the expanded (e.g., inflated) configuration to substantially isolate a segment of the bodily lumen disposed therebetween. With the occlusion members 168 and 178 substantially occluding the bodily lumen, a biological or therapeutic agent can be delivered to the substantially isolated segment via the fourth port 135. For example, the biological or therapeutic agent can be delivered through the fourth port 135 into a lumen of the second catheter that is in fluid communication with the opening (see, e.g., opening 479 in FIG. 20) defined by the distal end portion 172 of the second catheter 170. In some instances, the substantially isolated segment can be irrigated by coupling an irrigation source to the fifth port 140. Thus, the irrigation is delivered to the substantially isolated segment via the opening (described above) defined by the distal end portion 172 of the second catheter 170.

Figure 4:
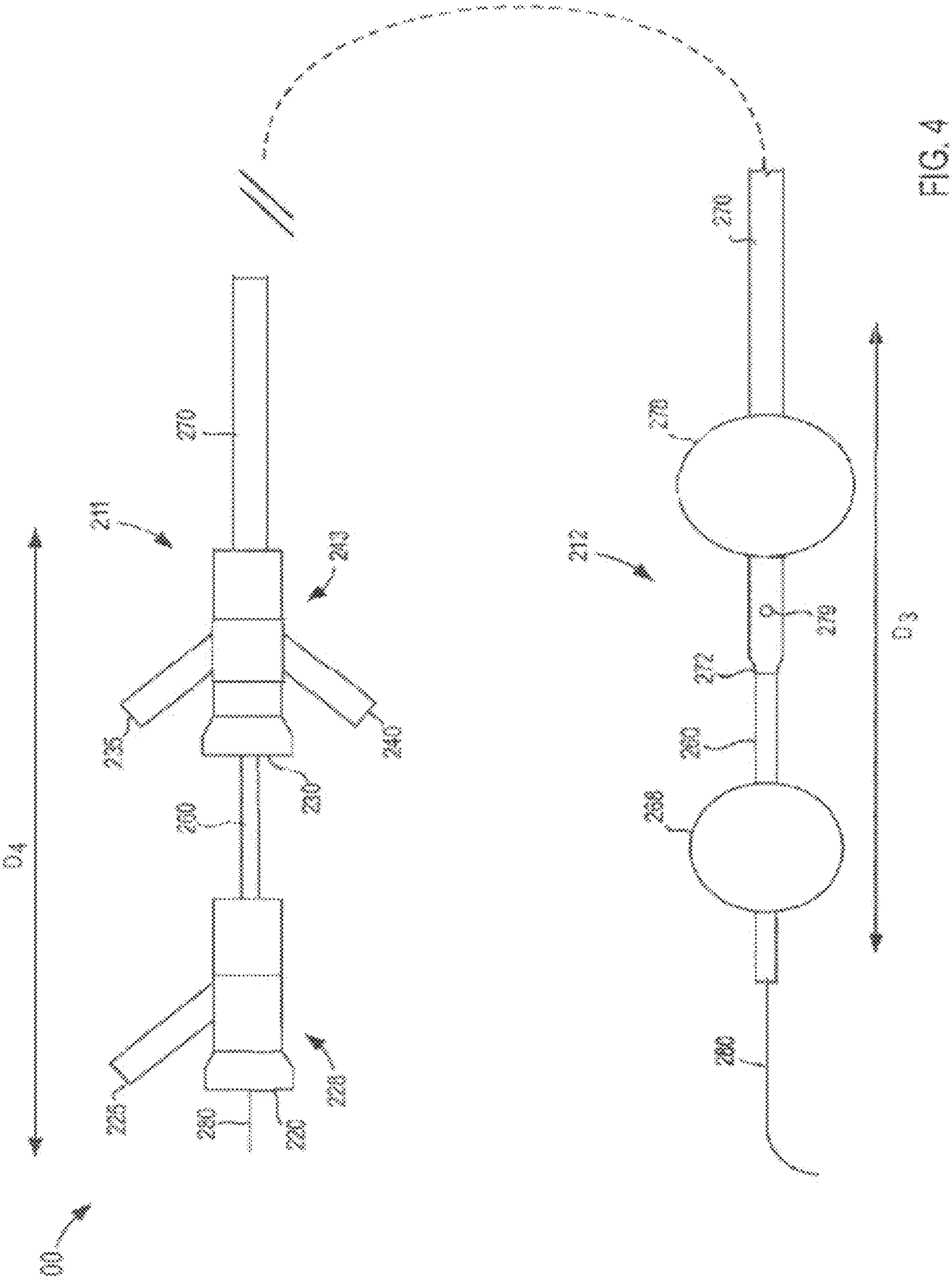
FIG. 4 is a side view of a multi-occlusion catheter insertion device according to an embodiment, shown in a dilated configuration.

FIGS. 4-11 illustrate a dilation catheter 200 according to an embodiment. FIG. 4 is a side view of the dilation catheter device 200 (also referred to herein as "catheter device"). In this embodiment, dilatation of two balloons is used to occlude a desired length of an artery such as, for example, the splenic artery 40 (see, e.g., FIG. 2). Specifically, the catheter device 200 includes a first catheter 260 (also referred to herein as "inner catheter") and a second catheter 270 (also referred to herein as "outer catheter"), a first Y-adaptor 228 (also referred to herein as "first set of ports") and a second Y-adaptor 243 (also referred to herein as "second set of ports"), a first occlusion element 268 (also referred to herein as "dilation element", "occluder," or "distal occlusion element"), and a second occlusion element 278 (also referred to herein as "dilation element", "occluder," or "proximal occlusion element") each configured to occlude a portion of an artery. The first occlusion element 268 is coupled to the first catheter 260 and the second occlusion element 278 is coupled to the second catheter 270.

The occlusion elements 268 and 278 can each be moved between a collapsed configuration (also referred to as "retracted configuration") for insertion of the catheter device 200 into a body of a patient (e.g., into an artery) and an expanded configuration (also referred to as "dilated configuration" or "inflated configuration") for occluding a portion of an artery. The occlusion elements 268 and 278 when in the collapsed configuration have a smaller outer perimeter (or diameter) than when in the expanded configuration.

The catheter device 200 includes a distal end portion 212 and a proximal end portion 211. In this embodiment, the occlusion elements 268 and 278 are expandable balloons coupled to an outer surface of the first catheter 260 and an outer surface of the second catheter 270, respectively, and are disposed at the distal end portion 212 of the catheter device 200. The catheter device 200 is shown in a dilated configuration in FIG. 4 with the occlusion elements 268 and 278 (i.e., balloons) in their expanded configuration (i.e., inflated, dilated).

Figure 5:
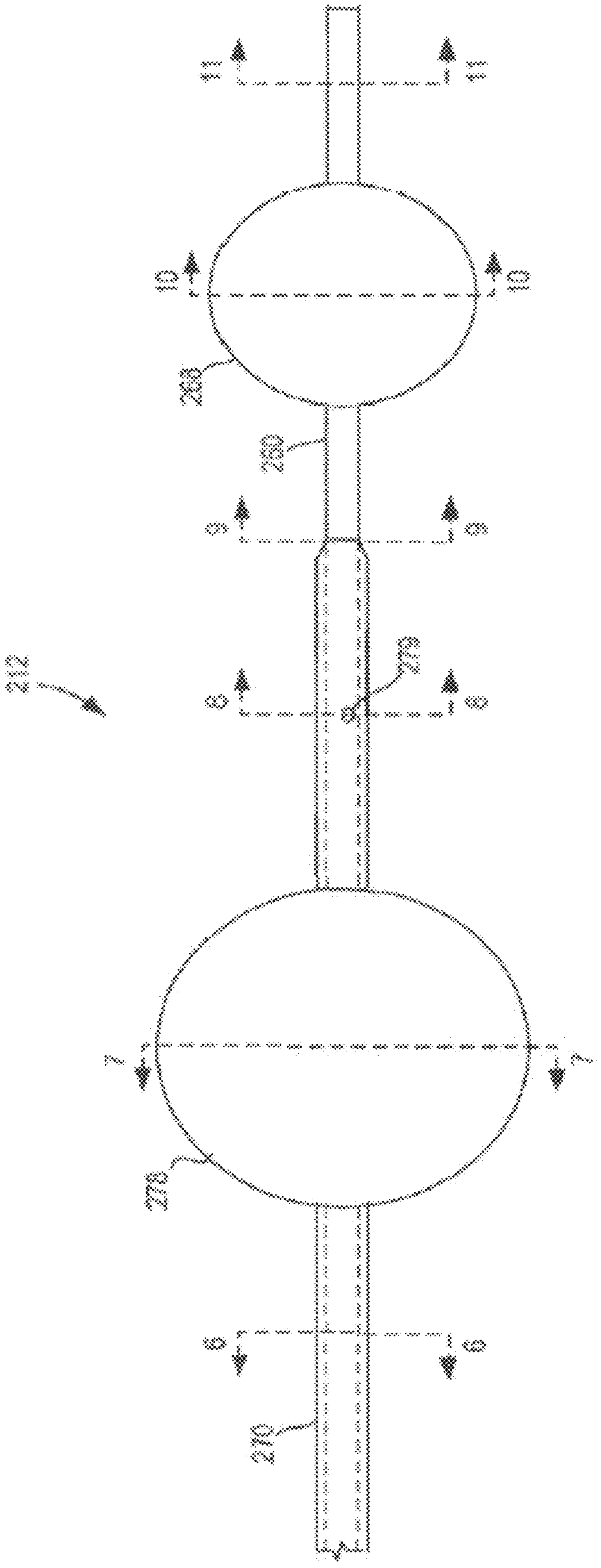
FIG. 5 is a side view of a portion of the multi-occlusion catheter insertion device of FIG. 4.

FIG. 5 is a side view of the distal end portion 212 of the catheter device 200 (e.g., a distal end portion of the first catheter 260 and the second catheter 270) and FIGS. 6-11 illustrate cross-sections at various locations along the distal end portion 212 of the catheter device 200 to illustrate the various lumens of the catheter device 200. As shown in FIGS. 6-11, the first catheter 260 defines a first lumen 265 and a second lumen 263 that each can extend a length of the first catheter 260. The first lumen 265 can be configured to receive a guidewire 280 (shown, for example, in FIG. 4). The second lumen 263 can be used to communicate an inflation medium to and from the first occlusion element 268 via an aperture 264 in fluid communication with the first occlusion element 268 (see, e.g., FIG. 10).

Figure 6:
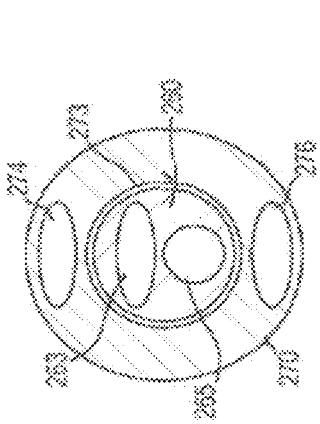
FIGS. 6-11 are each a cross-sectional view of a different portion of the multi-occlusion catheter insertion device of FIG. 4, taken along lines 6-6, 7-7, 8-8, 9-9, 10-10, and 11-11, respectively, in FIG. 5.
Figure 7:
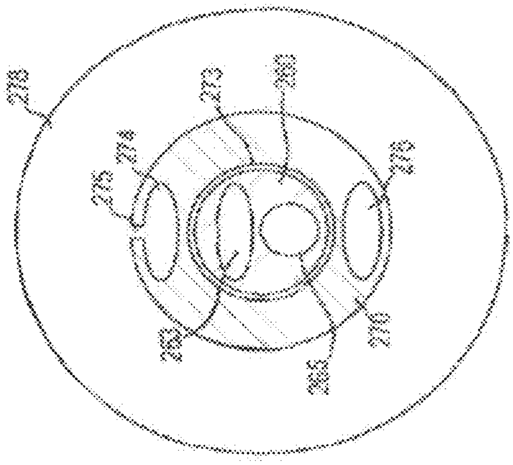
Figure 8:
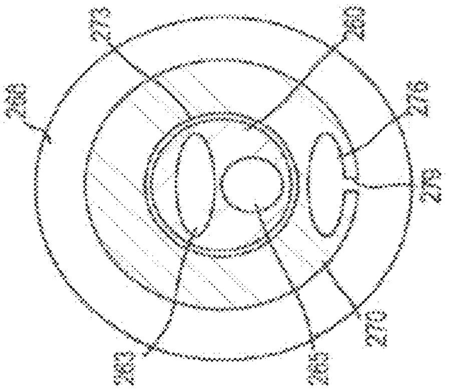
Figure 9:
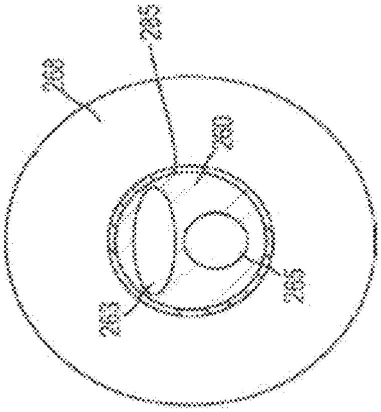
Figure 10:
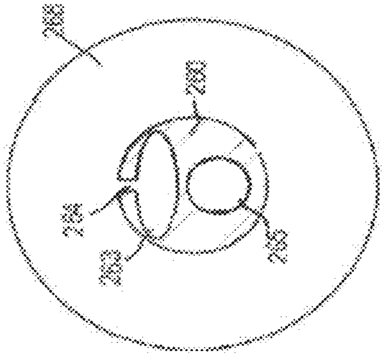
Figure 11:
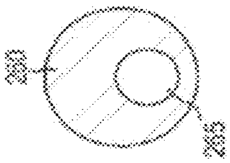

As shown, for example, in FIGS. 6 and 7, the second catheter 270 defines a first lumen 274, a second lumen 273, and a third lumen 276. The first lumen 274 can be used to communicate an inflation medium to and from the second occlusion element 278 via an aperture 275 in fluid communication with the second occlusion element 278 (see, e.g., FIG. 7). The second lumen 273 is configured to slidably receive at least a portion of the first catheter 260 therethrough, as shown in FIGS. 6-9. The third lumen 276 can terminate and be in fluid communication with an infusion aperture 279 near a distal end 272 of the second catheter 270 (see, e.g., FIG. 8). The infusion aperture 279 can be used to communicate a cell/biological/therapeutic material to a desired location within a body/artery of a patient.

The first Y-adaptor 228 is coupled to the first catheter 260 and includes two ports 220 and 225, as shown in FIG. 4. The port 220 defines a lumen (not shown) that is in fluid communication with the first lumen 263 of the catheter 260 and can be used to communicate an inflation medium to the first occlusion element 268 through the second lumen 263. For example, a source of an inflation medium (not shown) can be coupled to the catheter device 200 via the port 220 of the first Y-adaptor 228. The port 225 defines a lumen (not shown) that is in fluid communication with the second lumen 265 of the first catheter 260 (see, e.g., FIGS. 6-11) and can be used for introduction of the guidewire 280 into the second lumen 265.

The second Y-adapter 243 is coupled to the second catheter 270 and includes three ports 230, 235 and 240, as shown in FIG. 4. The port 230 defines a lumen (not shown) that is in fluid communication with the second lumen 273 of the second catheter 270 (see, e.g., FIGS. 6-11) and can receive the first catheter 260 therethrough. The port 235 defines a lumen (not shown) that is in fluid communication with the first lumen 274 of the second catheter 270 and can be used to communicate an inflation medium to and from the second occlusion element 278 in a similar manner as described above for port 225 and lumen 263. The port 240 defines a lumen (not shown) that is in fluid communication with the third lumen 276 of the second catheter 270 (see e.g., FIGS. 6-11) and can be used to introduce cells/biological/therapeutic materials into and through the third lumen 276 and out through the infusion aperture 279.

The catheter device 200 can also include a seal element 285 (see, e.g., FIG. 9) (also referred to a as a "seal", "sealing element", "selective sealing element", or "filter-ring") disposed at or near a distal end 272 of the second catheter 270. The seal element 285 can prevent the entry of cells and or biologics that have been injected into an artery from flowing back into the lumen 273. By doing so, a maximum number of cells can be delivered to the treatment area and improve engraftment efficiency. The seal element 285 can be for example, a ring, a membrane or other known sealing elements used in medical devices.

The slidable coupling of the first catheter 260 within the second lumen 273 of the second catheter 270 allows a collective length of the first catheter 260 and the second catheter 270 to be adjusted by slidably moving the first catheter 260 and the second catheter 270 relative to each other. Because the first occlusion element 268 is coupled to the first catheter 260 and the second occlusion element 278 is coupled to the second catheter 270, the slidable adjustment of the first catheter 260 and the second catheter 270 can thus allow adjustment of a distance between the second occlusion element 278 and the first occlusion element 268. The second lumen 273 of the second catheter 270 can be sized to receive the first catheter 260 with sufficient clearance to allow for ease of sliding/adjustment.

In use, the catheter device 200 can be placed at a desired location within an artery, such as for example, within a splenic artery 40 (see e.g., FIG. 1) and used to infuse a cell/biological material to a pancreas 30. A length of the first catheter 260 and the second catheter 270 can be adjusted such that a selected portion (e.g., a pancreatic portion) of the splenic artery 40 is isolated between the first occlusion element 268 and the second occlusion element 278. A cell/biologic material can be injected through the catheter device 200 and into the isolated region of the splenic artery 40.

The infusion of a cell/biological agent can occur in the localized region surrounding the isolated region or segment of vessel 40. In some instances, however, the presence of one or more additional, side-branching vessels forming a flow-restricting configuration in the isolated region of vessel 40 can allow infusion to occur in a larger semi-localized region. To allow the operator to accommodate the location of these side branches to fall within the isolated region, the first catheter 260 can be configured such that it is slidably associated with the second catheter 270 and the space between (e.g., distance between) occlusion elements 268 and 278 can be varied according to the circumstances of the desired treatment. The positioning of the distal occlusion element 268 within an artery can be individualized based on the specific anatomy to allow an enclosed or isolated area between the two occlusion elements 268 and 278 with a linear length ranging, for example, from 3 cm to 22 cm.

The cells targeted to the pancreas 30 (see e.g., FIG. 1) can be infused through infusion port 240, traverse through the third lumen 276, and exit through the infusion aperture 279 into the area isolated between the two occlusion elements 268 and 278. The catheter device 200 can be configured to enable delivery of target cells, such as insulin producing beta cells, and autologous stem cells (mesenchymal, bone marrow, and others) to blood vessels in communication with the pancreas in situ. The infusion pressure in the isolated blood vessel region can be measured with pressure monitoring through the infusion lumen of the catheter (with a manometer (not shown) in line with infusion port 279). The pressure in the third lumen 276 can be based on the size of the cells being delivered, on the flow rate, the viscosity of the solution, and/or flow resistance of the third lumen 276 of second catheter 270. The flow resistance of the catheter device 200 can in turn be determined based on, for example, the inner coating material, the size and the length of the third lumen 276, the size of the third port 240, and/or the size of the distal infusion aperture 279. The catheter device 200 can allow for rapid infusion of cells (e.g., up to 2 milliliter per second (ml/sec)). In some applications, the rapid infusion of cells can enhance uptake and eventual engraftment. Smaller aperture size (e.g., the infusion aperture 279), lumen size (e.g., the third lumen 276), and increased flow resistance may cause "sludging" of cells, leading to poor intra-arterial flow and diminished uptake. Lastly, the infusion aperture 279 and luminal design of the catheter device 200 can be configured to minimize risk of mechanical cell damage during the infusion process.

Figure 12:
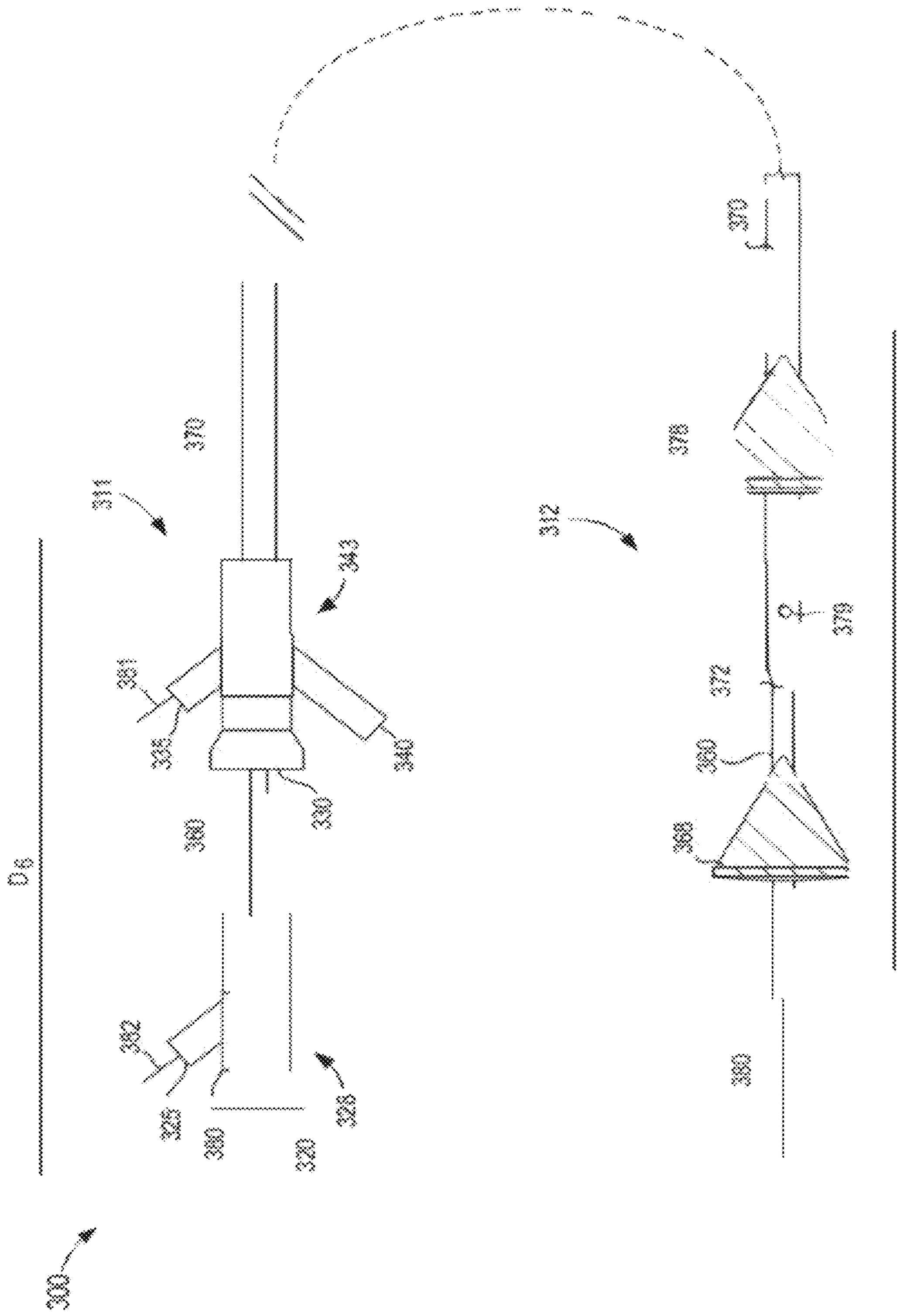
FIG. 12 is a side view of a multi-occlusion catheter insertion device according to an embodiment.

FIG. 12 illustrates an embodiment of a catheter device 300 that uses two filter elements, instead of expandable balloons to occlude and isolate the area of interest for infusion of cells or chemotherapeutic agents, without inhibiting the flow of plasma through the isolated area. The filter elements can be formed with, for example, a medical mesh material. The size of the pores of the filter elements can be, for example, about 2 microns (μm) or less in length, which can inhibit cells from passing through the filter element, but not impede serum/plasma and other components from passing through the filter element. The catheter device 300 can be used for the same or similar functions as described above for catheter device 200. For example, the catheter device 300 can be used for introduction of cells or other biologic or therapeutic material into a desired location within a patient's body, such as within a splenic artery.

The catheter device 300 includes a first catheter 360 and a second catheter 370 that can be slidably coupled together as described above for catheter device 200, a first Y-adaptor 328 (also referred to herein as "first set of ports") coupled to the first catheter 360, a second Y-adaptor 343 (also referred to herein as "second set of ports") coupled to the second catheter 370, a first occlusion element 368 (also referred to herein as "dilation element", "occluder", "distal occlusion element") and a second occlusion element 378 (also referred to herein as "dilation element", "occluder", "proximal occlusion element") to occlude a portion of an artery. The first occlusion element 368 is coupled to the first catheter 360 and the second occlusion element 378 is coupled to the second catheter 370.

In this embodiment, the occlusion elements 368 and 378 are filter elements that can be moved between a collapsed configuration (also referred to as "retracted configuration" or "closed configuration") for insertion of the catheter device 300 into a body of a patient (e.g., into an artery) and an expanded configuration (also referred to as "dilated configuration" or "open configuration"), as shown in FIG. 12, for occluding a portion of an artery. The occlusion elements 368 and 378 when in the collapsed configuration have a smaller outer perimeter (or diameter) than when in the expanded configuration.

Figure 13:
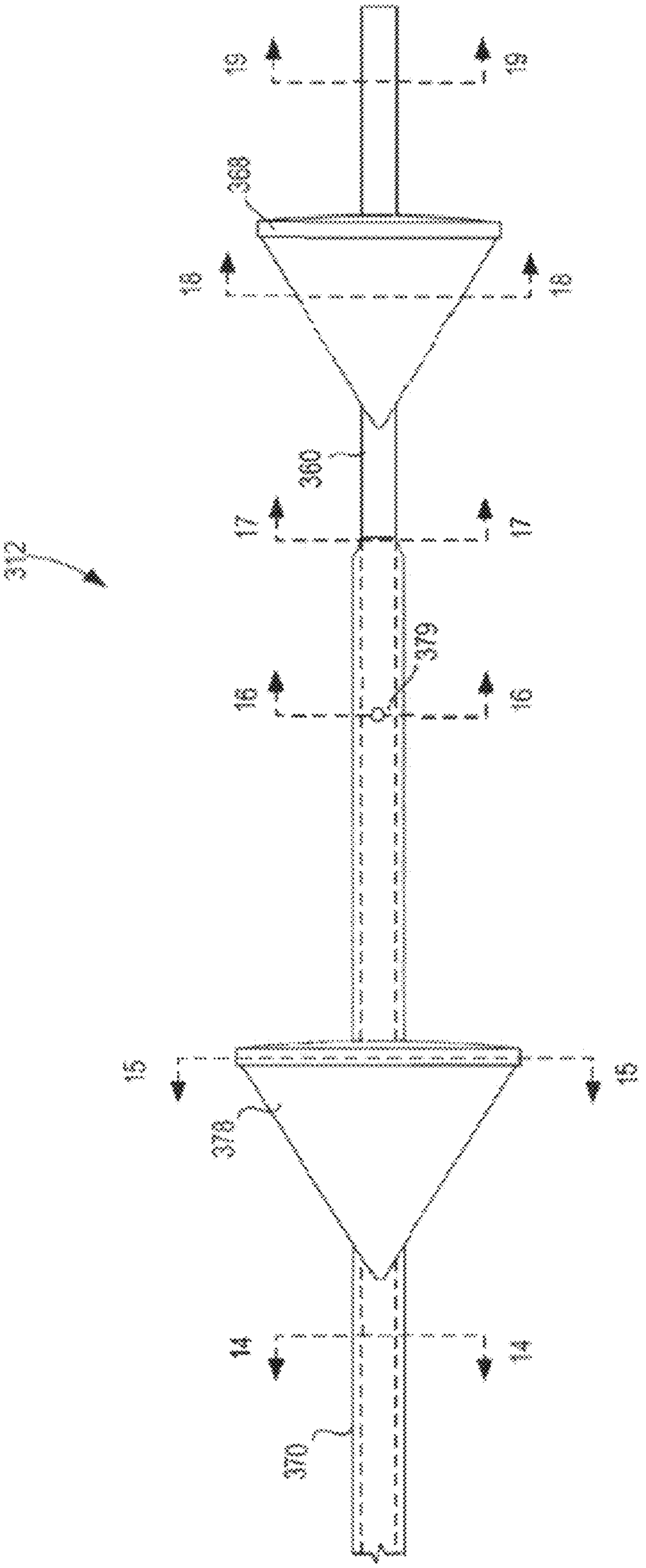
FIG. 13 is a side view of a portion of the multi-occlusion catheter insertion device of FIG. 12.
Figure 14:
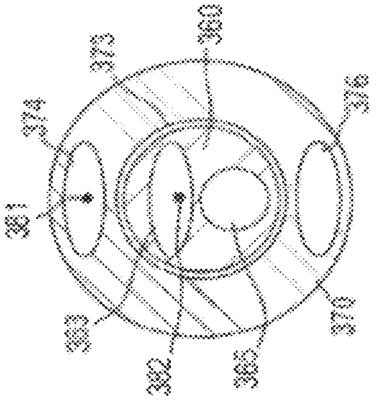
FIGS. 14-19 are each a cross-sectional view of a different portion of the multi-occlusion catheter insertion device taken along lines 14-14, 15-15, 16-16, 17-17, 18-18, and 19-19, respectively, in FIG. 13.
Figure 15:
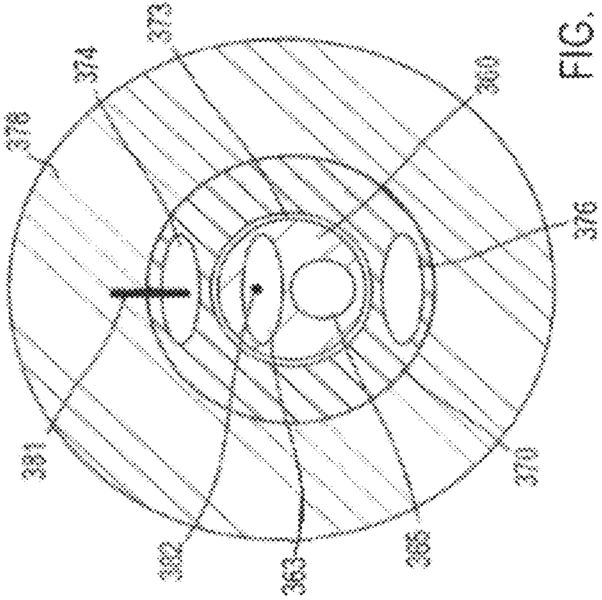
Figure 16:
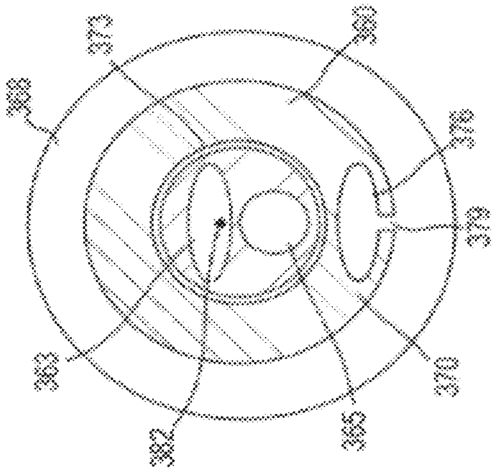
Figure 17:
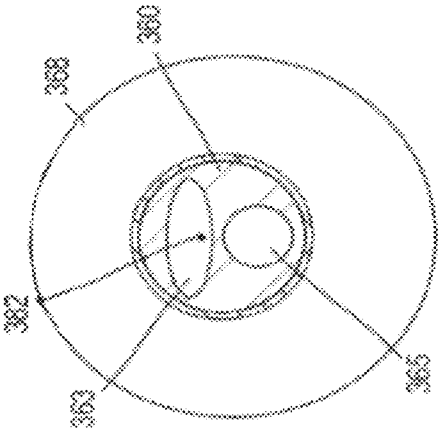
Figure 18:
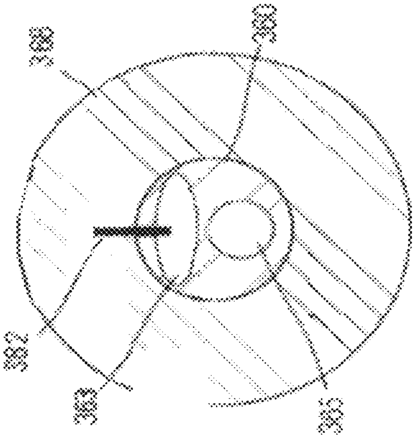
Figure 19:
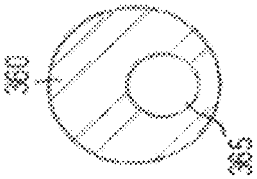

The catheter device 300 includes a distal end portion 312 and a proximal end portion 311. FIG. 13 is a side view of the distal end portion 312 of the catheter device 300 and FIGS. 14-19 illustrate cross-sections at various locations along the distal end portion 312 of the catheter device 300. As shown in FIGS. 14-19, the first catheter 360 defines a first lumen 363 and a second lumen 365 that each can extend a length of the first catheter 360. The first lumen 363 can be configured to receive a wire deployment device 382 that can be coupled to the filter element 368 and configured to move the filter element 368 from its expanded or open configuration and its collapsed or closed configuration. The second lumen 365 can be configured to receive a guidewire 380 (shown in FIG. 12).

The second catheter 370 defines a first lumen 373, a second lumen 374, and a third lumen 376. The first lumen 373 is configured to slidably receive at least a portion of the first catheter 360 therethrough. The second lumen 374 can be configured to receive a wire deployment device 381. The wire deployment device 381 can be coupled to the filter element 378 and used to move the filter element 378 between its expanded or open configuration and its collapsed or closed configuration. The third lumen 376 can terminate and be in fluid communication with an infusion aperture 379 (see, e.g., FIG. 16) near a distal end 372 of the second catheter 370. The infusion aperture 379 can be used to communicate, for example, a cell or cells (or other therapeutic or biologic material) to a desired location within a body of a patient.

The first Y-adaptor 328 includes a port 320 and a port 325 as shown in FIG. 12. The port 320 defines a lumen (not shown) that is in fluid communication with the first lumen 363 of the catheter 360. The port 325 defines a lumen (not shown) that is in fluid communication with the second lumen 365 of the catheter 360, and can be used for introduction of the guidewire 380 into the second lumen 365. The second Y-adapter 343 includes three ports 330, 335 and 340, as shown in FIG. 12. The port 330 defines a lumen (not shown) that is in fluid communication with the first lumen 373 of the second catheter 370 and can receive the first catheter 360 therethrough. The port 335 defines a lumen (not shown) that is in fluid communication with the second lumen 374 of the second catheter 370, and the port 335 defines a lumen (not shown) that is in fluid communication with the third lumen 376 of the second catheter 370.

The filter elements 368 and 378 can each be shaped as a cone when in their expanded or open configurations as shown in FIGS. 12 and 13. The filter elements 368 and 378 can each be sized when in their expanded or open configurations to meet the size of a particular vessel diameter in which the catheter device 300 is to be deployed. After infusion of cells or a therapeutic/biologic material through the catheter device 300, the filter elements 368 and 378 can be collapsed to a smaller size for removal of the catheter device 300 from the patient.

In some embodiments, a diameter of the occlusion elements (e.g., 268, 278, 368, and 378) when expanded within an artery, such as, for example, the splenic artery 40, can be adjustable to meet anatomical variations including a) individual variability in the size of the splenic artery 40 and b) end to end variation as the artery size can taper down between the two ends of the artery. As such, in some embodiments, to allow successful isolation of the area for treatment, the proximal occlusion element (e.g., the balloon 278 and/or the filter element 378) can be sized (e.g., have an outer diameter or outer perimeter) between, for example, 3-12 mm and the distal occlusion element (e.g., the balloon 268 and/or the filter element 368) between, for example, 3-12 mm. The proximal occlusion element can be larger than the distal occlusion element, smaller than the distal occlusion element, or the same size as the distal occlusion element.

Referring now to FIGS. 20-29, a multi-lumen catheter insertion device 400 is illustrated according to an embodiment. The multi-occlusion catheter insertion device 400 (also referred to herein as "catheter device" or "device") includes a handle 410, an actuator 450, a first catheter 460 (also referred to herein as "inner catheter"), and a second catheter 470 (also referred to herein as "outer catheter") and can be movable between a first configuration and a second configuration. As described in further detail herein, the device 400 can be grasped by a user (e.g., a doctor, physician, surgeon, technician, etc.) and manipulated substantially single handedly to insert a portion of the first catheter 460 and a portion of the second catheter 470 into a bodily lumen of a patient and to move, inflate, deflate, adjust, and/or otherwise reconfigure the portion of the first catheter 460 and the portion of the second catheter 470 within the bodily lumen. For example, the second catheter 470 can be moved relative to the first catheter 460, and vice-versa, to adjust a distance between a first occlusion element 468 coupled to a distal end portion of the first catheter 460 and a second occlusion element 478 coupled to a distal end portion of the second catheter 470. The device 400 can be used to isolate a segment of a bodily lumen within the space or region defined between the first occlusion element 468 and the second occlusion element 478. Thus, a procedure can then be performed within the isolated segment such as, for example, delivering a cell or a therapeutic/biological agent to the isolated segment.

The handle 410 of the device 400 can be any suitable shape, size, or configuration. For example, in some embodiments, the handle 410 can have a shape and size that can enhance the ergonomics of the device 400. More specifically, the handle 410 has a proximal end portion 411, a distal end portion 412, and a medial portion 413 that can be shaped in such a manner as to be easily gripped by a user (e.g., a doctor, physician, surgeon, technician, etc.). In some embodiments, the handle 410 can include a grip section 417 (see, e.g., FIG. 21) or the like that can have, for example, a rough surface finish, detents, protrusions, or the like that can enhance the ergonomics of the handle 410. In other embodiments, the grip section can be, for example, an insert, an over-mold, or the like that is formed from a relatively deformable material and that can have a relatively high coefficient of friction, thereby enhancing the ergonomics of the handle 410.

The proximal end portion 411 of the handle 410 includes a first port 420 and a second port 425 collectively referred to herein as a first set of ports 428). The first port 420 and the second port 425 can be any suitable size, shape, or configuration. In some embodiments, the first port 420 and the second port 425 can be coupled together via any suitable method (e.g., an adhesive, ultrasonic welding, mechanical fastener, and/or the like). In other embodiments, the first port 420 and the second port 425 can be monolithically formed.

Figure 20:
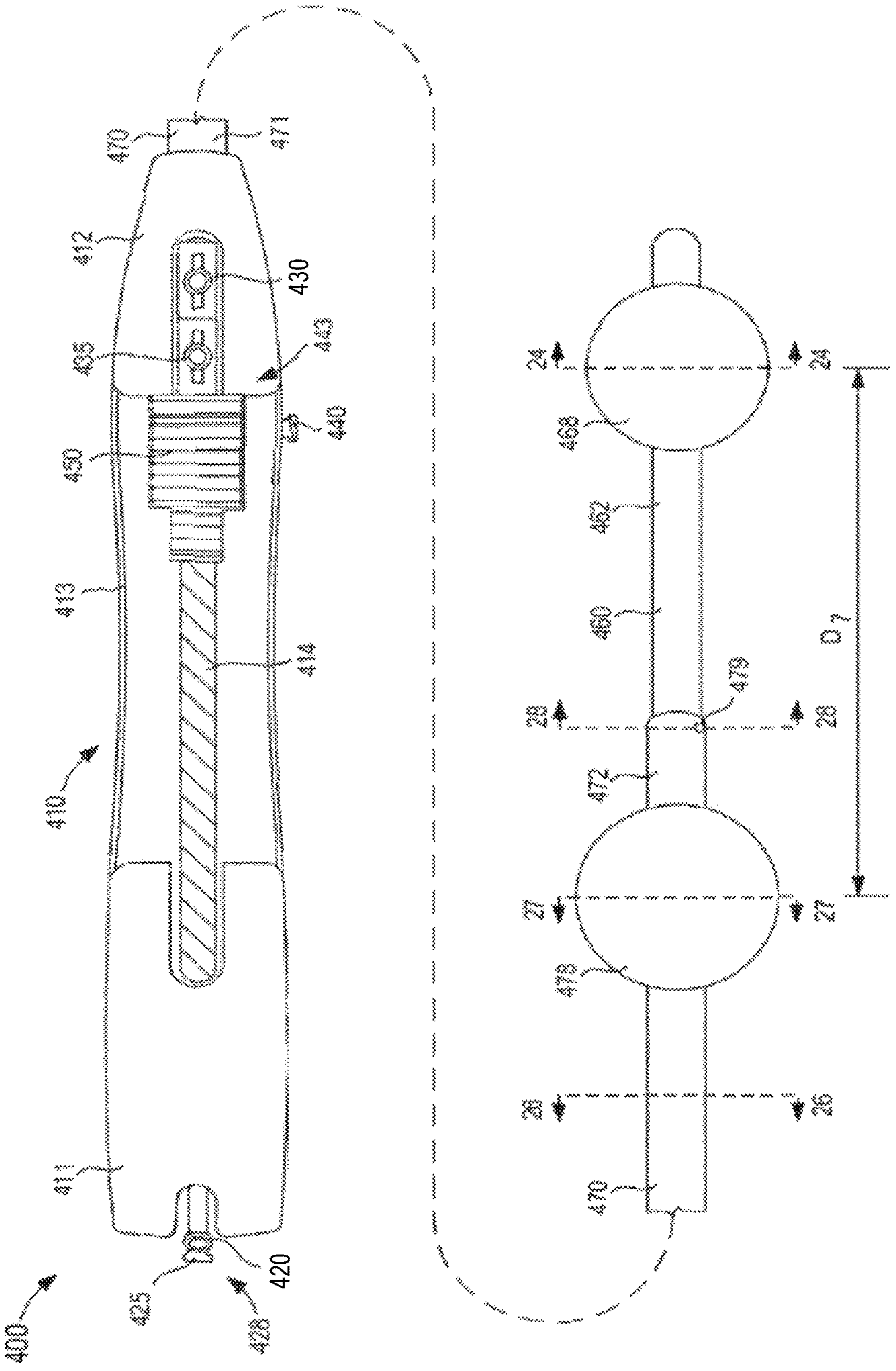
FIG. 20 is a top view of a multi-occlusion catheter insertion device according to an embodiment, in a first configuration.
Figure 21:
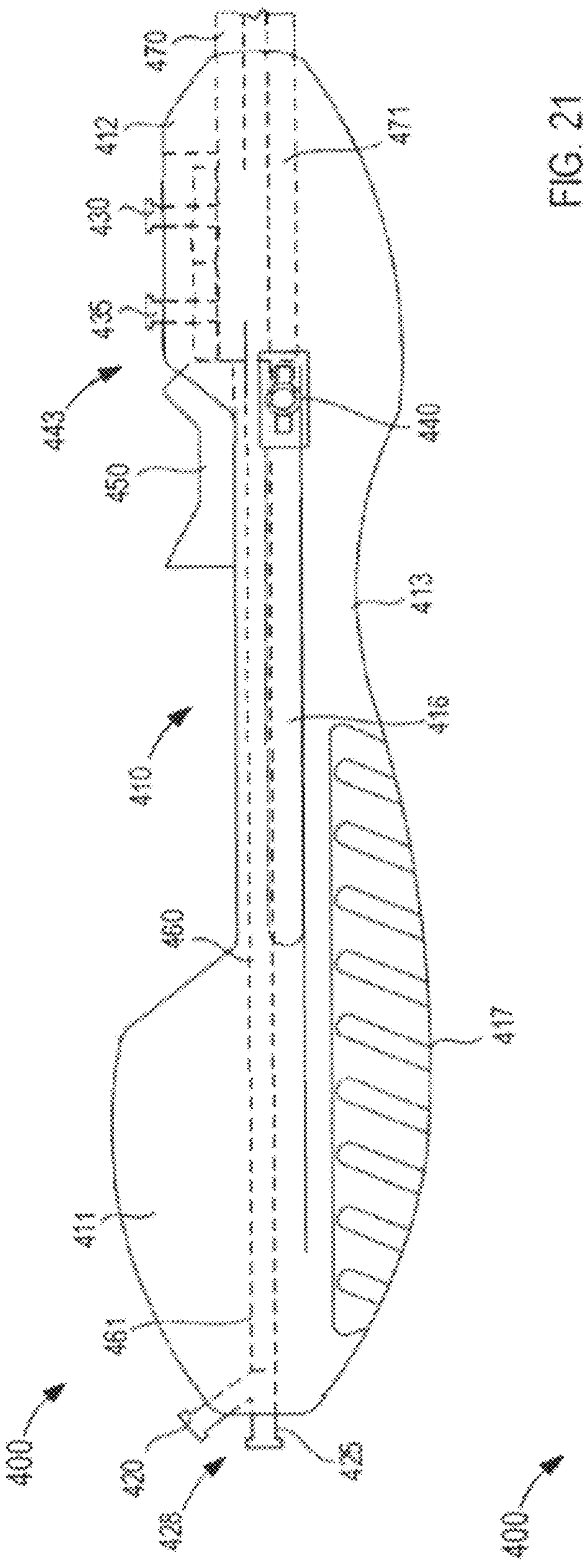
FIG. 21 is a side view of a handle included in the multi-occlusion catheter insertion device of FIG. 20.

The first port 420 and the second port 425 can extend from the proximal end portion 411 of the handle 410 such that at least a portion of the first port 420 and the second port 425 is accessible, as shown in FIGS. 20 and 21. In some embodiments, the first set of ports 428 can be, for example, a first Y-adapter, substantially similar to the Y-adapter 228 and/or 328. In other embodiments, a first port and a second port can be, for example, substantially parallel in a stacked configuration. In yet other embodiments, a handle can include a first port and a second port that are substantially coaxial and arranged in a substantially concentric configuration such that at least a portion of the first port is disposed within the second port, or vice versa.

Although not shown in FIGS. 14-29, the first port 420 and the second port 425 can be physically and fluidically coupled to an exterior device, mechanism, and/or the like as described above, for example, with reference to insertion device 100. For example, the first port 420 and the second port 425 can each define a lumen (described in more detail below) in fluid communication with such a device. The first port 420 and the second port 425 can each include a Luer-Lok® and/or any other attachment mechanism that can physically and fluidically couple the first port 420 and/or the second port 425 to any suitable device either directly or indirectly (e.g., by an intervening structure such as a flexible tubing to the like). The first set of ports 428 can be physically and fluidically coupled to the first catheter 460 such that when an external device is coupled to the handle 410 via the first port 420 and/or the second port 425, at least the portion of the first catheter 460 is placed in fluid communication with that external device via the first port 420 and/or the second port 425. For example, the first port 420 can be coupled to a device that can, for example, supply a pressurized fluid (e.g., an inert gas, air, saline, water, and/or any other suitable fluid in gaseous or liquid form) that can flow through the first port 420 to be delivered to a portion of the first catheter 460, as described in further detail herein. Furthermore, the second port 425 can be coupled to a device that can advance a guidewire or the like through the second port 425 and into a portion of the first catheter 460, as described in further detail herein. In some embodiments, a guidewire or the like can be manually inserted through the second port 425 without the use of an external device.

The distal end portion 412 of the handle 410 includes a third port 430, a fourth port 435, and a fifth port 440 (collectively referred to as a second set of ports 443). In some embodiments, the second set of ports 443 includes the fifth port 440 and only one of the third port 430 and the second port 435. The second set of ports 443 can be any suitable size, shape, or configuration as described above with reference to the first set of ports 428. For example, the second set of ports 443 can be, for example, monolithically and/or unitarily formed. In some embodiments, the second set of ports 443 can be monolithically formed with the catheter 470. In some embodiments, the second set of ports 443 can be formed with and/or coupled to any suitable structure or component of the handle 410 such that the second set of ports 443 can be moved relative to the handle 410 as described in more detail below.

The third port 430, the fourth port 435, and the fifth port 440 can each include a Luer-Lok® and/or any other attachment mechanism that can physically and fluidically couple the third port 430, the fourth port 435, and/or the fifth port 440 to any suitable attachment, device, mechanism, and/or the like. The second set of ports 443 can be physically and fluidically coupled to the second catheter 470 such that when an external device is coupled to the handle 410 via the third port 430, the fourth port 435, and/or the fifth port 440, at least a portion of the second catheter 470 is placed in fluid communication with that external device. For example, in some embodiments, the third port 430 and/or the fourth port 435 can be coupled to a device that can supply a pressurized fluid (as described above) that can flow through the third port 430 and/or the fourth port 435, respectively, to be delivered to a portion of the second catheter 470, as described in further detail herein. In some embodiments, the fifth port 440 is coupled to, for example, an infusion device that is configured to deliver a biological or therapeutic agent and/or other suitable drug formulation to a target tissue via the fifth port 440 and a portion of the second catheter 470. In some embodiments, the fifth port 440 can be coupled to, for example, an irrigation device that can deliver an irrigation fluid to, for example, an isolated segment of a bodily lumen via the fifth port 440 and a portion of the second catheter 470. In some embodiments, the fifth port 440 can be coupled to, for example, the infusion device configured to deliver the biological agent and/or other suitable drug formulation, as described in further detail herein.

Figure 22:
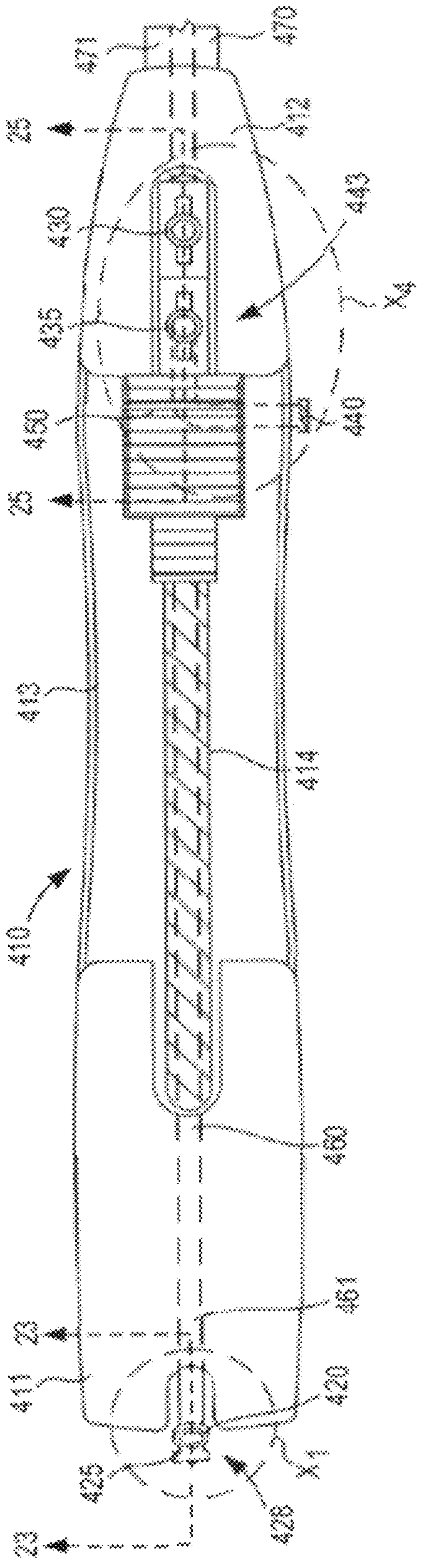
FIG. 22 is a top view of a handle included in the multi-occlusion catheter insertion device of FIG. 20.

As shown in FIGS. 20-22, the handle 410 defines a first track 414 and a second track 416. The first track 414 slidably receives a portion of the actuator 450. More specifically, at least a portion of the actuator 450 can extend through the track 414, thereby allowing a user to engage the actuator 450. As such, the track 414 can define a path along which the actuator 450 can be moved between a first position relative to the handle 410 and a second position relative to the handle 410, as described in further detail herein. In a similar manner, the second track 416 slidably receives a portion of the fifth port 440. In this manner, the fifth port 440 can extend through the second track 416 to be accessed by a user. Moreover, the second track 416 can define a path along which the fifth port 440 can be moved, as described in further detail herein.

Although the device 400 is particularly shown in FIGS. 20-29, the arrangement of the first set of ports 428, the second set of ports 443, the first track 414 and the second track 416 can be arranged along a surface of the handle 410 in various orientations. For example, although the first track 414 is shown as being defined by a top surface of the handle 410 (see, e.g., FIG. 20) and the second track 416 as being defined by a side surface of the handle 410 (see, e.g., FIG. 21), in other embodiments, a first track configured to receive an actuator can be defined by a side surface of a handle and a second track configured to receive a fifth port can be defined by a top surface of the handle. Similarly, while the first set of ports 428 and the second set of ports 443 are shown extending from the handle 410 in a specific orientation, the first set of ports 428 and/or the second set of ports 443 can be oriented in any suitable manner relative to a surface of the handle 410.

Figure 29:
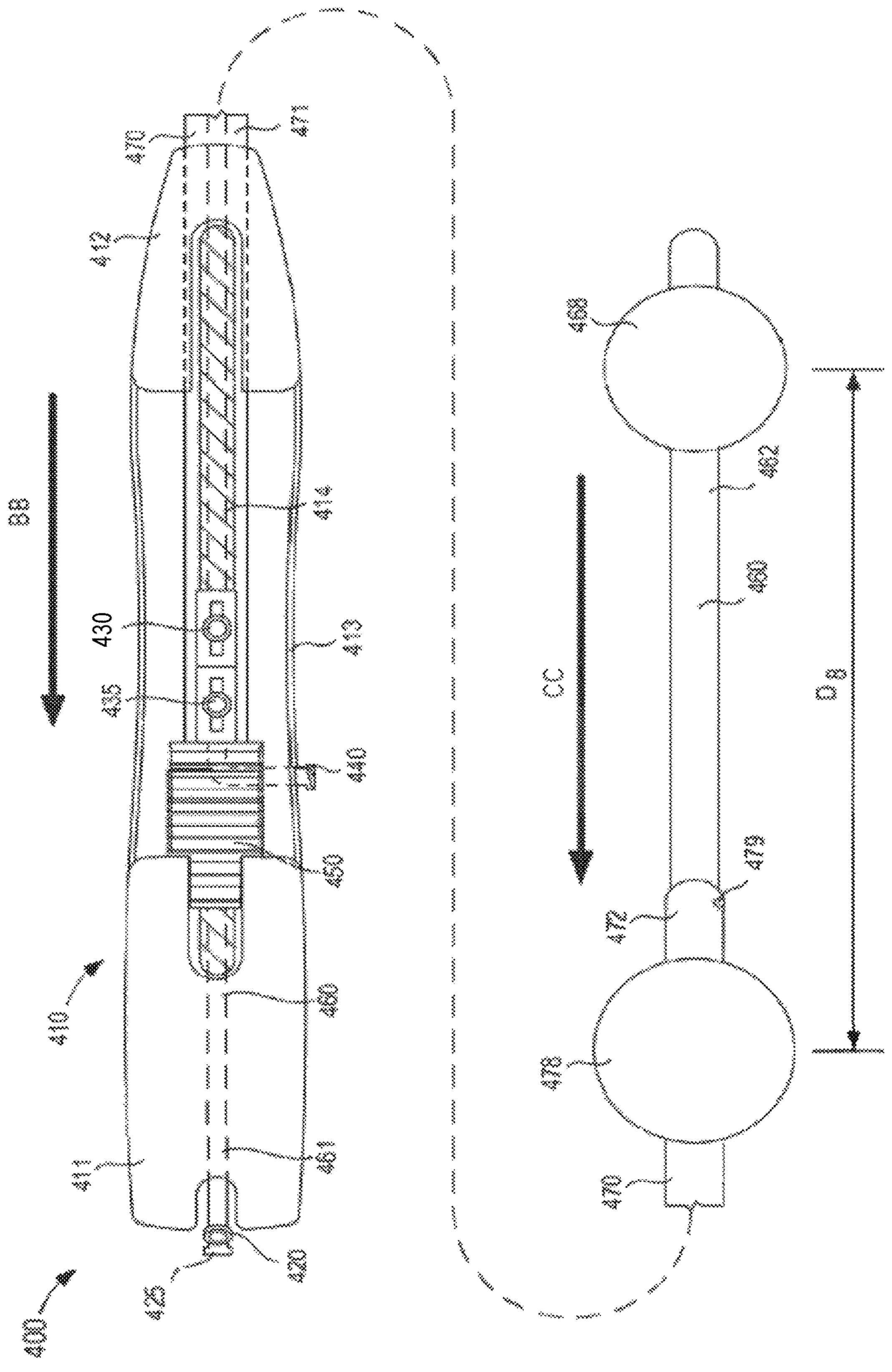
FIG. 29 is a top view of the multi-occlusion catheter insertion device of FIG. 20 in a second configuration.

The actuator 450 of the device 400 is operably coupled to the second set of ports 443. For example, in some embodiments, the actuator 450 is included in and/or coupled to the handle 410 and arranged relative to the second set of ports 443 to be operably coupled thereto. In other embodiments, a handle can be arranged such that at least a portion of an actuator is monolithically formed with at least a portion of a second set of ports. In some embodiments, an actuator is operably coupled to a second set of ports via an intervening structure or the like. For example, in some embodiments, the second set of ports 443 can be coupled to a shuttle or the like, which in turn, is coupled to an actuator. The actuator 450 can be any suitable device, mechanism, assembly, etc. that is movable between the first position relative to the handle 410, associated with the device 400 in the first configuration (FIGS. 20-22), and a second position relative to the handle 410, associated with the device 400 in the second configuration (FIG. 29).

In some embodiments, the actuator 450 can be a mechanism that can be pushed or pulled to slide within the first track 414 defined by the handle 410 between its first position and its second position. In some embodiments, the actuator 450 can be arranged to slide relatively smoothly within the track 414 when moved between its first position and its second position. In other embodiments, the handle 410 and/or the actuator 450 can include a set of ribs, teeth, detents, protrusions, etc. that are sequentially engaged as the actuator 450 is moved between its first position relative to the handle 410 and its second position relative to the handle 410. In this manner, a user can move the actuator 450 a desired distance that can be quantified by the actuator 450 and/or the handle 410 engaging a particular surface (e.g., a particular rib, tooth, detent, protrusion, etc.). In some embodiments, the handle 410 and/or the actuator 450 can be arranged at a predetermined setting that can correspond to a predetermined distance (e.g., 2 cm, 3 cm, etc.) between an end portion of the first catheter 460 and an end portion of the second catheter 470. In some embodiments, the set of ribs, teeth, detents, protrusions, etc. included in the handle 410 and/or the actuator 450 can be associated with pre-defined settings and/or adjustments.

Although not shown in FIGS. 20-29, in some embodiments, a handle 410 can include a visual indicator such as a measuring scale or the like. For example, in some embodiments, the handle 410 can include indicia (e.g., lines, markings, tic marks, etc.) that represents a gradation of a length of travel associated with moving the actuator 450 between its first position relative to the handle 410 and its second position relative to the handle 410. In some embodiments, the markings can represent distances of, for example, a centimeter, half a centimeter, a millimeter, and/or the like. In this manner, a user can view the indicia to determine a desired distance to move that actuator 450 that would otherwise be challenging or indeterminate. In some embodiments, the visual indicator can substantially correspond with the ribs, teeth, detents, protrusions, etc. of the handle 410 and/or actuator 450.

In some embodiments, the actuator 450 can be operably coupled to one or more energy storage device (e.g., a spring or the like) that can facilitate the movement of the actuator 450. For example, the actuator 450 can include a push button that can rearrange or reconfigure at least a portion of the actuator 450 to allow a spring to transition from a compressed configuration towards an uncompressed configuration to move the actuator 450 relative to the handle 410.

With the actuator 450 coupled to or monolithically formed with a portion of the second set of ports 443, the actuator 450 can be operable in moving the second set of ports 443 between a first position relative to the handle 410 (e.g., a distal position) and a second position relative to the handle 410 (e.g., a proximal position). Moreover, with the second catheter 470 physically and fluidically coupled to the second set of ports 443 (as described above), the movement of the actuator 450 and the second set of ports 443 can move the second catheter 470 between a first position relative to the handle 410 and a second position relative to the handle 410, as described in further detail herein.

Figure 23:
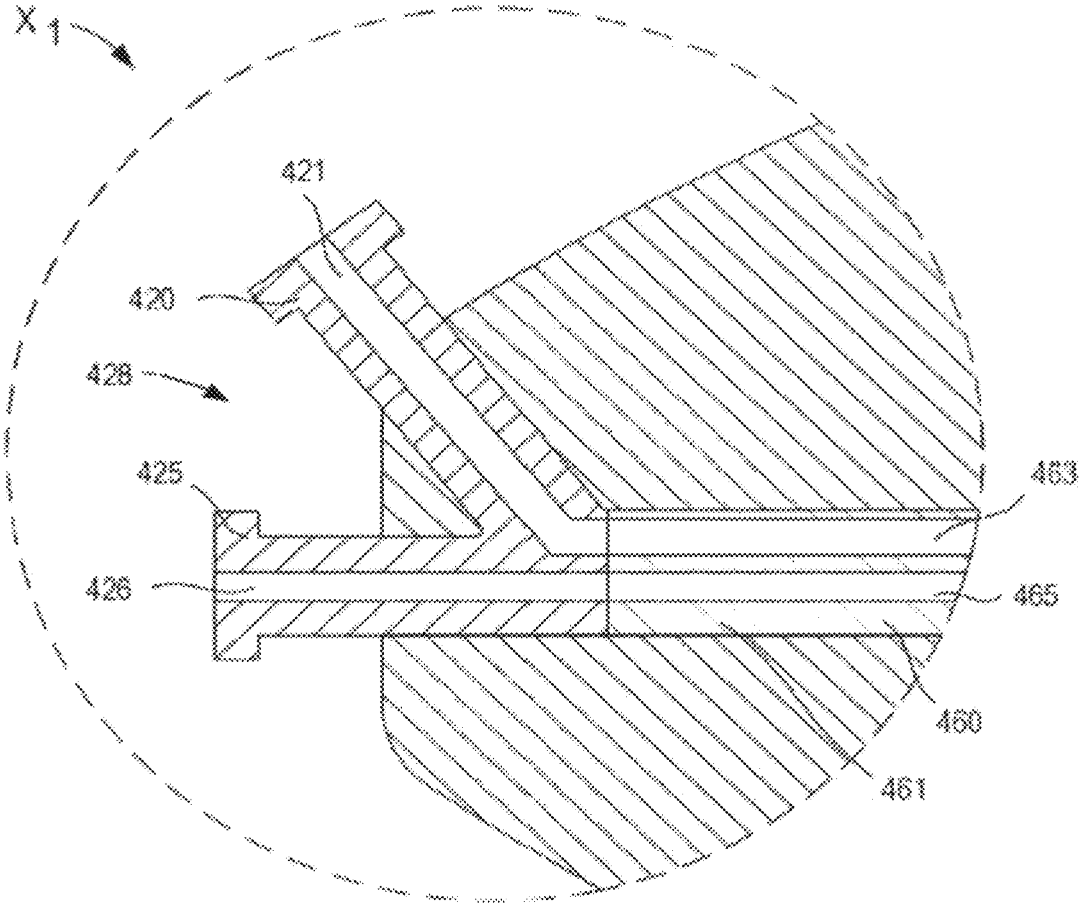
FIG. 23 is an enlarged cross-sectional view of a portion of the handle of FIG. 21, indicated by the region X1 and taken along the line 23-23 in FIG. 22.

The first catheter 460 and the second catheter 470 can be any suitable catheter device. For example, in some embodiments, the first catheter 460 and the second catheter 470 are multi-lumen catheters. The first catheter 460 has a proximal end portion 461 (see, e.g., FIGS. 21, 23 and 29) and a distal end portion 462 (see, e.g., FIGS. 20 and 29), and defines a first lumen 463 and a second lumen 465 (see, e.g., FIGS. 24-28). The proximal end portion 461 of the first catheter 460 is disposed within a portion of the handle 410. More specifically, the proximal end portion 461 of the first catheter 460 can be fixedly disposed within the portion of the handle 410 to place the first catheter 460 in fluid communication with the first set of ports 428. In some embodiments, the first catheter 460 can be physically and fluidically coupled to the first set of ports 428. In other embodiments, a device can include a first catheter that is monolithically formed with a first set of ports. In this manner, the proximal end portion 461 of the first catheter 460 is arranged such that the first lumen 463 of the first catheter 460 is in fluid communication with a lumen 421 defined by the first port 420 and the second lumen 465 of the first catheter 460 is in fluid communication with a lumen 426 of the second port 425, as shown in FIG. 23. Therefore, an external device (e.g., a device that can supply a pressurized fluid, as described above) can be physically and fluidically coupled to the first port 420 to place the external device in fluid communication with the first lumen 463 of the first catheter 460. Similarly, an external device including at least a guidewire (not shown) can be coupled to the second port 425 and can be manipulated to advance the guidewire through the second port 425 and into the second lumen 465, as described in further detail herein.

Referring back to FIG. 20, the distal end portion 462 of the first catheter 460 extends beyond a distal end portion of the handle 410 and includes an occlusion member 468. The occlusion member 468 can be any suitable device or mechanism that is configured to selectively limit, block, obstruct, or otherwise occlude a body lumen (e.g., artery) in which the occlusion member 468 is disposed. For example, in some embodiments, the occlusion member 468 can be an inflatable balloon or the like that can be transitioned between a collapsed (e.g., deflated) configuration and an expanded (e.g., inflated) configuration.

Figure 24:
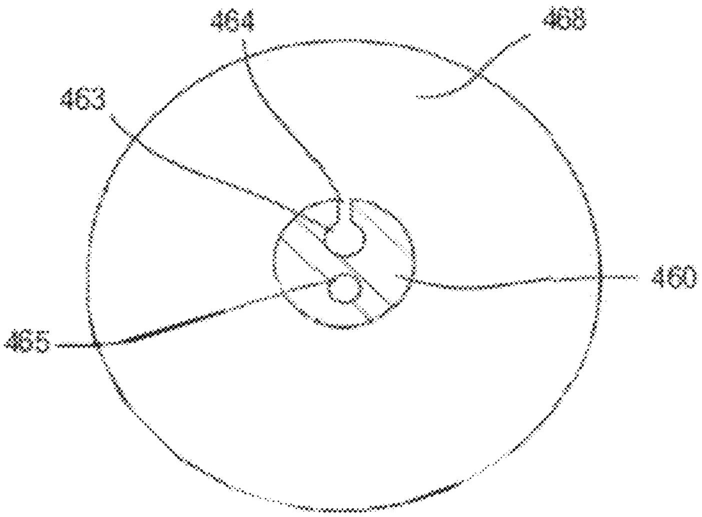
FIG. 24 is a cross-sectional view of a portion of the multi-occlusion catheter insertion device of FIG. 20, taken along the line 24-24.

The arrangement of the first catheter 460 can be such that the first lumen 463 is in fluid communication with the occlusion member 468. For example, as shown in FIG. 24, the distal end portion 462 of the first catheter 460 can define a channel 464 that places the first lumen 463 in fluid communication with the occlusion member 468. Thus, when the first port 420 is fluidically coupled to a device that supplies a pressurized fluid (e.g., air, inert gas, or liquid), the pressurized fluid can be delivered to the occlusion member 468 via the lumen 421 of the first port 420, the first lumen 463 of the first catheter 460, and the channel 464 of the first catheter 460. In this manner, the pressurized fluid can transition the occlusion member 468 between a collapsed configuration (not shown) and an expanded configuration (see e.g., FIG. 20), as described in further detail herein.

The second catheter 470 of the device 400 has a proximal end portion 471 (see, e.g., FIGS. 20-22) and a distal end portion 472 (see, e.g., FIGS. 20 and 29), and defines a first lumen 473, a second lumen 474, a third lumen 476 and an opening 479 (also referred to herein as "infusion aperture") (as shown, for example, in FIGS. 25-28). The second catheter 470 is movably disposed about a portion of the first catheter 460 (see, e.g., FIGS. 21-23). More specifically, the second catheter 470 can be arranged such that the first catheter 460 is movably disposed within the first lumen 473 defined by the second catheter 470, as shown, for example, in FIGS. 26-28.

Figure 25:
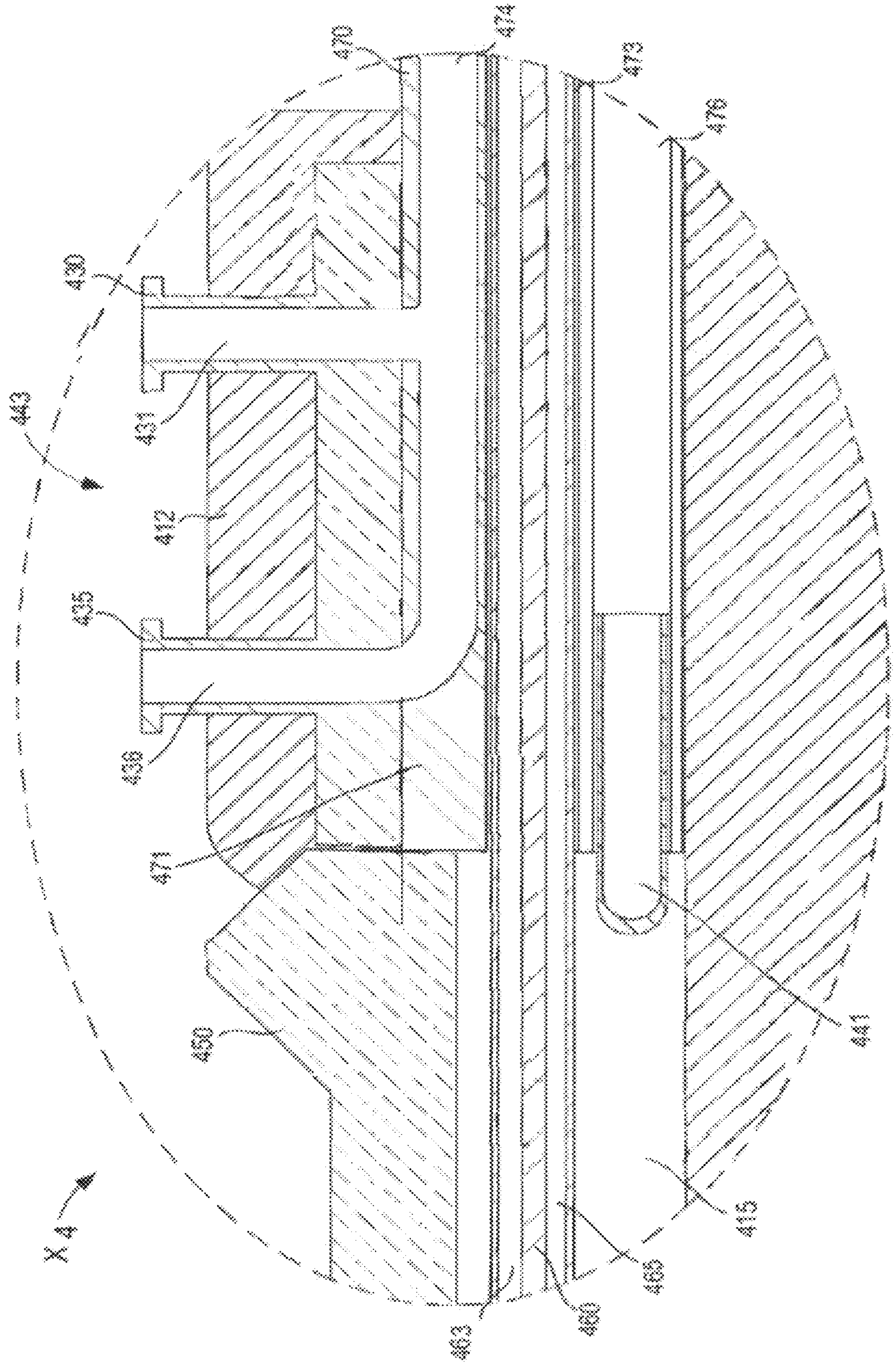
FIG. 25 is an enlarged cross-sectional view of a portion of the handle of FIG. 21, indicated by the region X2 and taken along the line 25-25 in FIG. 22.
Figure 26:
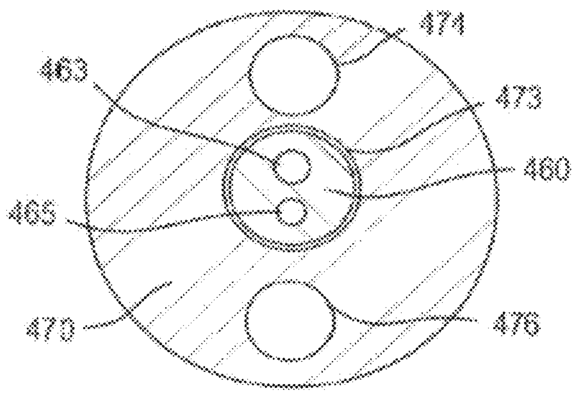
FIG. 26 is a cross-sectional view of a portion of the multi-occlusion catheter insertion device of FIG. 20, taken along the line 26-26.

The proximal end portion 471 of the second catheter 470 is movably disposed within the handle 410 to place the second catheter 470 in fluid communication with the second set of ports 443. In some embodiments, the second catheter 470 can be physically and fluidically coupled to the third port 430 and the fourth port 435, and/or the fifth port 440. In other embodiments, a catheter insertion device can include a second catheter that can be movably disposed within a handle and can be operably coupled to one or more ports via an intervening structure such as, for example, flexible tubing or the like. In yet other embodiments, a catheter insertion device can include a second catheter that is monolithically formed with a third port, a fourth port, and/or a fifth port. In this manner, the second catheter 470 is arranged such that the first lumen 473 of the second catheter 470 movably receives the first catheter 460, the second lumen 474 of the second catheter 470 is in fluid communication with a lumen 431 defined by the third port 430 and a lumen 436 defined by the fourth port 435, and the third lumen 476 of the second catheter 470 is in fluid communication with a lumen 441 defined by the fifth port 440, as shown in FIG. 25.

Referring back to FIG. 20, the distal end portion 472 of the first catheter 470 extends beyond a distal end portion of the handle 410 such that an occlusion member 478 of the second catheter 470 is disposed in a proximal position relative to the occlusion member 468 of the first catheter 478. Expanding further, the first catheter 460 extends within the proximal end portion 471 and the distal end portion 472 when disposed in the first lumen 473. Thus, the occlusion member 468 of the first catheter 460 can be disposed in a distal position relative to the occlusion member 478 of the second catheter 470. The occlusion member 478 can be any suitable device or mechanism that is configured to selectively limit, block, obstruct, or otherwise occlude a body lumen (e.g., artery) in which the occlusion member 478 is disposed. For example, in some embodiments, the occlusion member 478 can be substantially similar to the occlusion member 468 of the first catheter 468.

Figure 27:
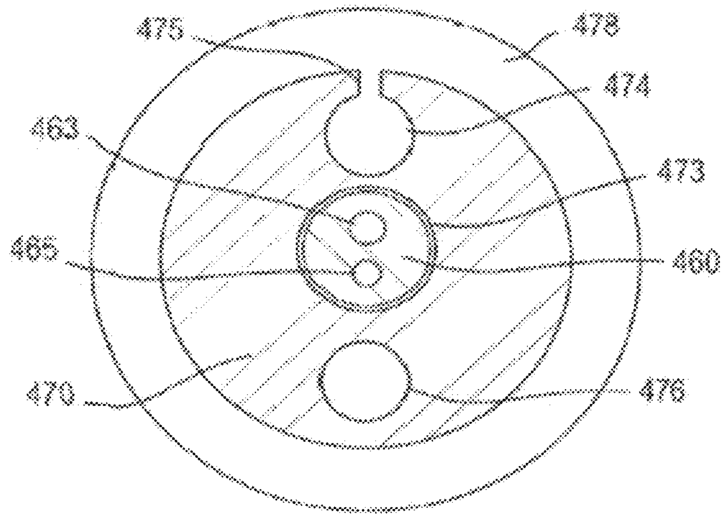
FIG. 27 is a cross-sectional view of a portion of the multi-occlusion catheter insertion device of FIG. 20, taken along the line 27-27.
Figure 28:
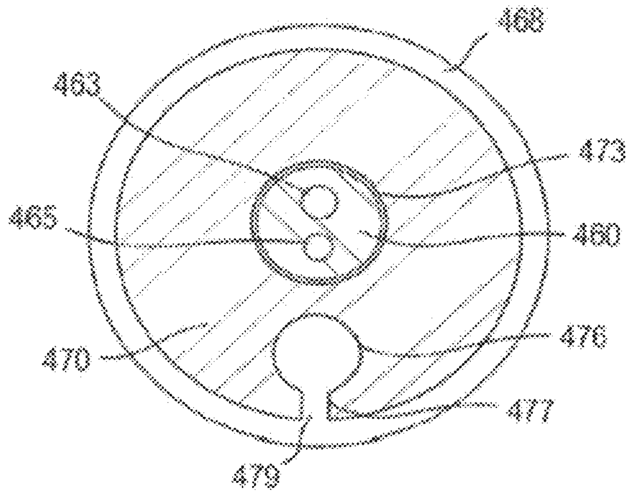
FIG. 28 is a cross-sectional view of a portion of the multi-occlusion catheter insertion device of FIG. 20, taken along the line 28-28.

The arrangement of the second catheter 470 can be such that the second lumen 474 is in fluid communication with the occlusion member 468. For example, as shown in FIG. 27, the distal end portion 472 of the second catheter 470 defines a channel 475 that places the second lumen 474 in fluid communication with the occlusion member 478. Thus, when the third port 430 (and/or the fourth port 435) is fluidically coupled to a device that supplies a pressurized fluid, the pressurized fluid can be delivered to the occlusion member 478 via the lumen 431 of the third port 430 (and/or the lumen 436 of the fourth port 435), the second lumen 474 of the second catheter 470, and the channel 475 of the second catheter 470. In this manner, the pressurized fluid can transition the occlusion member 478 between a collapsed configuration (not shown) and an expanded configuration (as shown in FIGS. 20 and 29). In a similar manner, the arrangement of the second catheter 470 can be such that the third lumen 476 is in fluid communication with the opening 479 (see, e.g., FIG. 28). For example, the distal end portion 472 of the second catheter 470 defines a channel 477 that places the third lumen 476 in fluid communication with the opening 479, as shown in FIG. 28. Thus, when the fifth port 440 is fluidically coupled to an external device that supplies irrigation or to a device that supplies a therapeutic agent, the irrigation fluid or therapeutic agent can be delivered to an isolated segment of a bodily lumen via the lumen 441 defined by the fifth port 440 and the third lumen 476, the channel 477, and the opening 479 defined by the second catheter 470.

The device 400 can be moved from the first configuration to the second configuration by moving the actuator 450 from its first position (e.g., a distal position) relative to the handle 410 to its second position (e.g., a proximal position) relative to the handle 410, as indicated by the arrow BB in FIG. 29. Expanding further, with the second catheter 470 movably disposed about the first catheter 460 and with the proximal end portion 471 of the second catheter 470 operably coupled to the actuator 450, the movement of the actuator 450 from its first position to its second position moves the second catheter 470 relative to the first catheter 460, as indicated by the arrow CC in FIG. 29. For example, when the device 400 is in the first configuration, a first distance D7 (FIG. 20) can be defined between the occlusion member 468 of the first catheter 460 and the occlusion member 478 of the second catheter 470. With the first catheter 460 fixedly disposed within the handle 410, the movement of the second catheter 470 in the CC direction (e.g., the proximal direction) increases the distance between the occlusion member 468 of the first catheter 460 and the occlusion member 478 of the second catheter 470 to a second distance D8, as shown in FIG. 29. Thus, a segment or volume having a desired length can be defined between the occlusion member 468 of the first catheter 460 and the occlusion member 478 of the second catheter 470.

Figure 30:
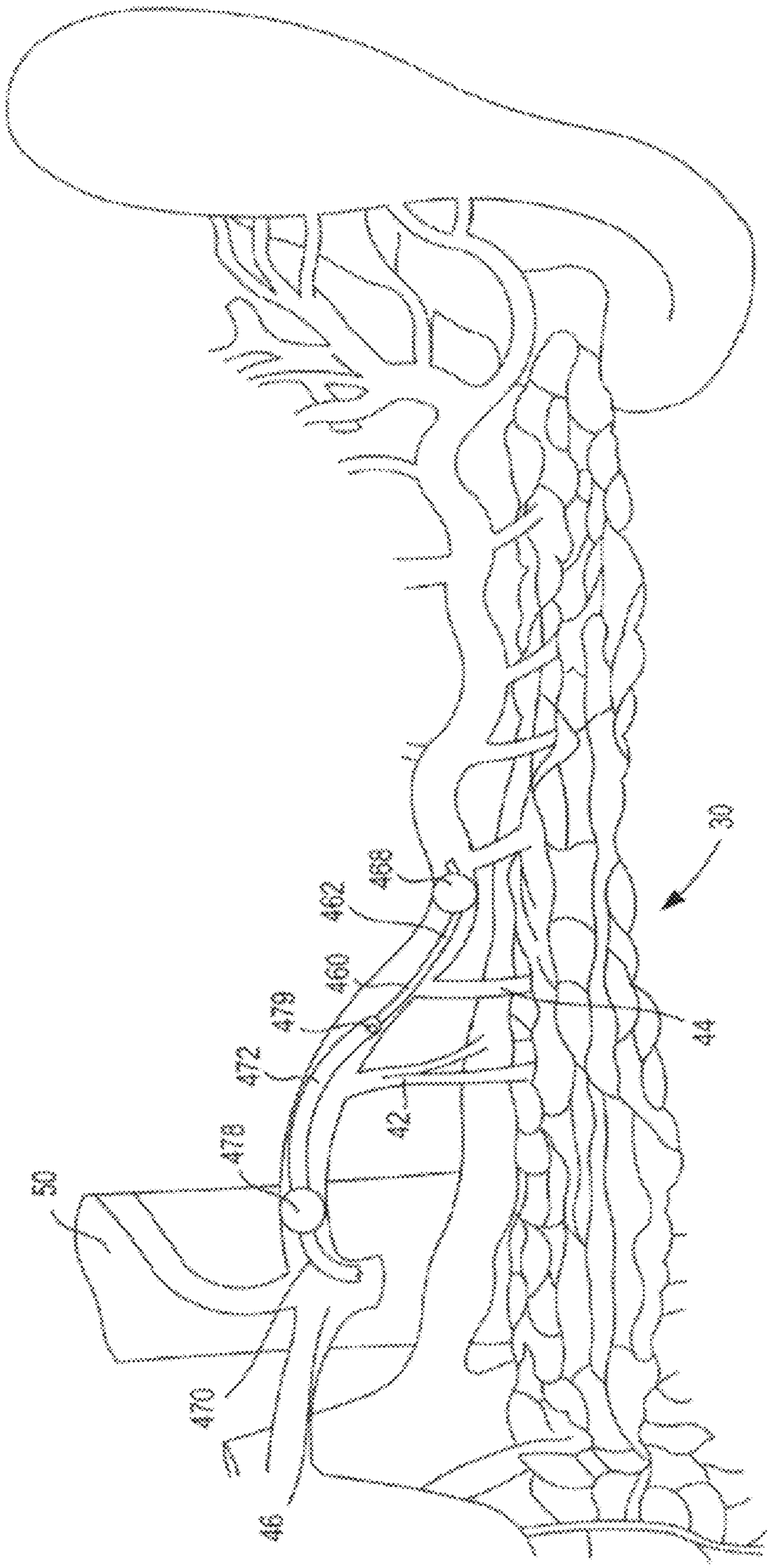
FIG. 30 is an illustration of a portion of the multi-occlusion catheter insertion device of FIG. 20 in use within a portion of a body.

In use, a guidewire can be inserted into the lumen 426 of the second port 425 and through the second lumen 465 defined by the first catheter 460. In this manner, the guidewire can be advanced through a bodily lumen and the device 400 can be manipulated to advance the first catheter 460 and the second catheter 470 along the guidewire. Thus, the distal end portion 462 of the first catheter 460 and the distal end portion 472 of the second catheter 470 can be placed at a target location within the bodily lumen such as, for example, the haptic or splenic artery of the pancreas, as shown in FIG. 30. At the target location, the actuator 450 can be moved between its first position and its second position relative to the handle 410 (e.g., the BB direction in FIG. 29) to define a desired distance (e.g., the distance D8 in FIG. 29) between the occlusion member 468 of the first catheter 460 and the occlusion member 478 of the second catheter 470. With the desired distance defined between the occlusion members 468 and 478, and with an inflation source coupled to the first port 420 and the same or a different inflation source coupled to the third port 430 (and/or the fourth port 435), the occlusion member 468 of the first catheter 460 and the occlusion member 478 of the second catheter 470, respectively, can be transitioned from a collapsed or deflated configuration to an expanded or inflated configuration to substantially isolate a segment of the bodily lumen disposed therebetween (e.g., the pancreatic segment or portion of the splenic artery 40 associated with, for example, the dorsal pancreatic artery 42 and/or the pancreatic magnum artery 44), as shown in FIG. 30. FIG. 30 is an illustration of the catheter device 400 disposed in situ within the splenic branch of the celiac artery. As shown in FIG. 30, the occlusion elements 468 and 478 define or isolate an area of interest in between the occlusion elements 468 and 478. Specifically, in this example, the region or area of interest with blood supply to the pancreas is isolated via the occlusion elements 468 and 478, spaced according to the location of the dorsal pancreatic artery 42 and the pancreatic magnum artery 44.

With the occlusion members 468 and 478 substantially occluding the body lumen, a biological/therapeutic agent can be delivered to the substantially isolated segment via the fifth port 440, the third lumen 476, and the opening 479 (i.e., the infusion aperture), into the area substantially isolated between the occlusion elements 468 and 478. In some instances, the substantially isolated segment can be irrigated by coupling an irrigation source to the fifth port 440. Thus, the irrigation can be delivered to the substantially isolated segment via the lumen 441 of the fifth port 440 and the third lumen 476, the channel 477, and the opening 479 of the second catheter 470. In some instances, such irrigation can be delivered prior to the delivery of the biological/therapeutic agent, after the delivery of the biological/therapeutic agent, or substantially concurrently with the biological/therapeutic agent.

Figure 31:
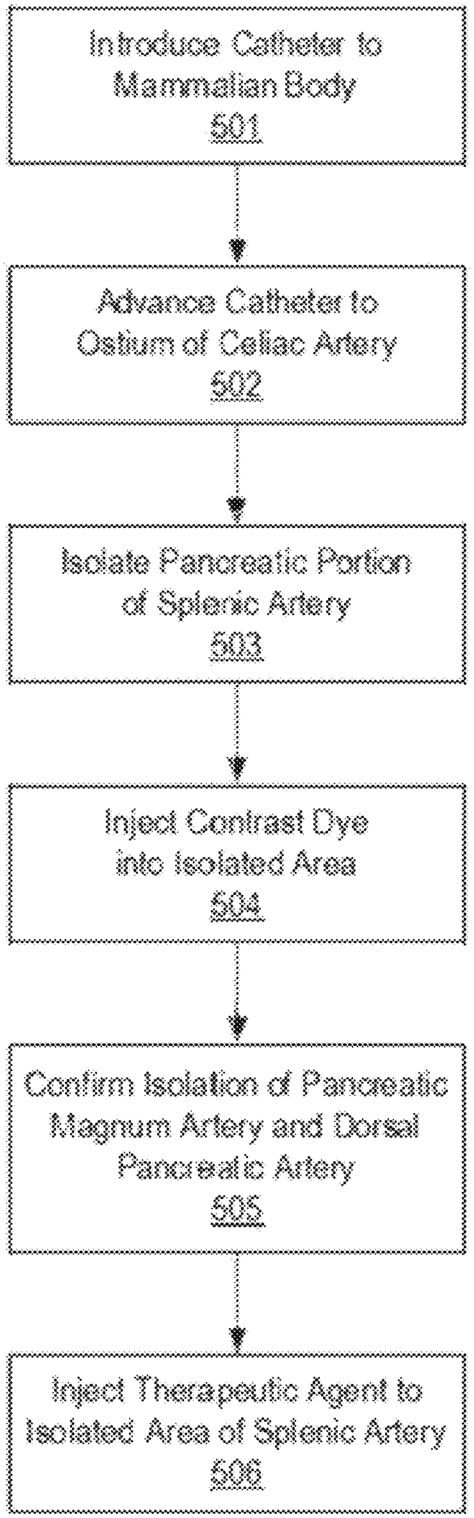
FIG. 31 is a flowchart illustrating a method for treating the pancreas, according to an embodiment.

FIG. 31 is a flowchart illustrating a method of accessing and treating a pancreas. The method can be used, for example, to occlude a portion of the splenic branch of the celiac artery supplying the pancreatic tail. The method includes introducing a catheter (e.g., the catheter device 100, 200, 300, and/or 400) into a mammalian body over a guidewire (211, 311) into a celiac artery, at 501. The catheter device can include an inner catheter (e.g., the first catheter 160, 260, 360, and/or 460) slidably coupled to an outer catheter (e.g., the second catheter 170, 270, 370, and/or 470). In some embodiments, a guide catheter can be exchanged over the guidewire into the celiac artery for support and introduction of the catheter device. After the guidewire is in place, the catheter device can be positioned over the guidewire, at 502, and positioned to allow placement of a distal occlusion element (e.g., the distal occlusion element 168,268,368, and/or 468) of the inner catheter at a distal edge of the pancreatic portion of the splenic artery (see, e.g., FIG. 30). The distal occlusion element and a proximal occlusion element (e.g., the proximal occlusion element 178, 278, 378, and/or 478) of the outer catheter are positioned to isolate a target portion of the pancreatic artery and moved to an expanded configuration, at 503. After the occlusion elements are deployed, contrast dye is injected through an injection port of the outer catheter and the isolated area of the splenic artery is visualized to identify the pancreatic branches, at 504. Visualization enables the clinician to confirm isolation of the pancreatic magnum artery and dorsal pancreatic artery or any other large artery supplying the pancreatic body or tail in the area, at 505. If desired, the catheter device can be moved back, and the procedure repeated until the clinician can confirm that the catheter is correctly positioned. Some example isolation regions include: (a) the pancreatic magnum artery 44 (and its branches), (b) the dorsal pancreatic artery 42 if the origin is within the splenic artery 40, and (c) both pancreatic magnum artery 44 and dorsal pancreatic artery 42 arteries are isolated in one contiguous area (if other extra-pancreatic arteries do not arise between the origin of the two within the splenic artery 40).

After the first takeoff of the pancreatic magnum artery 44 is identified (or the dorsal pancreatic artery), the placement of the outer catheter of the catheter device can allow the edge of the distal occlusion element to be placed beyond this artery. At this point, the inner catheter can be secured in place, and the outer catheter can be moved relative to the inner catheter to allow the maximum perfusion area to the body and tail of the pancreas. Frequent injection of contrast through the infusion port can be made to ensure no extra-pancreatic vessels are included in the isolated area.

After the desired area is isolated and the occlusion elements are positioned at a desired location, the therapeutic cells/biologics/agent is introduced to the isolated area of the splenic artery through the infusion port of the outer catheter, at 506. The infusion port design can allow rapid and atraumatic infusion of cells/biologics/agent into the isolated area. This allows the clinician to adjust rate of infusion of therapeutic cells/biologics/agents into the isolated area based on specific pharmacodynamics and or engraftment efficiency requirements. The infusion of the therapeutic material can be followed by heparinized blood to exclude any residual cells left behind in the dead space of the catheter device. During isolation of the artery described above, perfusion to the end organ to the artery spleen can be disrupted, but the redundancy in the arterial perfusion system to the spleen, and limited time during which the arterial supply is interrupted, should prevent any long-term sequela, or abnormal condition of the splenic cells. If needed and/or desired, the guidewire port can be used to perform perfusion of the splenic artery beyond the isolated area. For example, the guidewire can be removed from its port after the catheter device is in place, and the guidewire port can be connected to a source of arterial blood with suitable pressure (i.e. the side port of an arterial sheath or guide sheath). At the end of the infusion, both occlusion elements are moved to a collapsed configuration and the catheter device is removed from the body over the guidewire as one unit, followed by the guidewire and the guide catheter.

In a variation of the method described above using balloons as the occlusion elements, the same catheter can be used to isolate arterial branches supplying the head of the pancreas via the hepatic artery or superior mesenteric artery. One such clinical possibility is treatment of pancreatic cancer with the tumor located in the head of the pancreas. After placement of the catheter device in the respective artery, the infusion of contrast through the infusion port can identify the branches most proximate to the tumor, and then after occluding the distal and proximal portion of the artery around the branch(es), the chemotherapeutic agent can be delivered selectively to the area of interest in the pancreas.

In some embodiments, a method can include introducing a catheter device into a splenic artery. The catheter device can include an inner catheter, a first expandable occlusion element coupled to the inner catheter, an outer catheter defining a first lumen configured to introduce a therapeutic biologic/agent to one or more target pancreatic vessels, a second lumen configured to slidably receive at least a portion of the inner catheter, and a second expandable occlusion element coupled to the outer catheter and disposed proximally to the first occlusion element. The catheter is advanced to a target pancreatic portion of the splenic artery. A region of the target pancreatic portion of the splenic artery is selectively isolated, and the therapeutic biologic/agent is injected into the isolated region. In some embodiments, the therapeutic biologic/agent includes stem cells. In some embodiments, the method further includes advancing at least a portion of the catheter device to an ostium of a celiac artery, its hepatic branch, or if necessary, the superior mesenteric artery (based on individual anatomy). In some embodiments, a contrast dye is injected into the isolated region and isolation of a pancreatic magnum artery and/or a dorsal pancreatic artery can be confirmed. In some embodiments, a guidewire can be disposed through the infusion lumen to focally perforate the vascular lumen in the isolated area to increase exogenous cell penetration into the pancreatic tissue. In some embodiments, the therapeutic biologic can be introduced into the isolated segment or region to enhance cellular transmigration across the endothelial cells prior to introduction of the therapeutic biologic.

In some embodiments, a method can include introducing a catheter device into a bile duct. In use, the catheter device 200 can be placed at a desired location within the bile duct and used to infuse a therapeutic agents into the bile duct which will diffuse through the bile duct into the pancreas. A length of the first catheter 260 and the second catheter 270 can be adjusted such that a selected portion of the bile duct is isolated between the first occlusion element 268 and the second occlusion element 278. A therapeutic agent can be injected through the catheter device 200 and into the isolated region of the bile duct.

The infusion pressure in the isolated blood vessel region can be measured with pressure monitoring through the infusion lumen of the catheter (with a manometer (not shown) in line with infusion port 279). The pressure in the third lumen 276 can be based on the size of the agents being delivered, on the flow rate, the viscosity of the solution, and/or flow resistance of the third lumen 276 of second catheter 270. The flow resistance of the catheter device 200 can in turn be determined based on, for example, the inner coating material, the size and the length of the third lumen 276, the size of the third port 240, and/or the size of the distal infusion aperture 279. The catheter device 200 can allow for rapid infusion of agents (e.g., up to 2 milliliter per second (ml/sec)). In some applications, the rapid infusion can enhance uptake and eventual engraftment.

Any catheter device described herein and/or any combination of the catheter devices described herein can allow the above goals to be achieved. For example, a catheter device can include two catheters slidably coupled where an inner catheter defines a guidewire housing port and a distal occlusion element, and an outer catheter forms an infusion port and a proximal occlusion element, along with an inner lumen allowing the insertion of the inner catheter. The two catheters can be assembled outside the body with a distance between the two occlusion elements set to a desired length. For example, in some embodiments, the minimum distance between the two occlusion elements can be 3 cm, and the length can be adjusted up to a distance between the two occlusion elements of 25 cm as needed.

The devices described herein can also be provided in a kit. In some embodiments, a kit for use in the delivery of a biological agent to an area proximal to the pancreas can include, for example, one or more catheter devices (e.g., the catheter devices 100, 200, 300, and/or 400) as described herein and one or more biologic/therapeutic agent for delivery to the pancreas. The catheter devices can include, for example, a proximal end portion, a distal end portion and one or more expandable devices, such as a balloon or a filter, associated therewith. In some embodiments, the catheter device can include a first catheter configured to be slidably received within a lumen of a second catheter, a first occlusion element coupled to the first catheter and a second occlusion element coupled to the second catheter. In such an embodiment, a distance between the first and second occlusion elements can be varied or adjusted. The occlusion elements can be expandable to engage a wall of a blood vessel thereby substantially isolating an interior region of the vessel between the first and second occlusion elements. Moreover, the first and second catheters can be configured such that at least one of the first and second catheters has a lumen configured to deliver a biological/therapeutic agent to the isolated interior region via an infusion port. The infusion port can allow for rapid and atraumatic delivery of cells/biologics into the isolated area. In some embodiments, a pressure regulator can be provided that is configured to regulate the fluid pressure of the agent or the materials used to dilate the occlusion element(s) (e.g., in a balloon embodiment).

In some embodiments, a kit can further include one or more biologic/therapeutic agents for delivery to the pancreas, a stylet(s); one or more catheters adapted and configured for accessing the pancreatic vessels; a dilator; a guidewire; a guide catheter; capsules for direct connection of biological materials/cells to the infusion port of the delivery catheter; a manometer to monitor the pressure in the isolated area; and/or a pump to regulate the infusion rate of cells/biologics.

In some embodiments, any of the components of a kit can be packaged together and collectively sold as a catheter device or can be packaged independently or in subgroups and sold together or separately. For example, in some embodiments, the handle 410 can be packaged independently from the first catheter 460 and the second catheter 470. Moreover, the first catheter 460 and the second catheter 470 can be packaged independent from one another or packaged together. As such, the handle 410 can be sold independent of the first catheter 460 and the second catheter 470. The first catheter 460 and the second catheter 470 can be sold independent of one another or together. Thus, in some embodiments, the handle 410 can be packaged independent of the first catheter 460 and the second catheter 470 and, prior to use, can be coupled to the first catheter 460 and the second catheter 470 such that the first set of ports 428 are in fluid communication with the corresponding lumen of the first catheter 460 and the second set of ports 443 are in fluid communication with the corresponding lumen of the second catheter 470. In some embodiments, the handle 410 can be, for example, reusable, while the first catheter 460 and the second catheter 470 are disposable. In other embodiments, the handle 410 can be coupled to the first catheter 460 and the second catheter 470 during, for example, a manufacturing process and packaged together to be sold as a complete catheter device.

In some embodiments, placement of the occlusion elements (e.g., the distal occlusion elements 168, 268, 368, and/or 468 and the proximal occlusion elements 178, 278, 378, and/or 478) and the lengths of each region therebetween can be varied based on the needs of the individual application. The catheter devices 100, 200, 300 and/or 400 can retain sufficient trackability to allow advancement into the target region of the patient. In some embodiments, the catheter material can be flexible enough to traverse local anatomy yet have enough tensile strength to be able to be placed in position in place over a guidewire (e.g., the guidewire 280 and/or 380). Furthermore, for the first catheters 160,260,360, and 460 and the second catheters 170, 270, 370, and 470, respectively, to be slidable relative to each other in situ, various radial and tensile strengths can be incorporated in each.

The first catheters 160, 260, 360, and/or 460 (i.e., the inner catheters) and the second catheters 170, 270, 370, and/or 470 (i.e., the outer catheters) can be fabricated of any material suitable for catheters, such as linear low density or high density polyethylene, nylon, polyurethane, polypropylene, silicone rubber, or other non-thrombogenic materials. In some embodiments, an outer catheter can be formed from a linear low-density polyethylene, while an inner catheter can be formed from a nylon. In some embodiments, the outer catheters described herein can be fabricated to include a structure for reinforcement (not shown), such as a metal braid or the like located between an inner and outer layer. The reinforcement structure can extend along any desired length of such outer catheters. In some embodiments, a reinforcement structure can extend along the entire length of an outer catheter.

In some embodiments, regions of a first catheter (i.e., an inner catheter) such as those described herein can also be fabricated in any manner that allows the relative stiffness of each region to vary. In some embodiments, an outer layer in each region of an outer catheter and/or an inner catheter can include a material with a different durometer measurement of hardness. For example, the material used in an intermediate region can be relatively harder than that used in a distal region, and the material used in a proximal region can be relatively harder than that used in the intermediate region. Other manners of varying the stiffness of an inner catheter and/or an outer catheter (i.e., a first catheter and a second catheter, respectively, such as those described herein) can include varying the length of a reinforcement structure, varying the degree of reinforcement provided by the reinforcement structure along the length of the inner catheter and/or the outer catheter, changing a cross-sectional size and/or shape of the inner catheter and/or the outer catheter, introducing and/or forming one or more discontinuities along a length of the inner catheter and/or the outer catheter (e.g., one or more ribs, notches, grooves, protrusions, etc.), and/or any other suitable means for varying stiffness.

In some embodiments, the catheter devices described herein can include one or more sensors that can provide relative information such as, for example, position of the occlusion members, movement of the actuator, flow rate of the biological agent, and/or any other suitable information. For example, in some embodiments, a sensor can be operably coupled to the actuator 450 of the device 400 and can be configured to provide information associated with a distance that the actuator 450 has been moved. In such embodiments, a user and/or an electronic device can determine a distance between the occlusion member 468 of the first catheter 460 and the occlusion member 478 of the second catheter 470 based on the information from the sensor. In some embodiments, a sensor can be disposed within the third lumen 476 of the second catheter 470 that can be configured to determine a flow rate of irrigation and/or a biological/therapeutic agent therethrough.

In some embodiments, radiopaque markers of gold or tantalum, for example, can also be provided on or in an inner catheter positioned, within or on an occlusion element(s) (e.g., the occlusion elements 168, 178, 268, 278, 368, 378, 468, and/or 478), and/or on an outer catheter to aid in visualization and to assist in monitoring the position of at least a portion of a catheter device (e.g., the catheter devices 100, 200, 300, and/or 400) on an imaging device (e.g., a fluoroscope, an X-Ray, a Magnetic Resonance Imaging (MRI) scan, a computerized tomography (CT) scan, and/or the like) during a procedure. In some embodiments, an inner catheter can optionally be coated with a lubricous material, such as silicone, acrylamide, or a hydrophilic polyurethane coating, to ease retraction. Similarly, the outer catheter and the occlusion elements can be coated with the lubricous material to ease advancement through a guiding catheter and/or a tortuous vessel.

In some embodiments, an outer diameter of an outer catheter (e.g., the second catheters 100, 200, 300 and/or 400) and non-deployed occlusion elements (e.g., the occlusion elements 168 and 178,268 and 278,368 and 378, and/or 468 and 478) can be, for example, between about 6 French and about 8 French and thus, can be used with, for example, a 7-9 French guiding catheter (if need be).

In some embodiments, after a guidewire (e.g., the guidewire 280 and/or 380) is removed, a corresponding lumen (e.g., the second lumen 165, 265, 365, and/or 465 of the first catheter 160,260, 360, and/or 460, respectively) can be used to establish arterial blood flow distal to the occlusion end (e.g., the distal end portion) of a catheter device or infusion of other therapeutic agents if desired.

In some embodiments, any suitable configuration of the catheter devices can be used to achieve the objectives described herein including, for example, employing one or more catheter devices 100, 200, 300, and/or 400, employing a contiguous inflation/occluding section having differing stiffness along its length to achieve the two occluding elements, and/or the like.

In some embodiments, to allow endovascular isolation of the pancreatic portion of the splenic artery 40 (see e.g., FIG. 1) as a mechanism to achieve substantially exclusive delivery of a therapeutic agent/cells to the pancreatic parenchyma, a catheter device such as those described herein can include anatomical and mechanical features such as, for example, isolation of the two ends of the pancreatic portion of the artery using two occlusion elements; adjustment of the diameter of the occlusion elements to meet the specific anatomical needs; adjustment of the distance between the two occlusion elements (based on individual variation to selectively isolate for instance the portion of the splenic artery 40 to the pancreas 30 on one hand and maximize the perfusion area on the other hand); an infusion port where injection of contrast can be used to visualize the area of the artery isolated; an infusion port, shaft, and/or aperture design to allow atraumatic and rapid delivery of cells/therapeutic agents; and/or recovery of the occlusion element along with the catheter at the end of the procedure, prior to which flushes through the infusion port can assure clearance of the cells from the isolated space.

In some instances, any portion of the catheter devices 100,200, 300, and/or 400 can be rotated to allow for a more targeted delivery of the biological/therapeutic agent to a selected tissue. For example, while the infusion apertures 279, 379 and 479 are shown as being disposed at a specific position relative to the pancreas 30, in some instances, the catheter device 100, 200, 300, and/or 400 can be rotated to rotate the second catheter 470 relative to the pancreas 30. Thus, the infusion aperture 279, 379, and/or 479 is rotated about a longitudinal axis (not shown) defined by the second catheter 270, 370, and/or 470. As such, the infusion aperture 279, 379, and/or 479 can be positioned adjacent to a target tissue for a more accurate delivery of the biological agent than would otherwise be possible. In some embodiments, any portion of the catheter device 200, 300, and/or 400 can include indicia and/or markings that can be associated with the relative position of the infusion aperture 279, 379, and/or 479. In this manner, a user can visualize the radial position of, for example, an actuator (e.g., the actuator 450) to determine the radial position of the infusion aperture 279, 379, and/or 479.

Any catheter device described herein and/or any combination of the catheter devices described herein can allow the above goals to be achieved. For example, a catheter device can include two catheters slidably coupled where an inner catheter defines a guidewire housing port and a distal occlusion element, and an outer catheter forms an infusion port and a proximal occlusion element, along with an inner lumen allowing the insertion of the inner catheter. The two catheters can be assembled outside the body with a distance between the two occlusion elements set to a desired length. For example, in some embodiments, the minimum distance between the two occlusion elements can be 3 cm, and the length can be adjusted up to a distance between the two occlusion elements of 25 cm as needed.

In some embodiments, a catheter device such as those described herein, which is suitable for accessing the pancreas 30 (see e.g., FIG. 1) can include features and/or functions, such as, for example, selective isolation of the targeted portion of the pancreatic portion of the splenic artery 40 for targeted delivery of the therapeutic agent to the pancreas 30; an adjustable distance between the two ends of the perfusion/infusion area (e.g., an isolated region) to accommodate individual anatomy to allow isolation of the largest portion of the splenic artery 40 with branches only supplying the pancreatic tail 32 and body 34 (see e.g., FIG. 1) and if clinically indicated, the same catheter can be used to isolate portions of the hepatic artery 54 and/or superior mesenteric artery 52 supplying the head of the pancreas 38; an infusion port allowing first, injection of contrast into the isolated segment to allow direct visualization of the origin of the branches of the splenic artery 40 supplying the pancreatic tissue, and second, introduction of therapeutic drugs/cells, the dimensions and design of the infusion port and catheter shaft allowing rapid and atraumatic delivery of cells; adjustable diameter of the proximal and/or distal occluders to allow both intravariable and intervariable sizes of the splenic artery 40; and/or a self-contained assembly unit with easy retrieval after completion of the procedure.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above. For example, the size and specific shape of the various components can be different from the embodiments shown, while still providing the functions as described herein. Furthermore, each feature disclosed herein may be replaced by alternative features serving the same, equivalent or similar purpose, unless expressly stated otherwise. Thus, unless expressly stated otherwise, each feature disclosed is one example only of a generic series of equivalent or similar features.

For example, although the outer catheters 170, 270, 370, and/or 470 of the catheter devices 100, 200, 300, and/or 400 include an infusion lumen (i.e., a third lumen) and infusion port and/or aperture to deliver a cell/biologic/therapeutic material to a desired blood vessel, in other embodiments, the inner catheter 160, 260, 360, and/or 460, respectively, can include the infusion lumen. Similarly, although the guidewire lumen (i.e., a second lumen) is described as being defined by the inner catheter 160, 260, 360, and/or 460, a guidewire lumen can be alternatively, or in addition to, included in and/or defined by the outer catheter 170, 270, 370, and/or 470. Thus, any of the lumens of the catheter devices 100, 200, 300, and/or 400 can be defined by either the first catheter 160, 260, 360, and/or 460 (i.e., an inner catheter) or the second catheter 170, 270, 370, and/or 470 (i.e., an outer catheter). In another example, although shown coupled to the second catheter 270 and/or 370, the sealing element 285 and/or 385 can alternatively be coupled to the first catheter 260 and/or 360.

Although the catheter devices 100, 200, 300, and/or 400 have been shown and described as having either two balloon occlusion elements or two filter elements, in alternative embodiments, a catheter device can include a combination of occlusion elements. For example, a catheter device such as those described herein can include one or more balloon occlusion elements (e.g., the balloon elements 268 and/or 278) and one or more filter element occlusion elements (e.g., the filter elements 368 and/or 378).

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above. For example, the size and specific shape of the various components can be different from the embodiments shown, while still providing the functions as described herein. Furthermore, each feature disclosed herein may be replaced by alternative features serving the same, equivalent or similar purpose, unless expressly stated otherwise. Thus, unless expressly stated otherwise, each feature disclosed is one example only of a generic series of equivalent or similar features.

In some cases, a multiple occlusion catheter device may be positioned within a first vessel that further includes another vessel that branches off of the first vessel. The catheter device may include a plurality of lumens that may be used to isolate one or more sections of these vessels and further deliver therapeutic agents to the isolated area. In some embodiments, the catheter device may include features that can provide fluid flow (including blood flow) around the isolated area. Examples of such catheter devices are described below in conjunction with FIGS. 32-48.

Figure 32:
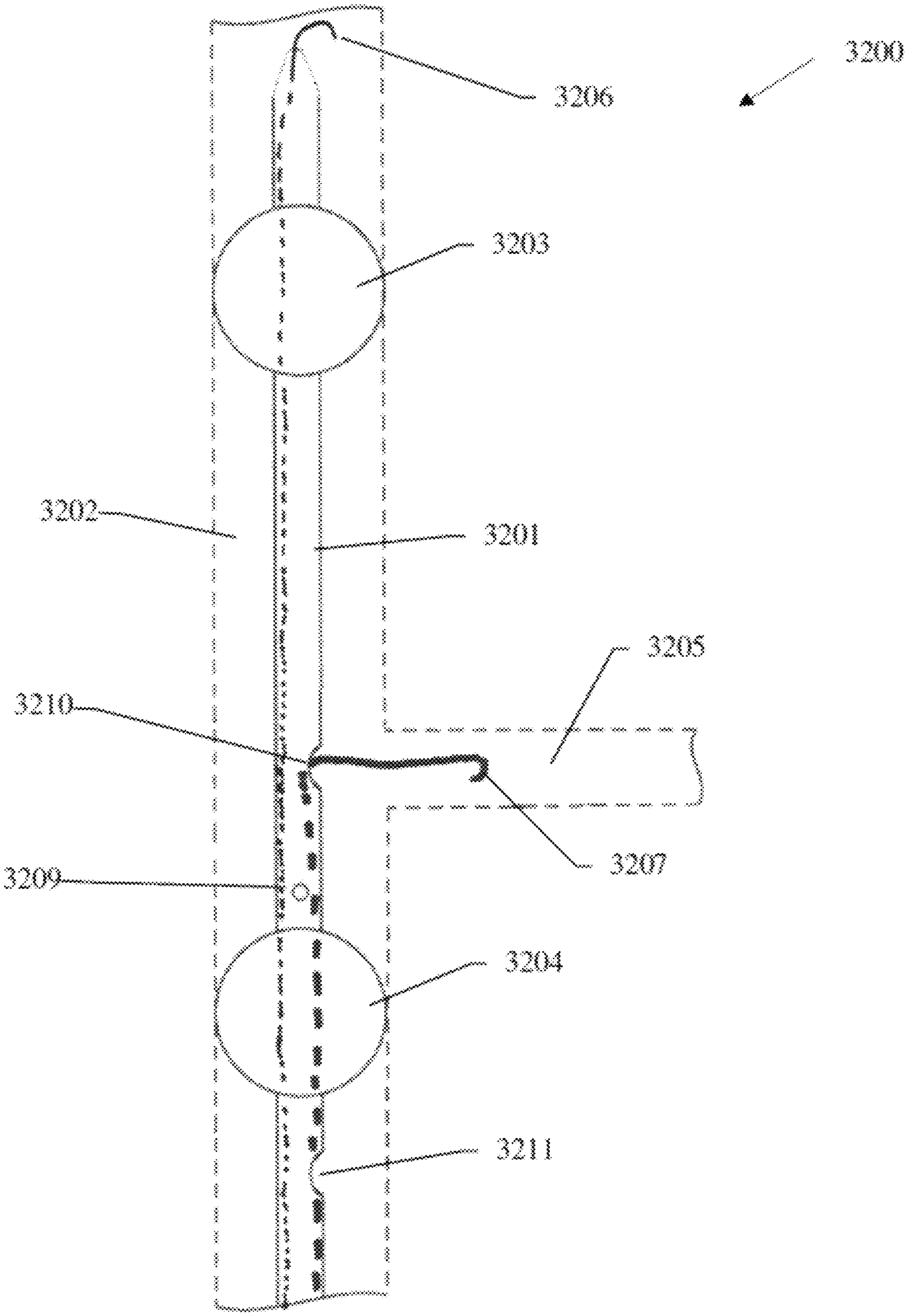
FIG. 32 shows a dual occlusion catheter system.

FIG. 32 shows a dual occlusion catheter system 3200. The dual occlusion catheter system may include a first internal channel (e.g., lumen 3201), a first expandable occlusion member 3203, a second expandable occlusion member 3204, a first guidewire 3206, and a second guidewire 3207. The first catheter 3201 may have a distal end (e.g., an end away from an operator or clinician) and a proximal end (e.g., an end toward the operator or clinician). Furthermore, the first catheter 3201 may include a first port 3210, a second port 3211 and a perfusion port 3209 disposed through the lumen of the first catheter 3201.

The first expandable occlusion member 3203 may be disposed toward the distal end of the first catheter 3201, in some variations near a distal tip of the first catheter 3201. The second expandable occlusion member 3204 may be disposed proximally with respect to the first expandable occlusion member 3203. The first port 3210 may be disposed between the first expandable occlusion member 3203 and the second expandable occlusion member 3204. Additionally, the perfusion port 3209 may also be disposed between the first expandable occlusion member 3203 and the second expandable occlusion member 3204.

As shown, the dual occlusion catheter system 3200 may be positioned within a first vessel 3202. A second vessel 3205 may branch off from the first vessel 3202. The first catheter 3201 may be positioned such that the first port 3210 is proximate or adjacent to the second vessel 3205.

The first guidewire 3206 may be used to position and/or place the dual occlusion catheter system 3200 with respect to the first vessel 3202 and the second vessel 3205. In some cases, the second guidewire 3207 may be used to align the first port 3210 with the second vessel 3205. For example, the second guidewire 3207 may be partially extended from the first catheter 3201 while the associated region is viewed through a visualization tool. Example visualization tools may include x-ray devices, fluoroscope devices and the like. A contrast dye may also be used in conjunction with the visualization tools. While the region is examined with the visualization tool, the user may partially extend the second guidewire 3207 and rotate the first catheter 3201 until the user sees an alignment of the second guidewire 3207 with the second vessel 3205.

The first expandable occlusion member 3203 and the second expandable occlusion member 3204 may be expanded (as shown) until they form a seal with an inner surface of the first vessel 3202. The first expandable occlusion member 3203 and the second expandable occlusion member 3204 may be formed from any feasible material. Expansion or inflation of the first expandable occlusion member 3203 and the second expandable occlusion member 3204 may be controlled through dedicated lumens within the first catheter 3201 (not shown). In addition, the perfusion port 3209 may be coupled to a separate lumen (also not shown) that may be used to deliver fluids (including therapeutic fluids) or gasses to the first catheter 3201. The fluids and/or gasses may be restricted generally to the region between the first expandable occlusion member 3203 and the second expandable occlusion member 3204.

The first port 3210 may be in fluid communication with the second port 3211. For example, fluids may be transferred between the first port 3210 and the second port 3211. Thus, fluids may be transferred around the second expandable occlusion member 3204 when forming a seal to the first catheter 3201. The second guidewire 3207 may be used to guide a second catheter as described below in conjunction with FIG. 33.

Figure 33:
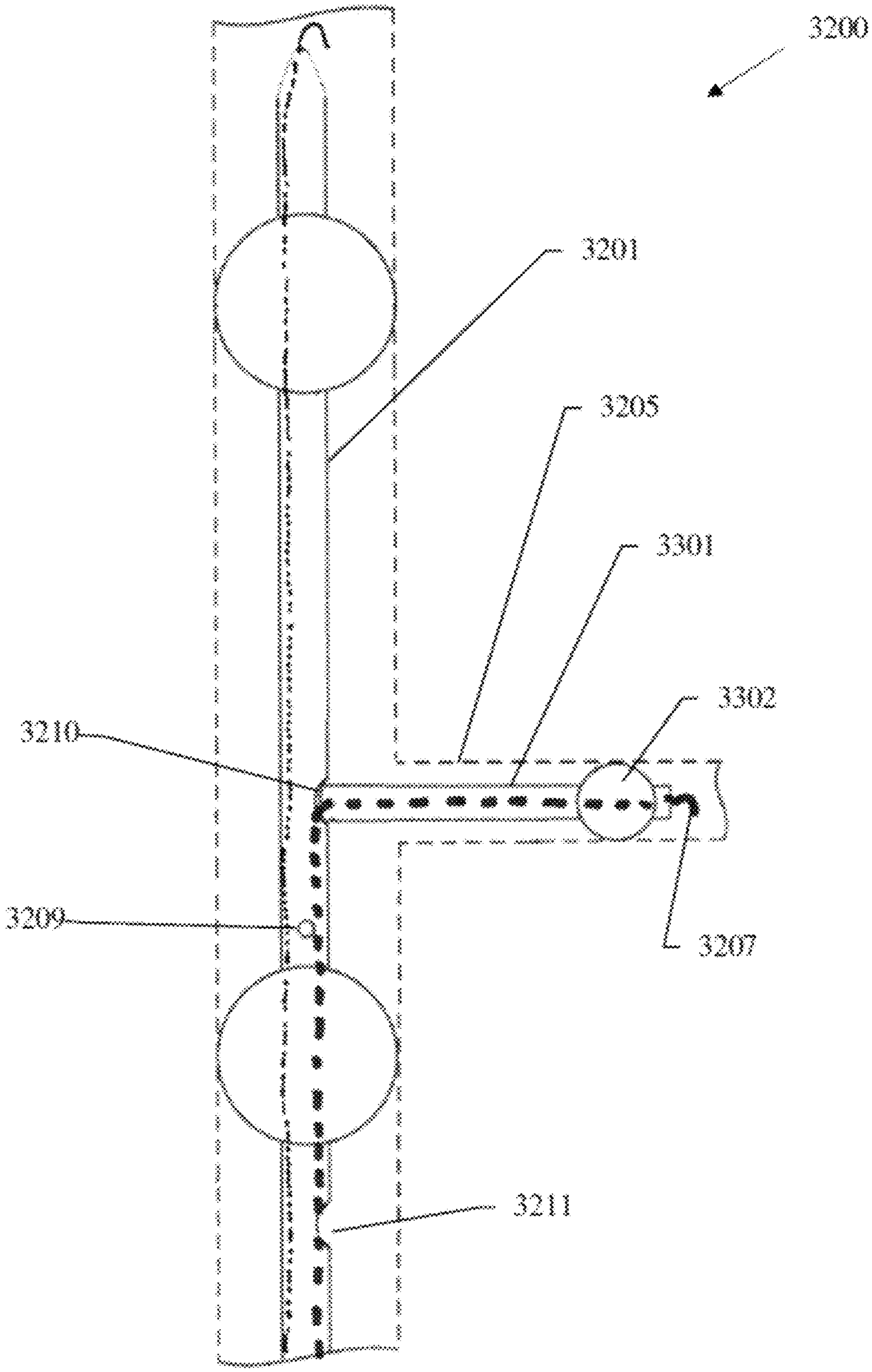
FIG. 33 shows another embodiment of the dual occlusion catheter system of FIG. 32.

FIG. 33 shows another embodiment of the dual occlusion catheter system 3200 of FIG. 32. As shown, a second elongate body (catheter 3301) having an internal channel (e.g., lumen) may extend from the first port 3210. In some variations, the second catheter 3301 may be guided by the second guidewire 3207. The second catheter 3301 may also be in fluid communication with the second port 3211.

A third expandable occlusion member 3302 may be disposed on or near an end of the second catheter 3301. The third expandable occlusion member 3302 may expand and form a seal with an inner surface or wall of the second vessel 3205. In some variations, the first expandable occlusion member 3203, the second expandable occlusion member 3204, and the third expandable occlusion member 3302 may isolate a region or section of the first vessel 3202 and the second vessel 3205. Some fluids, including therapeutic fluids, may be delivered to the isolated region or section through the perfusion port 3209.

Since the second catheter 3301 is in fluid communication with the second port 3211, fluids may be thereby transferred between the first vessel 3202 and the second vessel 3205. The fluid may be transferred around the isolated regions of the first vessel 3202 and the second vessel 3205.

In some variations, one or more of the guidewires 3206 and 3207 control fluid flow with the dual occlusion catheter system 3200. For example, position of the second guidewire 3207 may control fluid flow between the second port 3211 and the second catheter 3301. In some cases, the second guidewire 3207 may be retracted proximally with respect to the second port 3211 to enable fluid flow between the second port 3211 and the second catheter 3301.

Figure 34:
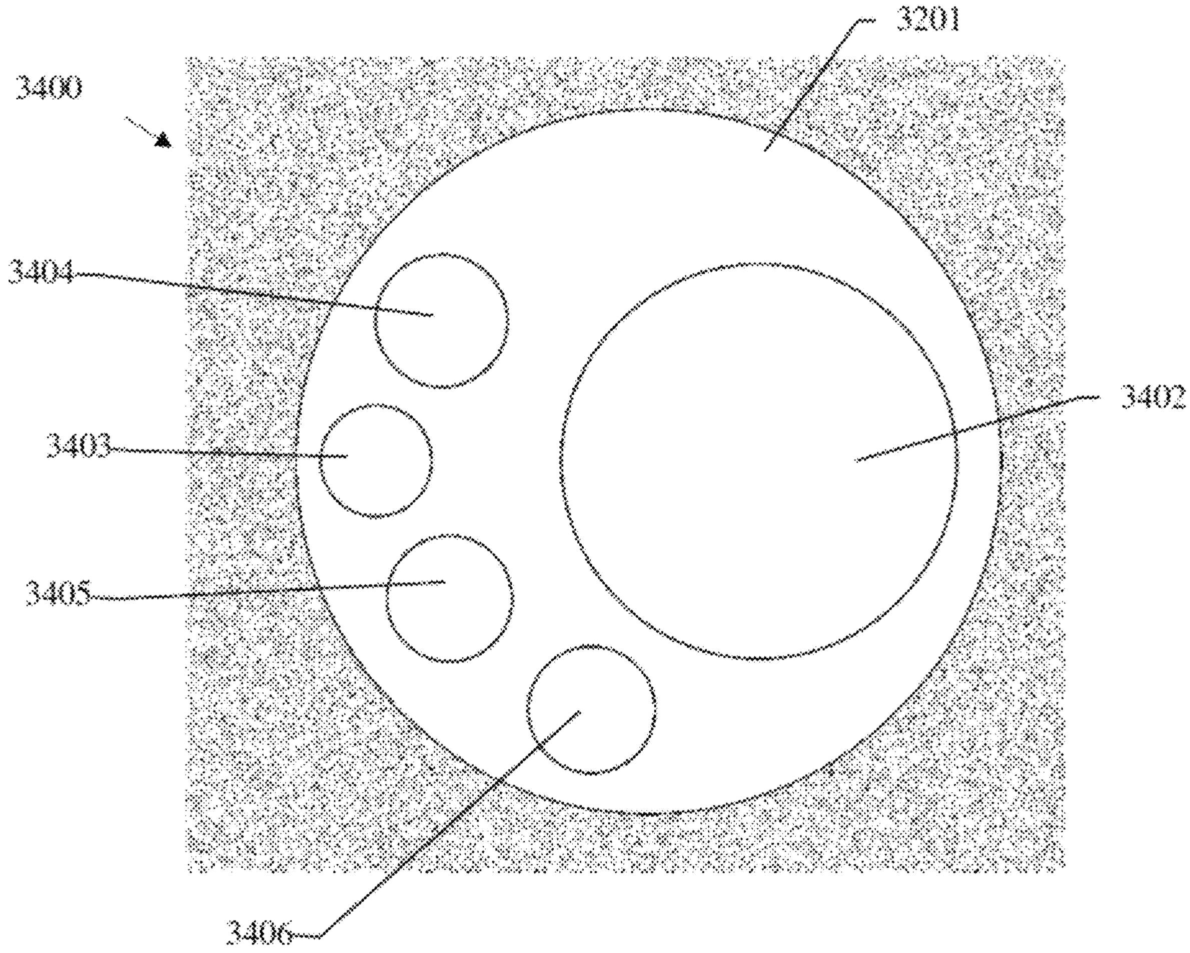
FIG. 34 shows a cross-section of the first catheter of FIGS. 32 and 33.

FIG. 34 shows a cross-section 3400 of the first catheter 3201 of FIGS. 32 and 33. The cross-section 3400 shows the first catheter 3201 having an auxiliary lumen 3402, a positioning guidewire lumen 3403, a first inflation lumen 3404, a second inflation lumen 3405, and a fluid delivery lumen 3406. Persons skilled in the art will recognize that the lumens included within the first catheter 3201 may be disposed in other relative positions. For example the position of the first inflation lumen 3404 may be exchanged with the second inflation lumen 3405, the positioning guidewire lumen 3403, or any other lumen.

The auxiliary lumen 3402 may be used to guide the second catheter 3301 and the second guidewire 3207. In some embodiments, the auxiliary lumen 3402 may be relatively larger than other lumens included within the first lumen 3201 The positioning guidewire lumen 3403 may be used to guide the first guidewire 3206. The first and second inflation lumens 3404 and 3405 may be used to control expansion/contraction (inflation/deflation) of the first expandable occlusion member 3203 and the second expandable occlusion member 3204, respectively. In some embodiments, any feasible liquid or gas may be provided to the first and second inflation lumens 3404 and 3405 to control the first expandable occlusion member 3203 and the second expandable occlusion member 3204.

The fluid delivery lumen 3406 may be in fluid communication with the perfusion port 3209. Thus, any feasible fluids (liquid therapeutics) may be provided to the perfusion port 3209 through the fluid delivery lumen 3406.

Figure 35:
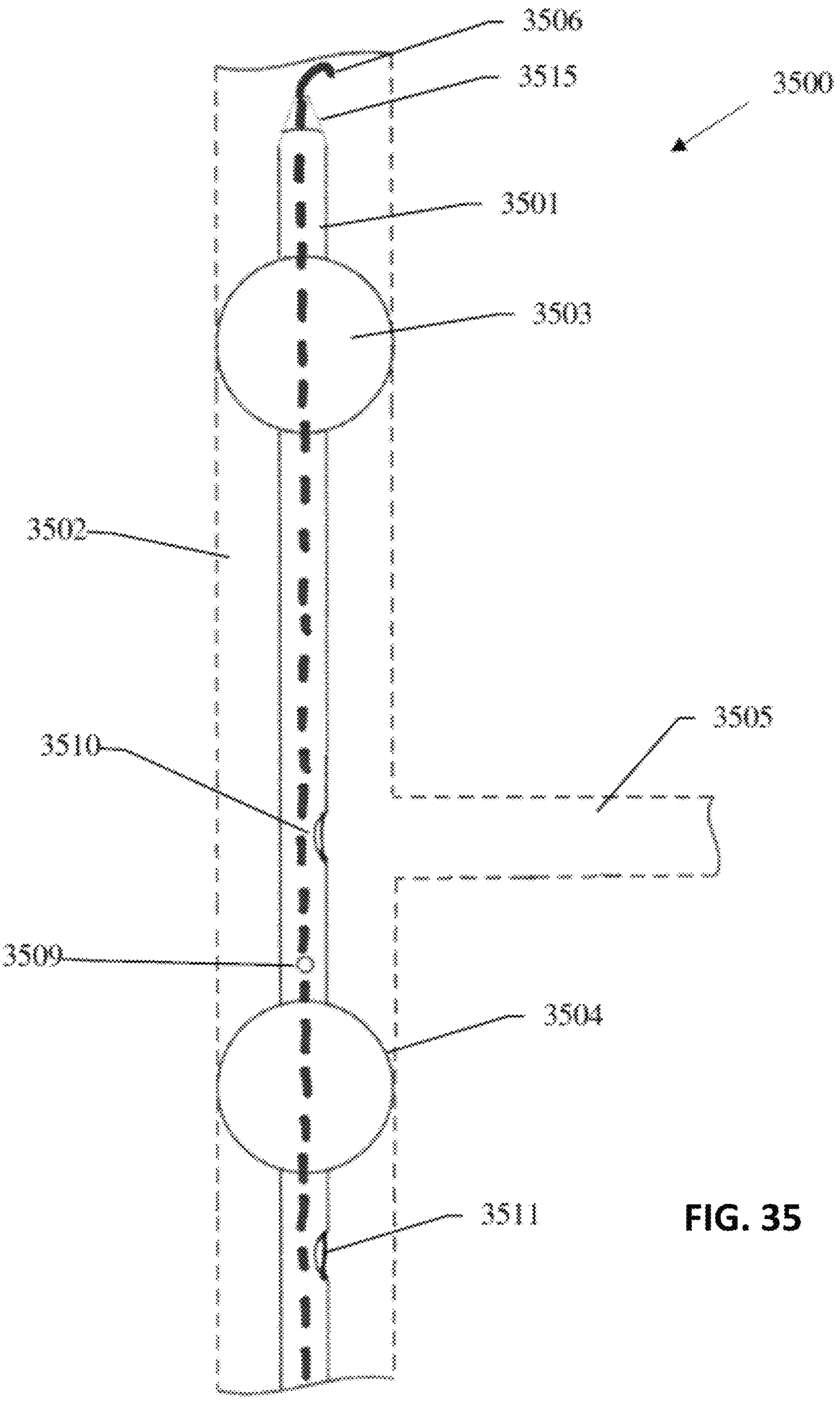
FIG. 35 shows another embodiment of a dual occlusion catheter system.

FIG. 35 shows another embodiment of a dual occlusion catheter system 3500. In contrast to the dual occlusion catheter system 3200 of FIGS. 32-34, the dual occlusion catheter system 3500 may use a single guidewire. The dual occlusion catheter system 3500 may include a first catheter 3501, a first expandable occlusion member 3503, a second expandable occlusion member 3504, a first port 3510, a second port 3511 and a perfusion port 3509. The first catheter 3501, the first expandable occlusion member 3503, the second expandable occlusion member 3504, the first port 3510, the second port 3511 and the perfusion port 3509 may be other examples of the first catheter 3201, the first expandable occlusion member 3203, the second expandable occlusion member 3204, the first port 3210, the second port 3211 and the perfusion port 3209.

As shown, the dual occlusion catheter system 3500 may be positioned within a first vessel 3502 such that the first port 3510 is proximate or adjacent to a second vessel 3505. In some variations, the dual occlusion catheter system 3500 may be guided into position by a guidewire 3506. The guidewire 3506 may be surrounded by or enclosed within the lumen of the first catheter 3501. In some variations a dilator 3515 may be disposed at or near a distal end of the first catheter 3501 to expand the first vessel 3502 and aid in the positioning of the first catheter 3501. After initial positioning, the dilator 3515 and the guidewire 3506 may be retracted. The first and second expandable occlusion members 3503 and 3504 are shown expanded and forming a seal with an inner surface of the first vessel 3502.

Figure 36:
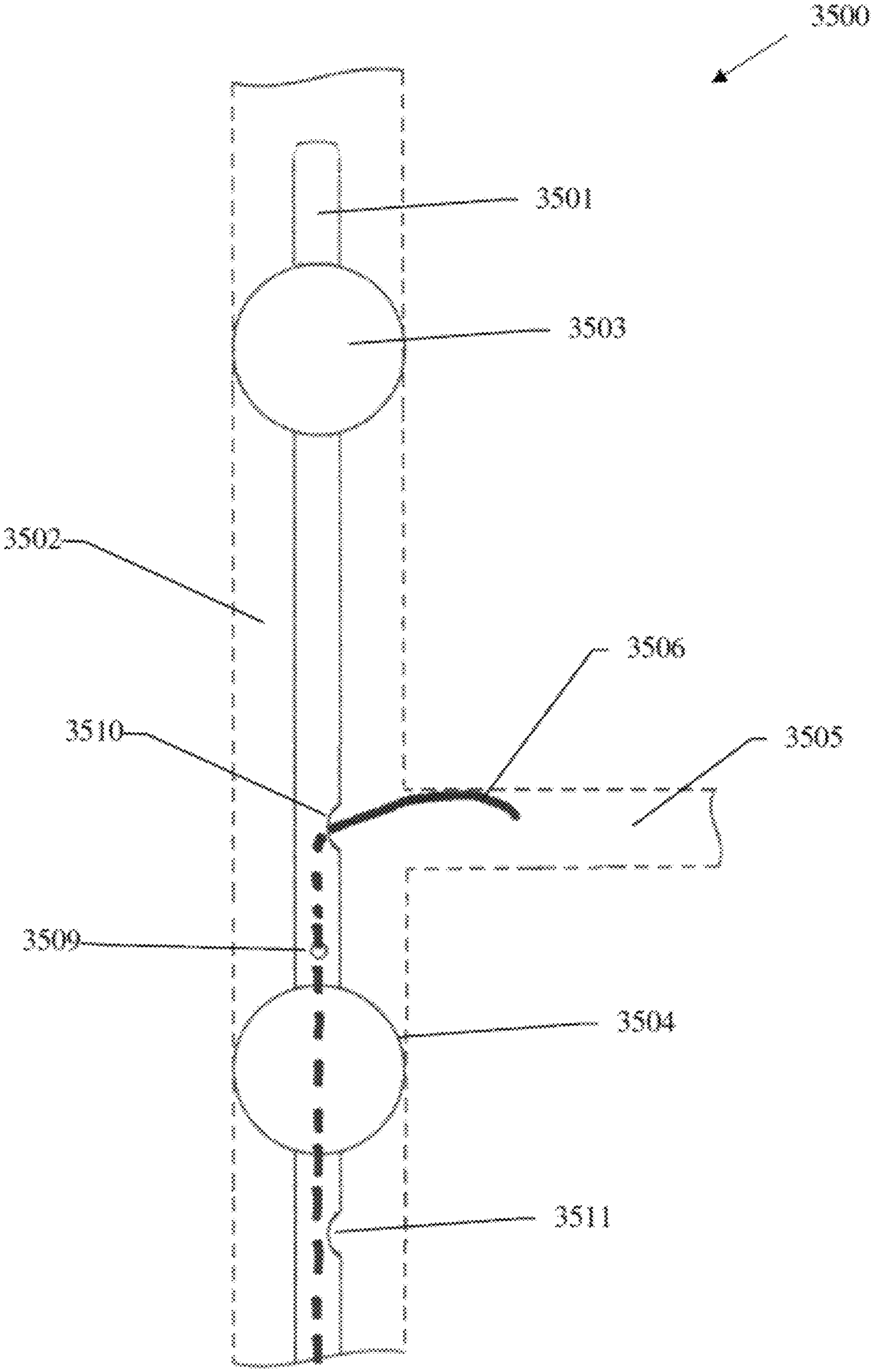
FIG. 36 shows another embodiment of the dual occlusion catheter system of FIG. 35.

FIG. 36 shows another embodiment of the dual occlusion catheter system 3500 of FIG. 35. The guidewire 3506 may have been retracted and then subsequently extended through the first port 3510. The user may rotate the first catheter 3501 until the guidewire 3506 aligns with the second vessel 3505. In some cases, the guidewire 3506 may be used to align the first port 3510 with the second vessel 3505. For example, the guidewire 3506 may be partially extended from the first catheter 3501 while the associated region is viewed through a visualization tool (x-ray devices, fluoroscope devices, and the like). A contrast dye may also be used in conjunction with the visualization tools. While the region is examined with the visualization tool, the user may partially extend the guidewire 3506 and rotate the first catheter 3501 until the user sees an alignment of the guidewire 3506 with the second vessel 3505. In some embodiments, the guidewire 3506 (for example a tip of the guidewire 3506) may be shaped to encourage the guidewire 3506 to pass through the first port 3510, particularly when not constrained by the dilator 3515.

Figure 37:
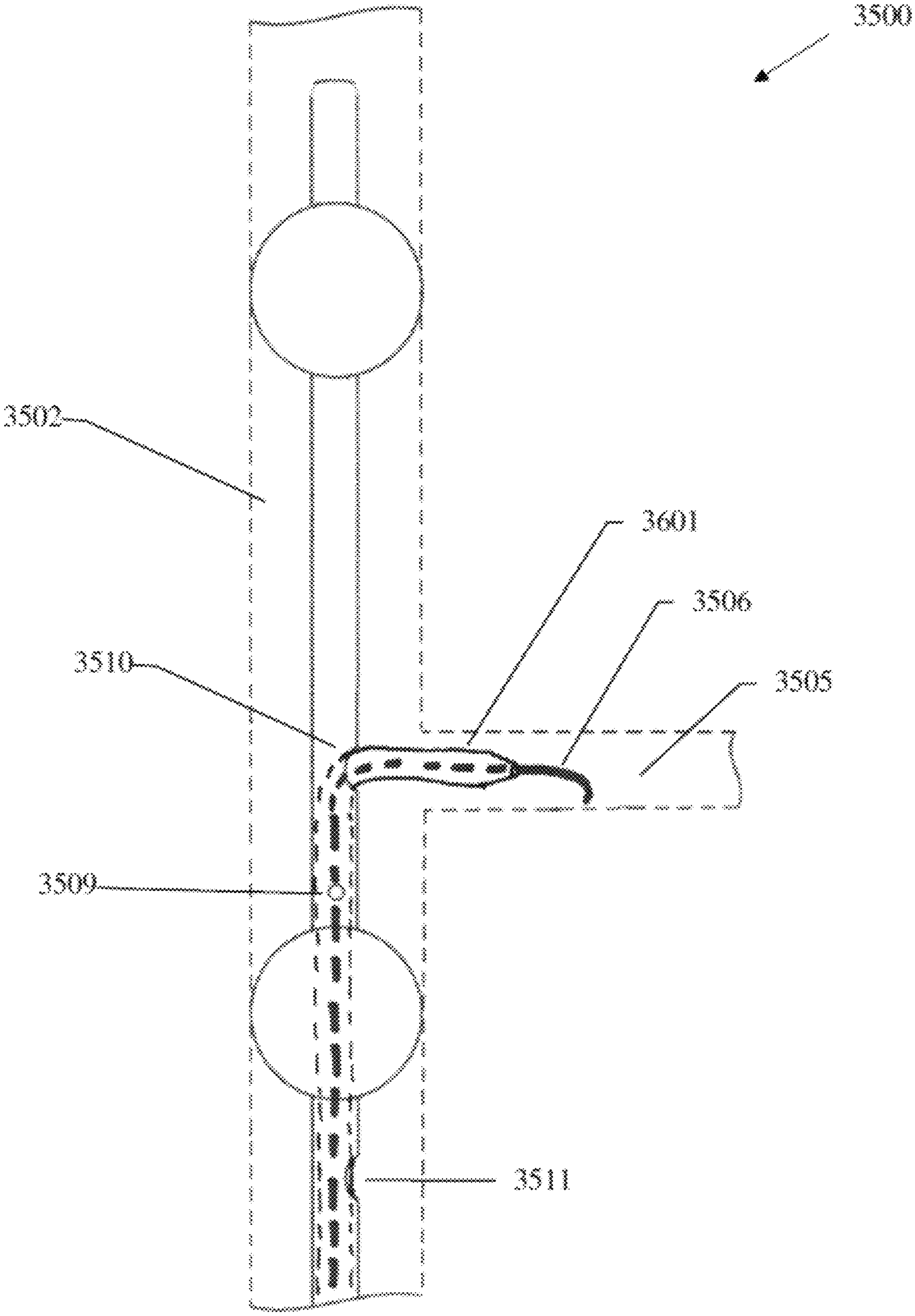
FIG. 37 shows another embodiment of the dual occlusion catheter system of FIG. 35.

FIG. 37 shows another embodiment of the dual occlusion catheter system 3500 of FIG. 35. The guidewire 3506 is shown guiding a position and placement of a second elongate body (e.g., second catheter 3601) having an internal channel (e.g., lumen) through the first port 3510 and into the second vessel 3505. In this example, if the guidewire 3506 cannot go into the vessel, then the second elongate body, having a shape and lumen that guides the guide catheter itself through the port 3510, may be extended to help guide the guidewire 3506 into the side branch vessel 3505. The guidewire 3506 may align the first elongate body and may be retracted and the reinserted into to guide the second elongate body through the first port 3510 and into the second vessel 3505. The second elongate body 3701 may be in fluid communication with the second port 3511.

Figure 38:
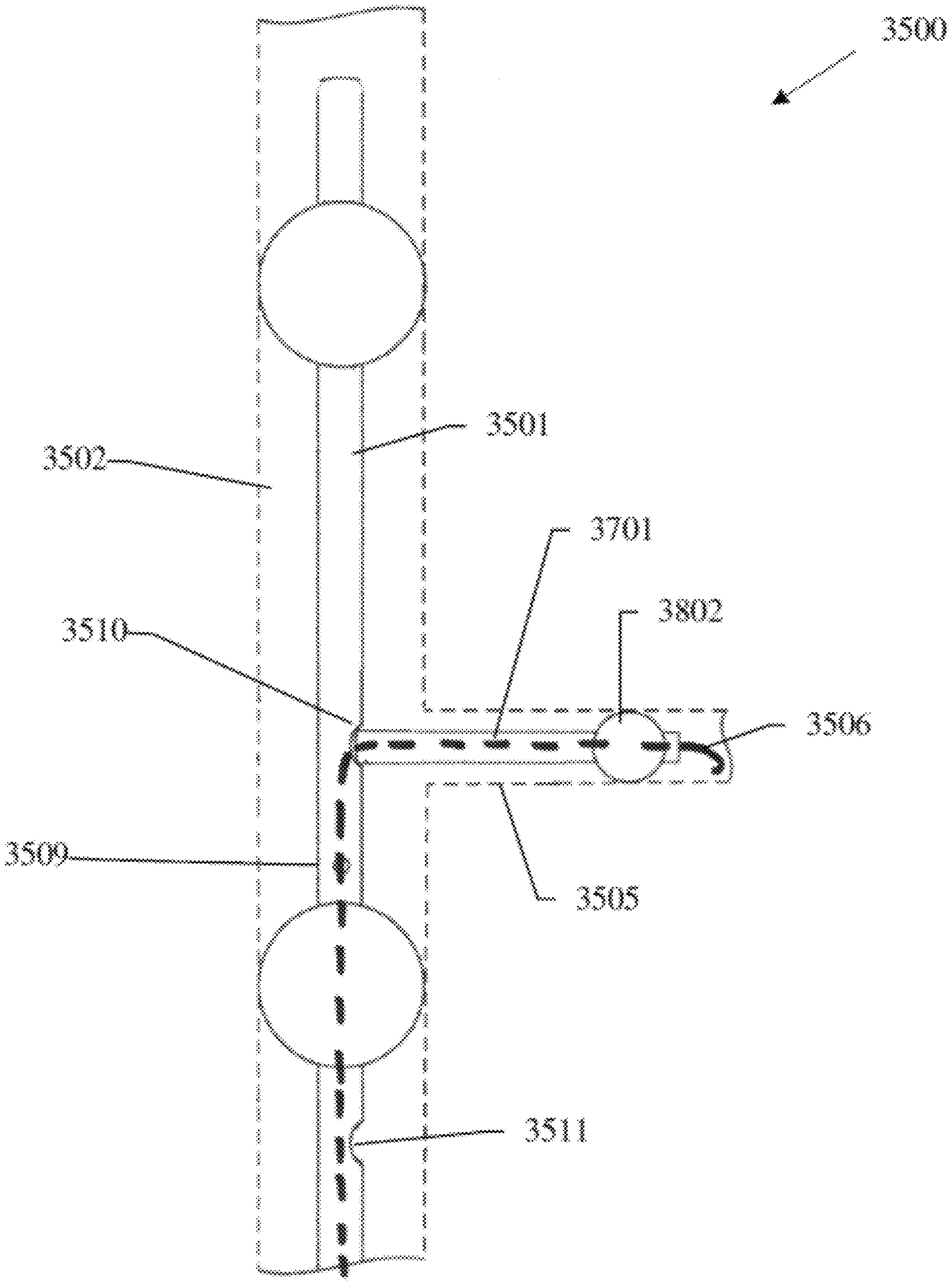
FIG. 38 shows another embodiment of the dual occlusion catheter system of FIG. 35.

FIG. 38 shows another embodiment of the dual occlusion catheter system 3500 of FIG. 35. A third expandable occlusion member 3802 is shown coupled to and disposed toward an end of the second catheter 3701. The third expandable occlusion member 3802 may be expanded and forming a seal with an inner surface of the second vessel 3505.

Similar to the dual occlusion catheter system 3200 of FIG. 32, the dual occlusion catheter system 3500 may isolate a section or portion of the first vessel 3502 and the second vessel 3505. Some fluids, including therapeutic fluids, may be delivered to the isolated region or section through the perfusion port 3509.

Since the second catheter 3701 is in fluid communication with the second port 3511, fluids may be thereby transferred between the first vessel 3502 and the second vessel 3505. The fluid may be transferred around the isolated regions of the first vessel 3502 and the second vessel 3505.

Figure 39:
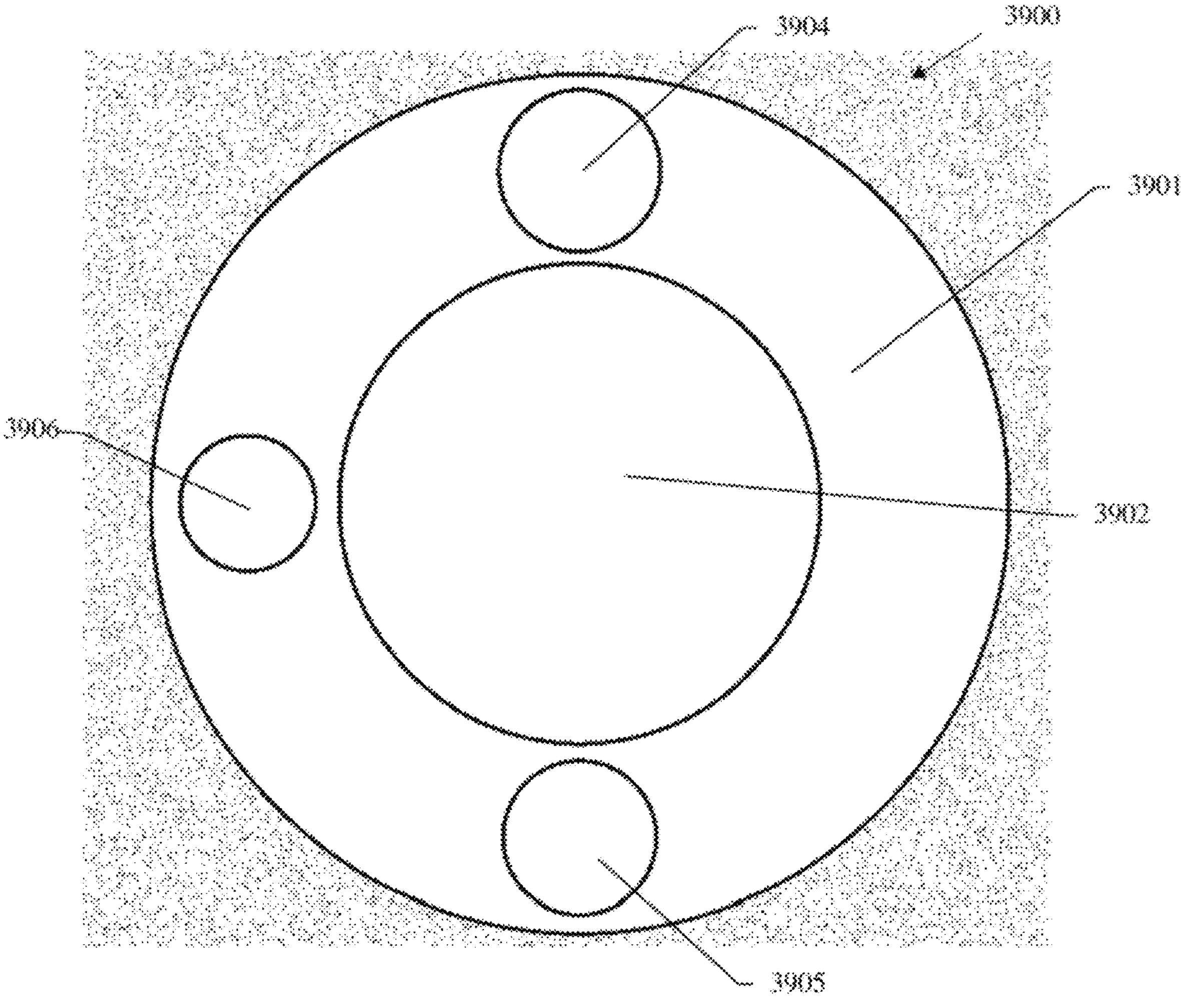
FIG. 39 shows a cross-section of the first catheter of FIGS. 36-38.

FIG. 39 shows a cross-section 3900 of the first catheter 3501 of FIGS. 36-38. The cross-section 3900 shows the first catheter 3501, a main lumen 3902, a first inflation lumen 3904, a second inflation lumen 3905, and a fluid delivery lumen 3906. Although shown in a particular relationship or placement with respect to each other, persons having skill in the art will appreciate that the lumens included within the first catheter 3501 may be positioned in any feasible position with any feasible relationship with respect to each other.

The main lumen 3902 may be used to guide the first catheter 3501 and the second lumen 3701. That is, the guidewire 3506 may translate with the main lumen 3902 to position the first catheter 3501 and also to extend or deploy the second catheter 3701 through the first port 3510 into the second vessel 3505. The first and second inflation lumens 3904 and 3905 may be used to control expansion/contraction (inflation/deflation) of the first expandable occlusion member 3503 and the second expandable occlusion member 3504, respectively. In some embodiments, any feasible liquid or gas may be provided to the first and second inflation lumens 3904 and 3905 to control the first expandable occlusion member 3503 and the second expandable occlusion member 3504.

The fluid delivery lumen 3906 may be in fluid communication with the perfusion port 3509. Thus, any feasible fluids (liquid therapeutics) may be provided to the perfusion port 3509 through the fluid delivery lumen 3906.

Figure 40:
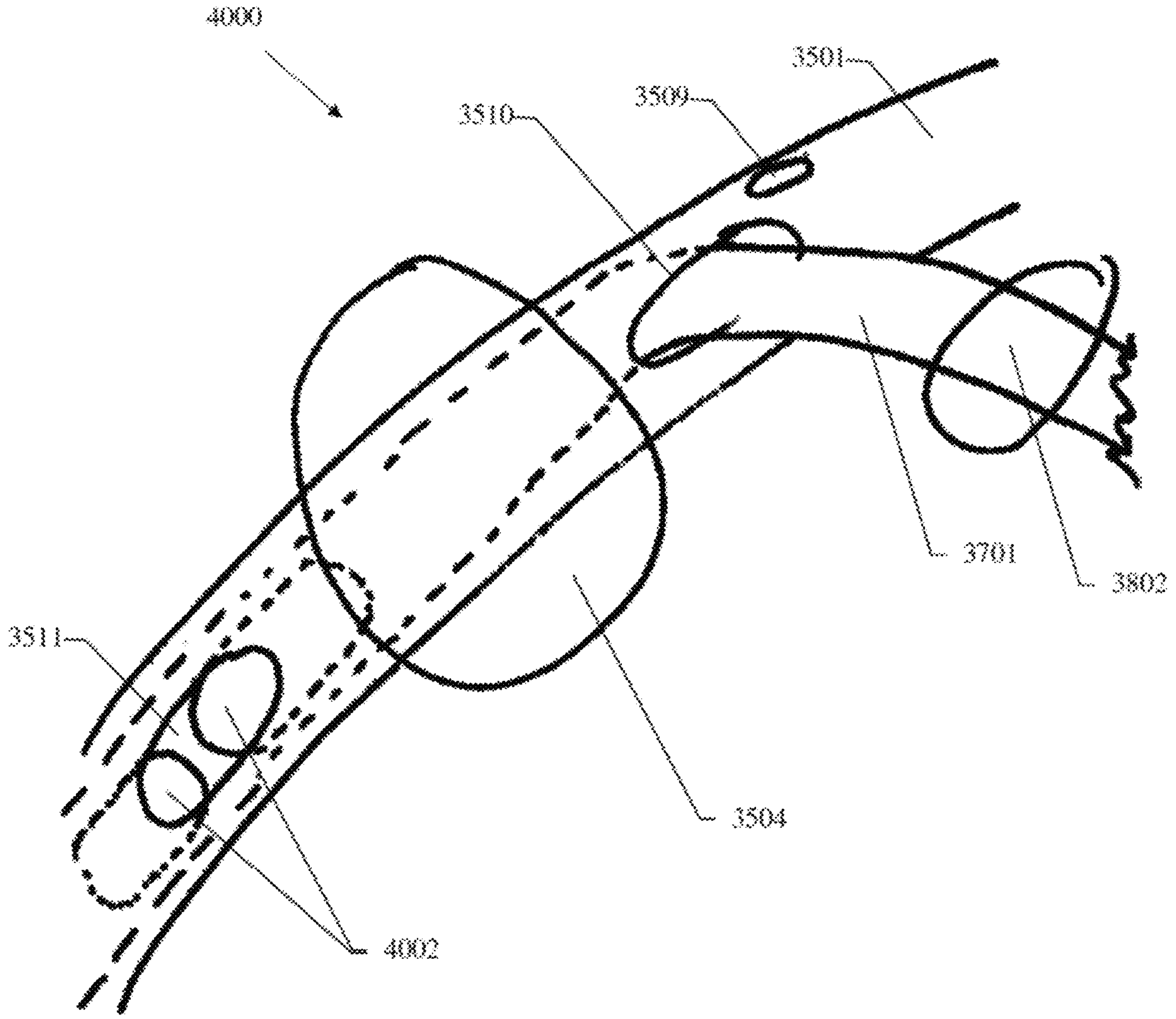
FIG. 40 depicts another view of the dual occlusion catheter system of FIG. 35.

FIG. 40 depicts another view 4000 of the dual occlusion catheter system 3500 of FIG. 35. The view 4000 shows the first catheter 3501, the first port 3510, the second port 3511, the second expandable occlusion member 3504, the perfusion port 3509, the second catheter 3701, and the third expandable occlusion member 3802.

In some variations, the second catheter 3701 may include one or more ports 4002 disposed through and located proximally with respect to the third expandable occlusion member 3802. The one or more ports 4002 may have elongate shapes and be in fluid communication with the distal end of the second catheter 3701. Similarly, the second port 3511 may have an elongate shape. The elongate shapes as well as the plurality of ports 4002 may enable the second catheter 3701 to have multiple positions within the first catheter 3501 while maintaining fluid communication between the second port 3511 and the second catheter 3701.

Therefore, as the second catheter 3701 is extended into a vessel and the one or more ports 4002 align with the second port 3511 (as shown), a fluid pathway forms between a first vessel (not shown, but surrounding the first catheter 3501 and in contact with the second expandable occlusion member 3504) and a second vessel (also not shown, but surrounding the second catheter 3701 and in contact with the third expandable occlusion member 3802). More particularly, a fluid pathway may be formed between the first vessel proximal to the second expandable occlusion member and the second vessel distal to the third expandable occlusion member.

Figure 41:
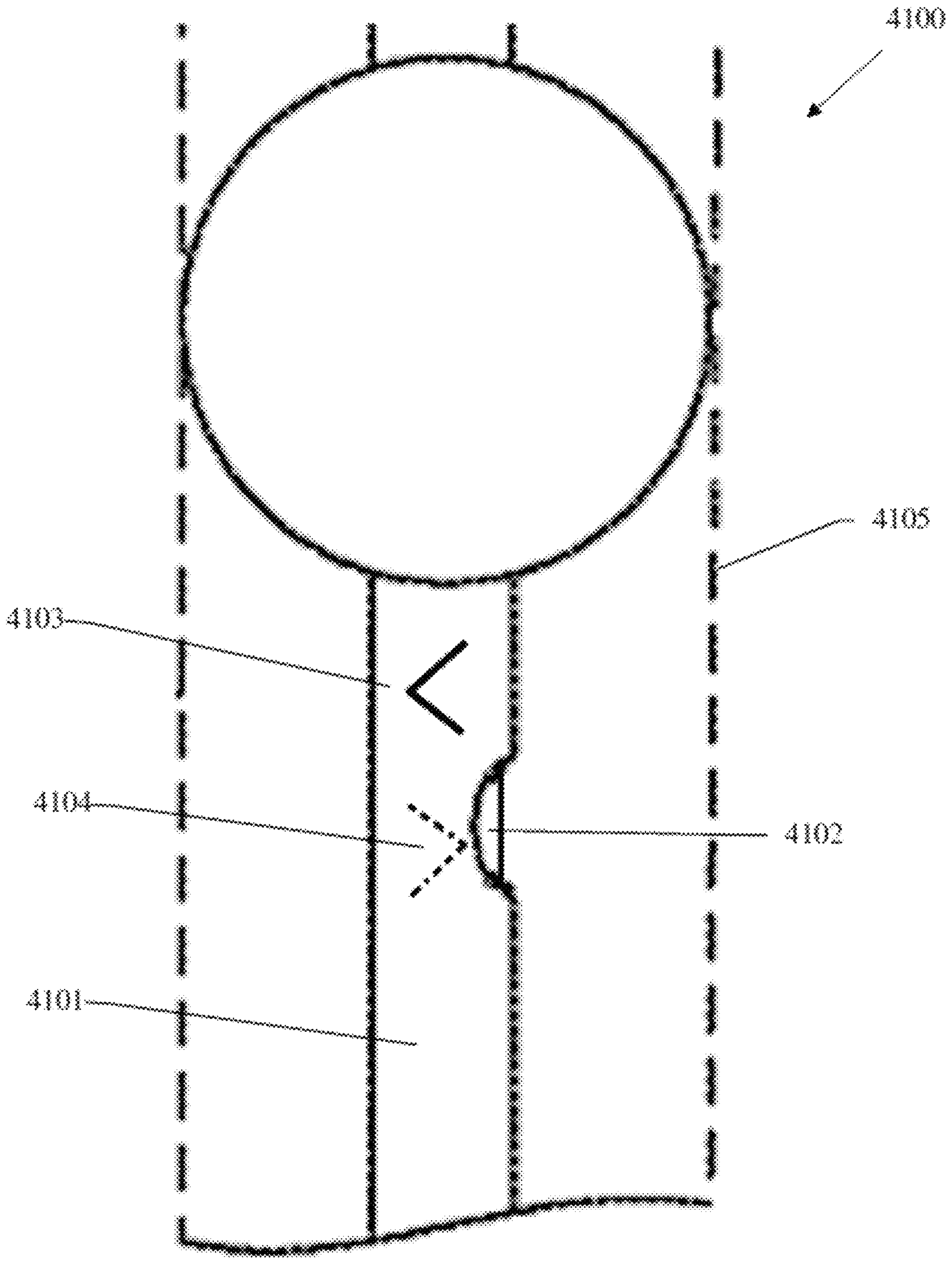
FIG. 41 shows another embodiment of a dual occlusion catheter system.
Figure 42:
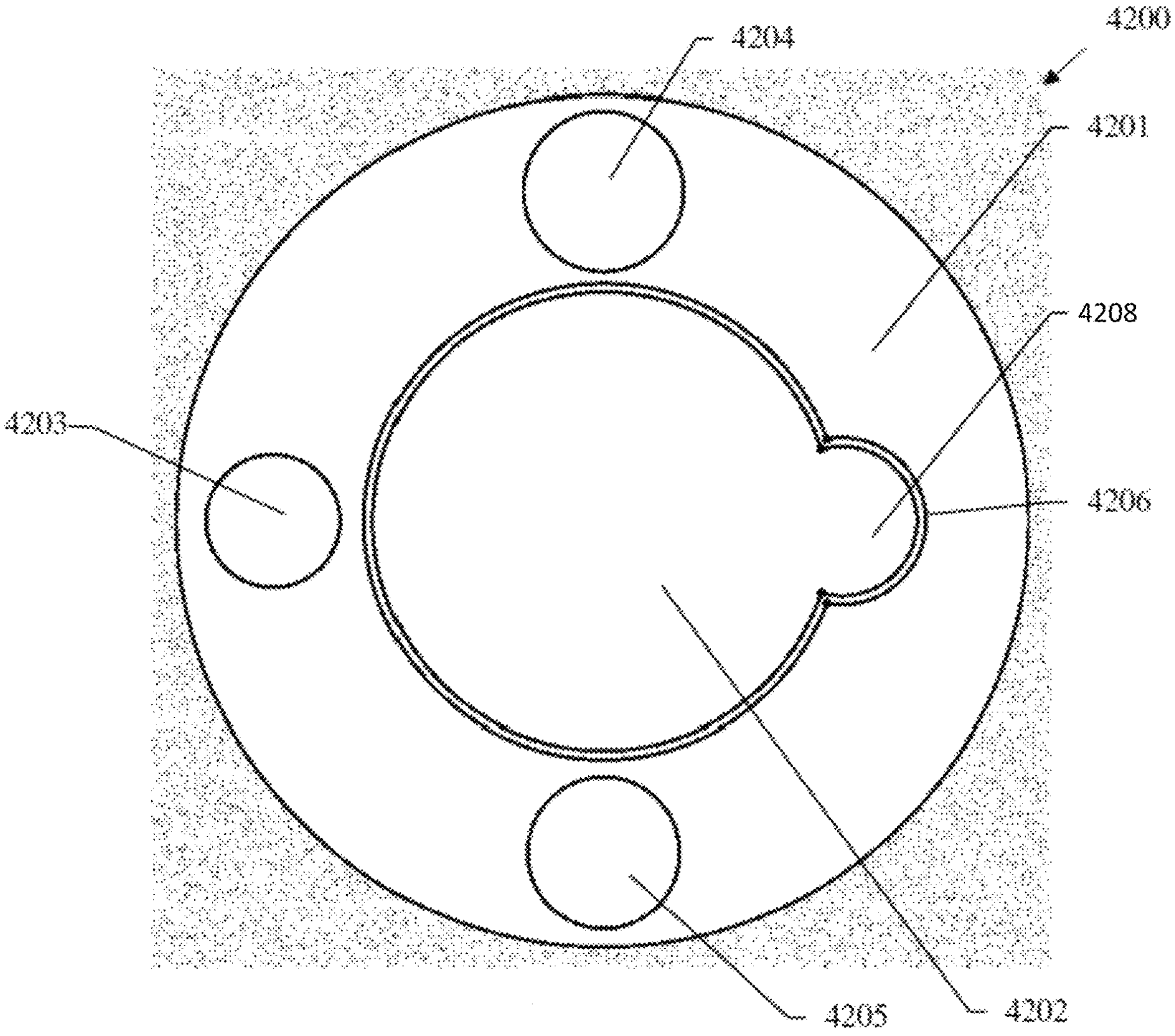
FIG. 42 shows a cross-section of another embodiment of a dual occlusion catheter system.

Rotation of the second catheter 3701 within the first catheter 3501 may interrupt one or more fluid pathways. FIGS. 41 and 42 show example features that may be included with any of the dual occlusion catheter systems described herein to monitor and/or control relative rotation between any first catheter and any second catheter.

FIG. 41 shows another embodiment of a dual occlusion catheter system 4100. The dual occlusion catheter system 4100 may be another example of the dual occlusion catheter system 3200 of FIG. 32 and/or the dual occlusion catheter system 3500 of FIG. 35. FIG. 41 shows a partial view of a dual occlusion catheter system. More particularly, FIG. 41 shows a first catheter 4101 and a second catheter 4102 of the dual occlusion catheter system 4100 disposed within a vessel 4105.

The first catheter 4101 may include a first radiopaque mark 4103 and the second catheter 4102 may include a second radiopaque mark 4104. The first and second radiopaque marks 4103 and 4104 may enable a clinician to determine an orientation, rotation, and/or position of the first catheter 4101 and the second catheter 4102 using x-ray devices, fluoroscopy equipment, or the like. In some embodiments, the first radiopaque mark 4103 and the second radiopaque mark 4104 may be symmetric, but may be arranged to indicate when the first catheter 4101 is correctly aligned with the second catheter 4102 such that the dual occlusion catheter system 4100 may be used (e.g., expandable occlusion members expanded, fluid pathways formed, and/or fluids introduced through perfusion ports).

Notably, the radiopaque marks may be placed on one surface of the first catheter 4101 and the second catheter 4102. However, since the second catheter 4102 may rotate with respect to the first catheter 4101, simple, symmetric marks may not be sufficient to show alignment. For example, a symmetric mark may incorrectly show that the catheters are aligned when the one of the catheters is actually rotated 180 degrees. Non-symmetric radiopaque marks may be used to address this shortcoming.

In some embodiments, the first radiopaque mark 4103 and the second radiopaque mark 4104 may be arrows. If the arrows are shown pointing opposite directions, then the first radiopaque mark 4103 and the second radiopaque mark 4104 may be 180 degrees apart, and therefore on opposite sides of the centerline of the catheter (as depicted in FIG. 41). If the first radiopaque mark 4103 and the second radiopaque mark 4104 are aligned and pointing the same direction, the first catheter 4101 and the second catheter 4102 would be in correct rotational alignment.

FIG. 42 shows a cross-section of another embodiment of a dual occlusion catheter system 4200. The dual occlusion catheter system may include a first catheter 4201 and a second catheter 4202. The first catheter 4201 may be an example of the first catheter 3201 of FIG. 32, and/or the first catheter 3501 of FIG. 35. The catheter 4202 may be an example of the second catheter 3301 of FIG. 33 and/or the second catheter 3701 of FIG. 37. The first catheter 4201 may include a first inflation lumen 4204, a second inflation lumen 4205, and a fluid delivery lumen 4203. The first and second inflation lumens 4204 and 4205 may be used to control expansion/contraction (inflation/deflation) of any feasible expandable occlusion members. The fluid delivery lumen 4203 may be used to deliver any feasible fluid through a perfusion port (not shown). Persons having skill in the art will recognize that the first inflation lumen 4204, the second inflation lumen 4205, and the fluid delivery lumen 4203 may have any feasible position within the first catheter 4201.

The first catheter 4201 may include a groove 4206 and the second catheter 4202 may include a protrusion 4208. Thus, both the first catheter 4201 and the second catheter 4202 may include non-circular cross-sections that may resist relative rotation of the two catheters. Although only two non-circular cross-sections are shown, any feasible non-circular cross sections may be used. For example, oval, square, triangular, rectangular, or other cross-section shapes may be used.

Figure 43:
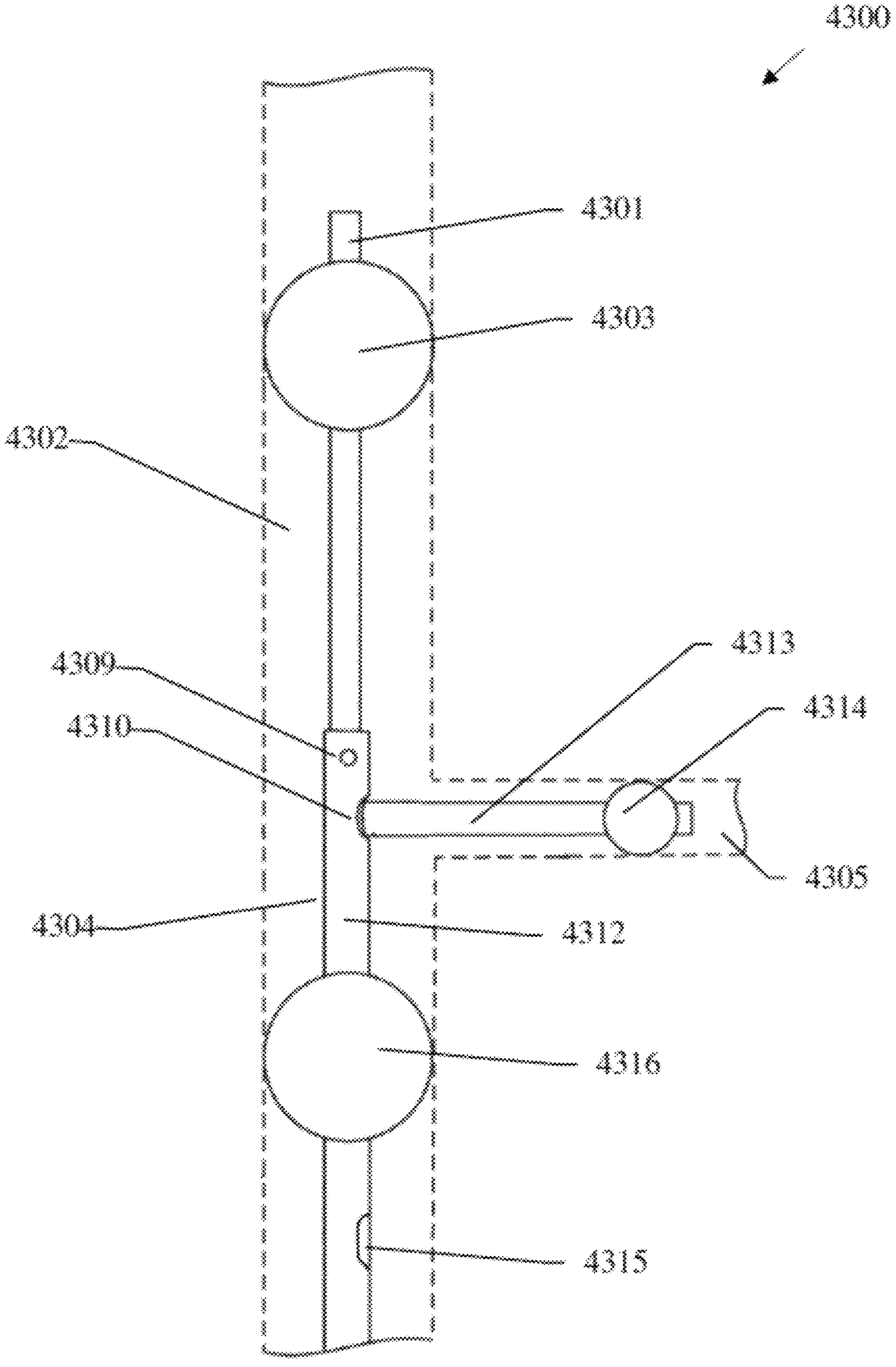
FIG. 43 shows an embodiment of an adjustable catheter system.

FIG. 43 shows an embodiment of an adjustable catheter system 4300. The adjustable catheter system 4300 may include a primary catheter 4304, a first expandable occlusion member 4303, a second expandable occlusion member 4316, an ancillary lumen 4313, and a third expandable occlusion member 4314.

Similar to the dual occlusion catheter system 3200 of FIG. 32, and the dual occlusion catheter system 3500 of FIG. 35, the primary catheter 4304 may include a first port 4310 and a second port 4315. The first port 4310 may be in fluid communication with the second port 4315. The adjustable catheter system 4300 may be inserted into or disposed with a first vessel 4302. In some cases, the adjustable catheter system 4300 may be positioned such that the first port 4310 is proximate or adjacent to a second vessel 4305. When so positioned, the ancillary catheter 4313 may be extended into the second vessel 4305.

The first and second expandable occlusion members 4303 and 4316 may be expanded to contact and form a seal with an inner surface of the first vessel 4302. Similarly, the third expandable occlusion member 4314 may be expanded to contact and form a seal with an inner surface of the second vessel 4305. The primary catheter 4304 may include a perfusion port 4309 to introduce fluids (therapeutic liquids) to the first vessel 4302.

The primary catheter 4304 may include a first catheter 4301 and a second catheter 4312. The first lumen 4301 may be slidably coupled to the second lumen 4312. In some embodiments, the first catheter 4301 may be slightly smaller than, and be disposed within, the second catheter 4312. Because the first catheter 4301 is slidably coupled to the second catheter 4312, a distance between the first expandable occlusion member 4303 and the second expandable occlusion member 4316 may be adjusted or varied by the user. Therefore, by sliding or moving the first catheter 4301 with respect to the second catheter 4312, the user can change the size of the isolated area between the first expandable occlusion member 4303 and the second expandable occlusion member 4316.

In the adjustable catheter system 4300, the first port 4310 may extend through both the first catheter 4301 and the second catheter 4312, so that the ancillary catheter 4313 may extend through the first port 4310 (and from the primary catheter 4304). Therefore, the relative positions of the first expandable occlusion member 4303 and the second expandable occlusion member 4316 may be fixed.

In some variations, the second catheter 4312 may include separate and dedicated lumens for each of the first catheter 4301 and the ancillary catheter 4313. In some other variations, the first catheter 4301 and the ancillary catheter 4313 may share a common lumen within the second catheter 4312. Such an arrangement may have a reduced number of configurations or positions that the first catheter 4301 may have with respect to the second catheter 4312 where the ancillary catheter 4313 may be able to protrude through the first port 4310.

Figure 44:
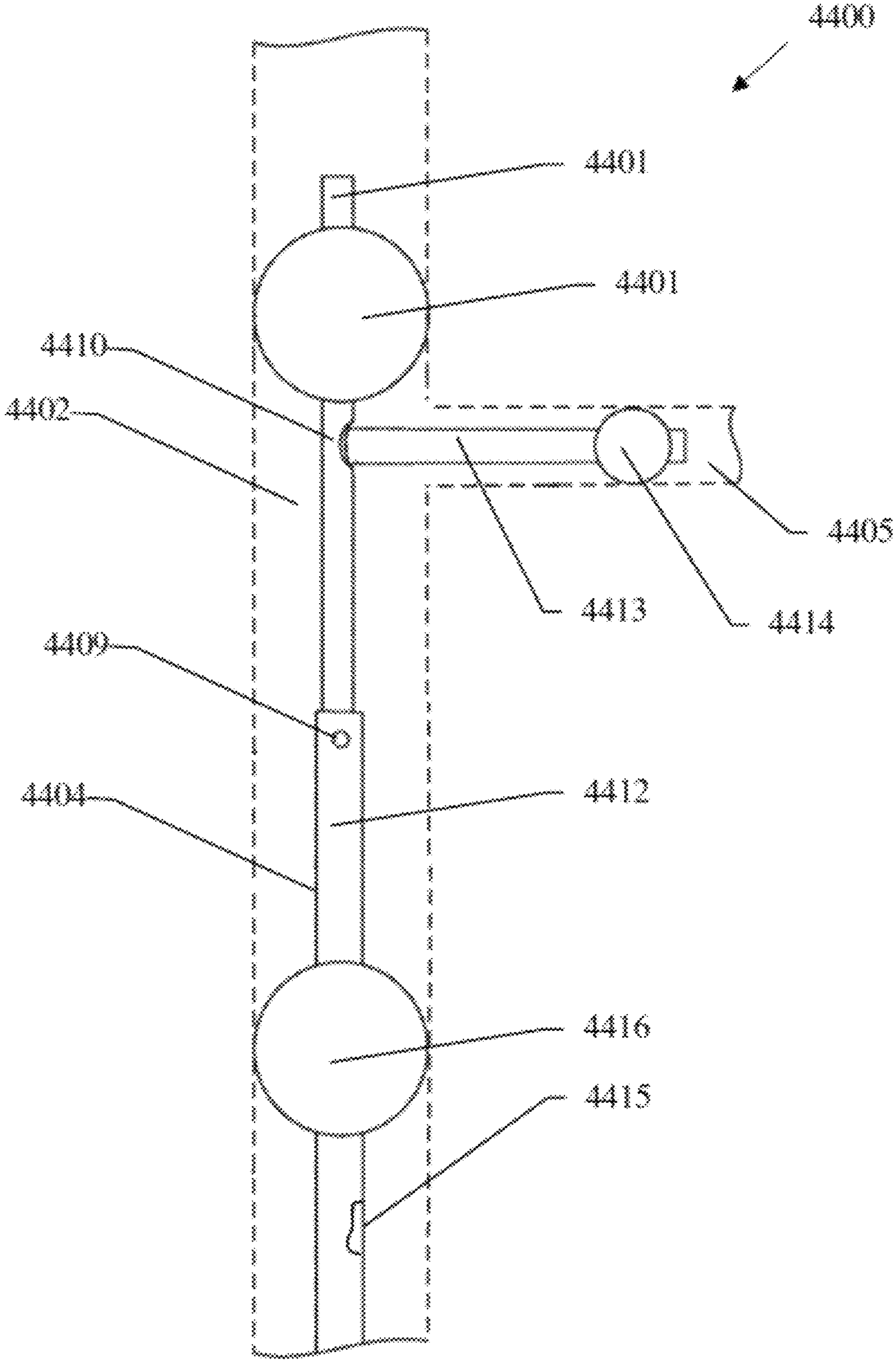
FIG. 44 shows an embodiment of an adjustable catheter system.

FIG. 44 shows an embodiment of an adjustable catheter system 4400. The adjustable catheter system 4400 may include a primary catheter 4404, a first expandable occlusion member 4403, a second expandable occlusion member 4416, an ancillary catheter 4413, and a third expandable occlusion member 4414.

Similar to the dual occlusion catheter system 3200 of FIG. 32, and the dual occlusion catheter system 3500 of FIG. 35, the primary catheter 4404 may include a first port 4410 and a second port 4415. The first port 4410 may be in fluid communication with the second port 4415. The adjustable catheter system 4400 may be inserted into or disposed with a first vessel 4402. In some cases, the adjustable catheter system 4400 may be positioned such that the first port 4410 is proximate or adjacent to a second vessel 4405.

The first and second expandable occlusion members 4403 and 4416 may be expanded to contact and form a seal with an inner surface of the first vessel 4402. Similarly, the third expandable occlusion member 4414 may be expanded to contact and form a seal with an inner surface of the second vessel 4405. The primary catheter 4404 may include a perfusion port 4409 to introduce fluids (therapeutic liquids) to the first vessel 4302.

The primary catheter 4404 may include a first catheter 4401 and a second catheter 4412. The first catheter 4401 may be slidably coupled to the second catheter 4412. In some embodiments, the first catheter 4401 may be slightly smaller than, and be disposed within, the second catheter 4412. Because the first catheter 4401 is slidably coupled to the second catheter 4412, a distance between the first expandable occlusion member 4403 and the second expandable occlusion member 4416 may be adjusted or varied by the user. Therefore, by sliding or moving the first catheter 4401 with respect to the second catheter 4412, the user can change the size of the isolated area between the first expandable occlusion member 4403 and the second expandable occlusion member 4416.

In the adjustable catheter system 4400, the first port 4410 may have a relatively fixed relationship to the first catheter 4401. Notably, the first port 4410 does not protrude or open through the second catheter 4412. Therefore, the size of the isolated area may be variable. In some variations, the second catheter 4412 may include separate and dedicated lumens for each of the first catheter 4401 and the ancillary catheter 4413. In some other variations, the first catheter 4401 and the ancillary catheter 4413 may share a common catheter within the second catheter 4312.

Figure 45:
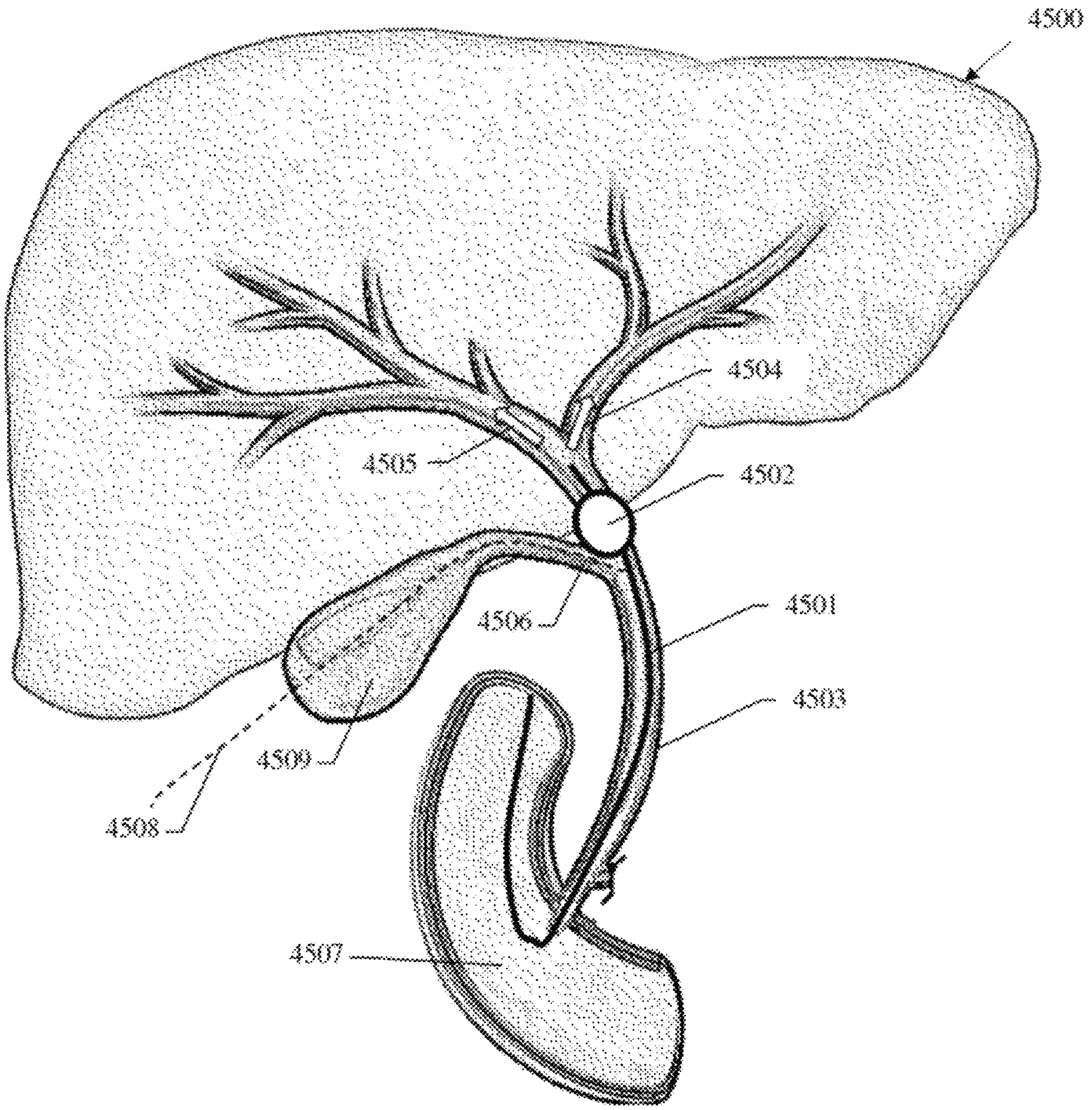
FIG. 45 shows a single occlusion catheter system 4500 placed within a biliary duct system.
Figure 46:
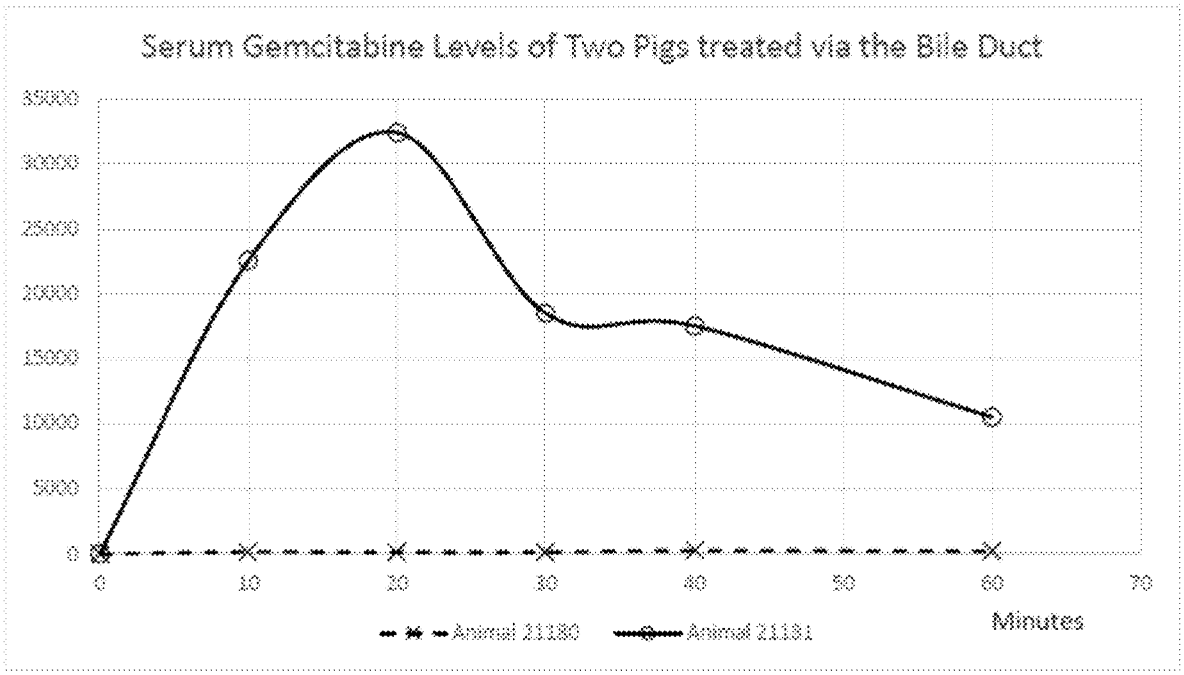
FIG. 46 shows serum gemcitabine levels collected over time during two pig labs.

FIG. 45 shows a single occlusion catheter system 4500 placed within a biliary duct system. The single occlusion catheter system 4500 may include a catheter 4501 and an expandable occlusion member 4502. As shown, the catheter 4501 may be inserted into any feasible duct within the biliary duct system. In some variations, the catheter 4501 may be inserted into the common bile duct 4503. The catheter 4501 may include a distal end (e.g., away from a user or clinician) and a proximal end (e.g., toward the user or clinician). The expandable occlusion member 4502 may be disposed near the distal end of the catheter 4501.

The expandable occlusion member 4502 may be expanded to form a seal with a vessel to which the catheter 4501 is inserted. For example, the expandable occlusion member 4502 form a seal with the common bile duct 4503. After the seal is formed, a liquid, including any feasible therapeutic liquid may be delivered through the catheter 4501 to the vessel beyond the expandable occlusion member 4502. Example therapeutic liquids may include gemcitabine. In some examples, the catheter 4501 may deliver chemotherapy drugs to the liver through biliary ducts 4504 and 4505.

In general, the apparatuses described herein may be used to treat a bile duct by insertion through the gall bladder, direct puncture into the duct (percutaneously and/or surgically) or by ERCP through the duodenum. Surprisingly, local isolation can achieve a high tissue concentration which may be particularly useful for treating an intraductal tumor. Without permeabilizing the bile duct, fluid delivered from the catheters described herein may be retained within the bile duct, and prevented, even under relatively high pressures, from passing through the bile duct into the tissue. Without being bound by theory, it is believed that the lack of gap junctions within the ductal tissue may prevent the local permeation of drug into the surrounding tissue using the catheters described herein. This can lead to a high and sustained local level of drug which may be particularly helpful for treating intraductal tumors. Thus, these methods and apparatuses may be used to treat intraductal tumors (e.g., tumors that include one or more projections within the duct and/or rupture the duct, while minimizing systemic side effects. The drug delivered as described herein may be unable to penetrate the lumen of the duct and permeate systemically.

In some examples it may be beneficial to penetrate or form penetration regions through the anatomical lumen (e.g., bile duct) that is otherwise lacking in gap junctions, e.g., by cutting, penetrating, treating, including by mechanically penetrating the wall of the anatomical lumen within the isolated region. Following delivery of material (e.g., under pressure or otherwise), the lumen may be sealed or secured by, e.g., adding a stent or other device that may include a sealing member to secure against the wall of the lumen. The stent may allow the lumen wall to heal, following the procedure, and may be left in place or may be removed.

Figure 47:
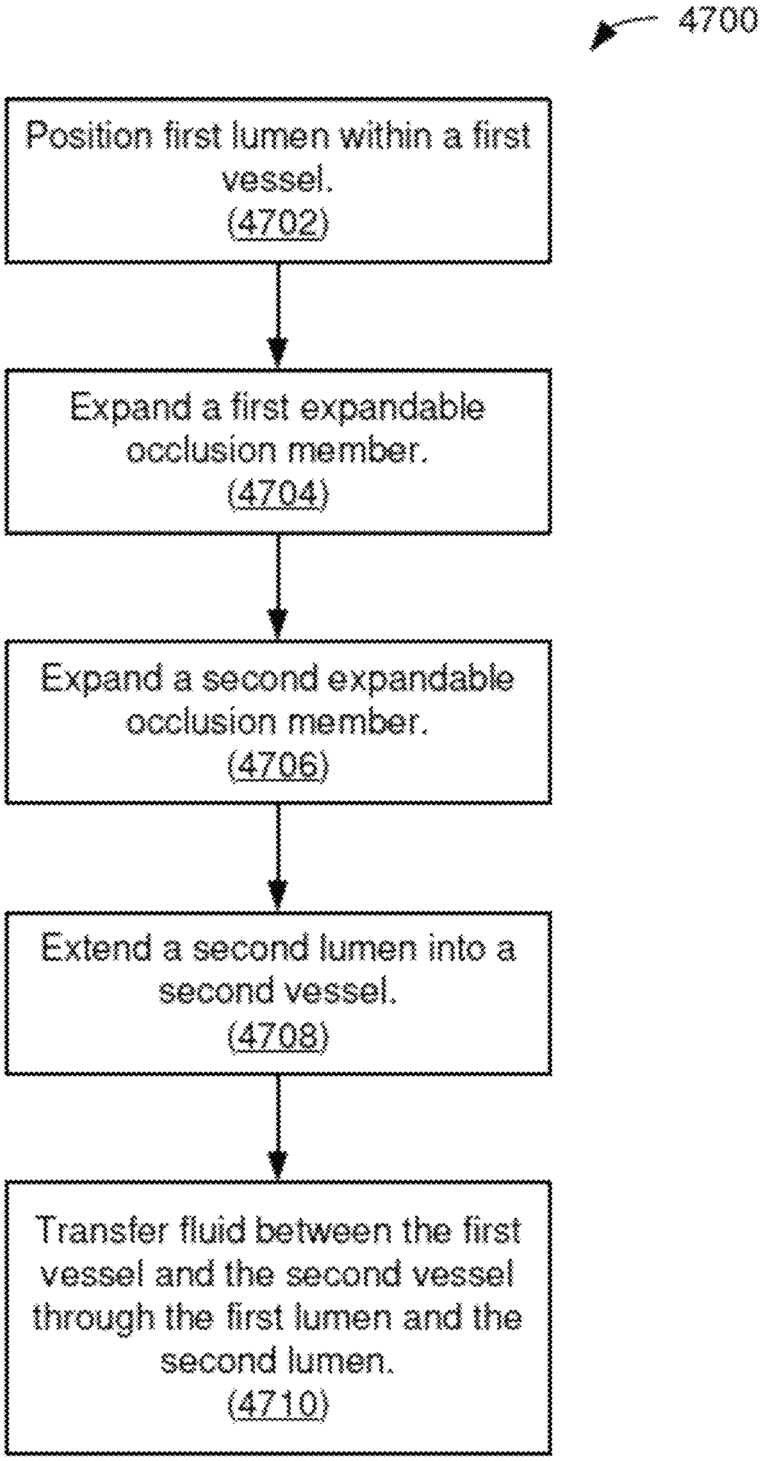
FIG. 47 is a flowchart showing an example method for delivering a liquid into a vessel, in accordance with some embodiments.

FIG. 47 is a flowchart showing an example method 4700 for delivering a liquid into a vessel, in accordance with some embodiments. Some examples may perform the operations described herein with additional operations, fewer operations, operations in a different order, operations in parallel, and some operations differently. The method 4700 is described below with respect to the dual occlusion catheter system 3200 of FIGS. 32 and 33, however, the method 4700 may be performed by any other suitable system or device.

The method 4700 begins in block 4702 as a first catheter is positioned within a first vessel. For example, the first catheter 3201 may be positioned within the catheter 3202. In some variations, the first catheter 3201 may be positioned with a visualization aid such as an x-ray device, a fluoroscopic device, or the like. The visualization aid may assist in correctly positioning the first catheter 3201 with respect to the first catheter 3202 and also a second catheter 3205. In some variations, the first catheter 3201 may be positioned by a first guidewire.

Next, in block 4704, a first expandable occlusion member may be expanded. For example, the first expandable occlusion member 3203 may be expanded within the first vessel 3202 such that the first expandable occlusion member 3203 forms a seal with an inner surface of the first vessel 3202. In some embodiments, a dedicated inflation lumen within the first catheter may be coupled to the first expandable occlusion member 3203 to provide a fluid pathway to inflate or expand the first expandable occlusion member 3203.

Next, in block 4706 a second expandable occlusion member may be expanded. For example, the second expandable occlusion member 3204 may be expanded and form a seal with an inner surface of the first vessel 3202.

Next, in block 4708 a second catheter is extended into a second vessel. For example, the second catheter 3301 may be extended into the second vessel 3205. In some variations, the second catheter 3301 may be extended by the first guidewire (e.g., the guidewire that positioned the first catheter 3201) or a second guidewire different from the first guidewire.

In some variations, after the second catheter is extended into the second vessel, a third expandable occlusion member is expanded to form a seal with an inner surface of the second vessel. In this manner, the first, second, and third expandable occlusion members may form an isolated region of the first and second vessels. In some embodiments, a second dedicated inflation lumen within the first catheter may be coupled to the second expandable occlusion member 3204 to provide a fluid pathway to inflate or expand the second expandable occlusion member 3204.

Next, in block 4710 fluid is transferred between the first vessel and the second vessel through the first catheter and the second catheter. For example, after the second catheter is extended into the second vessel and the first, second, and third expandable occlusion members have formed an isolated region, fluid may be transferred between the first vessel and the second vessel. In other words, the first catheter and the second catheter may be in fluid communication and provide a fluid pathway to transfer fluid around the isolated area of vessels.

In some variations, a separate fluid, such as a therapeutic fluid, may be infused or otherwise provided to the isolated region. For example, the therapeutic fluid may be provided to the isolated through one or more perfusion ports included on the dual occlusion catheter system 3200.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term “and/or” includes any and all combinations of one or more of the associated listed items and may be abbreviated as “/”.

Spatially relative terms, such as “under”, “below”, “lower”, “over”, “upper” and the like, may be used herein for ease of description to describe one element or feature’s relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as “under” or “beneath” other elements or features would then be oriented “over” the other elements or features. Thus, the exemplary term “under” can encompass both an orientation of over and under. The device may be otherwise oriented (rotated 90 degrees or at other orientations) and the spatially relative descriptors used herein interpreted accordingly. Similarly, the terms “upwardly”, “downwardly”, “vertical”, “horizontal” and the like are used herein for the purpose of explanation only unless specifically indicated otherwise.

Although the terms “first” and “second” may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word “comprise”, and variations such as “comprises” and “comprising” means various components can be co-jointly employed in the methods and articles (e.g., compositions and apparatuses including device and methods). For example, the term “comprising” will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as “consisting of” or alternatively “consisting essentially of” the various components, steps, sub-components or sub-steps.

As used herein in the specification and claims, including as used in the examples and unless otherwise expressly specified, all numbers may be read as if prefaced by the word “about” or “approximately,” even if the term does not expressly appear. The phrase “about” or “approximately” may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value “10” is disclosed, then “about 10” is also disclosed. Any numerical range recited herein is intended to include all sub-ranges subsumed therein. It is also understood that when a value is disclosed that “less than or equal to” the value, “greater than or equal to the value” and possible ranges between values are also disclosed, as appropriately understood by the skilled artisan. For example, if the value “X” is disclosed the “less than or equal to X” as well as “greater than or equal to X” (e.g., where X is a numerical value) is also disclosed. It is also understood that the throughout the application, data is provided in a number of different formats, and that this data, represents endpoints and starting points, and ranges for any combination of the data points. For example, if a particular data point “10” and a particular data point “15” are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term “invention” merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A dual occlusion catheter system, the system comprising:

- a first catheter having a proximal end and a distal end, the first catheter configured to be inserted into a first vessel;
- a first port disposed through the first catheter;
- a second port disposed through the first catheter, wherein the second port is proximal to an occluded region between the first port and traverses through an exterior of the first catheter, further wherein the second port is in fluid communication with the first port;
- a second catheter configured to extend through the first port into a second vessel, wherein the second vessel branches from the first vessel;
- a first guidewire configured to guide the first catheter within the first vessel; and
- a second guidewire configured to guide the second catheter into the second vessel.

2. The system of claim 1, further comprising:

a first expandable occlusion member disposed distally with respect to the first port and the second port; and a second expandable occlusion member disposed between the first port and the second port, wherein the second expandable occlusion member is within the occluded region, wherein the first expandable occlusion member and the second expandable occlusion member are configured to expand and form a seal with an inner surface of the first vessel.

3. The system of claim 2, further comprising:

a third expandable occlusion member coupled to the second catheter and configured to expand and form a seal with an inner surface of the second vessel.

4. The system of claim 2, wherein the first port is in fluid communication with the second port, further wherein the fluid communication between the first and second port is configured to bypass the second expandable occlusion element.

5. The system of claim 1, wherein fluid is transferred between the first catheter and the second catheter.

6. The system of claim 1, further comprising:

a perfusion port disposed through the first catheter between the first port and the second port; and a fluid delivery lumen coupled to the perfusion port and disposed within the first catheter, wherein the perfusion port and the fluid delivery lumen are configured to deliver a fluid to the first vessel.

7. A dual occlusion catheter system, the system comprising:

a first catheter having a proximal end and a distal end, the first catheter configured to be inserted into a first vessel and having a first expandable occlusion member disposed toward the distal end of the first catheter and a second expandable occlusion member disposed proximal to the first expandable occlusion member;

a first port disposed between the first and second expandable occlusion members;

a second port disposed through the first catheter, wherein the second port is proximal to the second expandable occlusion member and traverses through an exterior of the first catheter and further wherein the first port is in fluid communication with the second port and configured to bypass the second expandable occlusion member;

a second catheter configured to extend through the first port into a second vessel, wherein the second vessel branches from the first vessel;

a first guidewire configured to guide the first catheter within the first vessel; and a second guidewire configured to guide the second catheter into the second vessel.

8. The system of claim 7, further comprising a perfusion port; wherein the perfusion port is disposed between the first and second expandable occlusion members.

9. The system of claim 7, wherein the first port is adjacent to the second vessel.

10. The system of claim 7, further comprising a visualization tool configured to visualize a region of interest.

11. The system of claim 7, wherein the second guidewire is configured to be at least partially extended and the first catheter is configured to be rotated for alignment of the second guidewire with the second vessel.

12. The system of claim 7, further comprising a plurality of lumens of the first catheter configured to control expansion of the first and second expandable occlusion members.

* * * * *